US006270957B1

(12) United States Patent
Rich et al.

(10) Patent No.: US 6,270,957 B1
(45) Date of Patent: Aug. 7, 2001

(54) NON-IMUUNOSUPPRESSIVE CYCLOSPORINS AND THEIR USE IN THE PREVENTION AND TREATMENT OF HIV INFECTION

(75) Inventors: Daniel H. Rich, Madison, WI (US); Michael E. Solomon, Arlington, MA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/242,723

(22) PCT Filed: Aug. 25, 1998

(86) PCT No.: PCT/US98/17542

§ 371 Date: Feb. 22, 1999

§ 102(e) Date: Feb. 22, 1999

(87) PCT Pub. No.: WO99/10373

PCT Pub. Date: Mar. 4, 1999

Related U.S. Application Data

(60) Provisional application No. 60/057,751, filed on Aug. 26, 1997.

(51) Int. Cl.[7] .............................. C12Q 1/70; A61K 45/00
(52) U.S. Cl. ............................................ 435/5; 424/278.1
(58) Field of Search ............................. 435/5; 424/278.1

(56) References Cited

FOREIGN PATENT DOCUMENTS

WO 86 02080
A    4/1986  (WO).

WO 96 06857
A    3/1996  (WO).
WO 97 04005
A    2/1997  (WO).

OTHER PUBLICATIONS

Solomon, Michael Edward: "The Design and Synthesis of Novel Dual Inhibitor Cyclosporin A Conjugates" (1997) 397 pp. Avail.: UmI, Order No. DA9800016 From: Diss. Abstr. Int., B 1998, 59)2), 671, XP002086806.

Solomon, M.E., et al.: "Multi–site Inhibitors of HIV Replication Derived From Non–Immunosuppressive Analogs of Cyclosporine." 212th American Chemical Society National Meeting, Orlando, Florida, Aug. 25–29, 1996. Abstracts of Papers American Chemical Society 212 (1–2). 1996. Medi 208. ISSN: 0065–7727, XP0020868–7.

*Primary Examiner*—Hankyel T. Park
(74) *Attorney, Agent, or Firm*—Joseph T. Leone, Esq.; DeWitt Ross & Stevens S.C.

(57) ABSTRACT

Disclosed are cyclosporin analogs having amino acid residue substitutions at positions 1, 3, or 7 of the cyclosporin peptide backbone. Also disclosed are conjugates of these cyclosporin analogs in which an HIV protease inhibitor moiety is conjugated to the position-7 amino acid residue of the cyclosporin. These compounds simultaneously bind to and inhibit cyclophilin and HIV protease. The compounds have good bioavailability and potent HIV inhibitory activity. They are useful in the treatment and prevention of HIV-mediated disorders, including AIDS.

31 Claims, 4 Drawing Sheets

Figure 1:
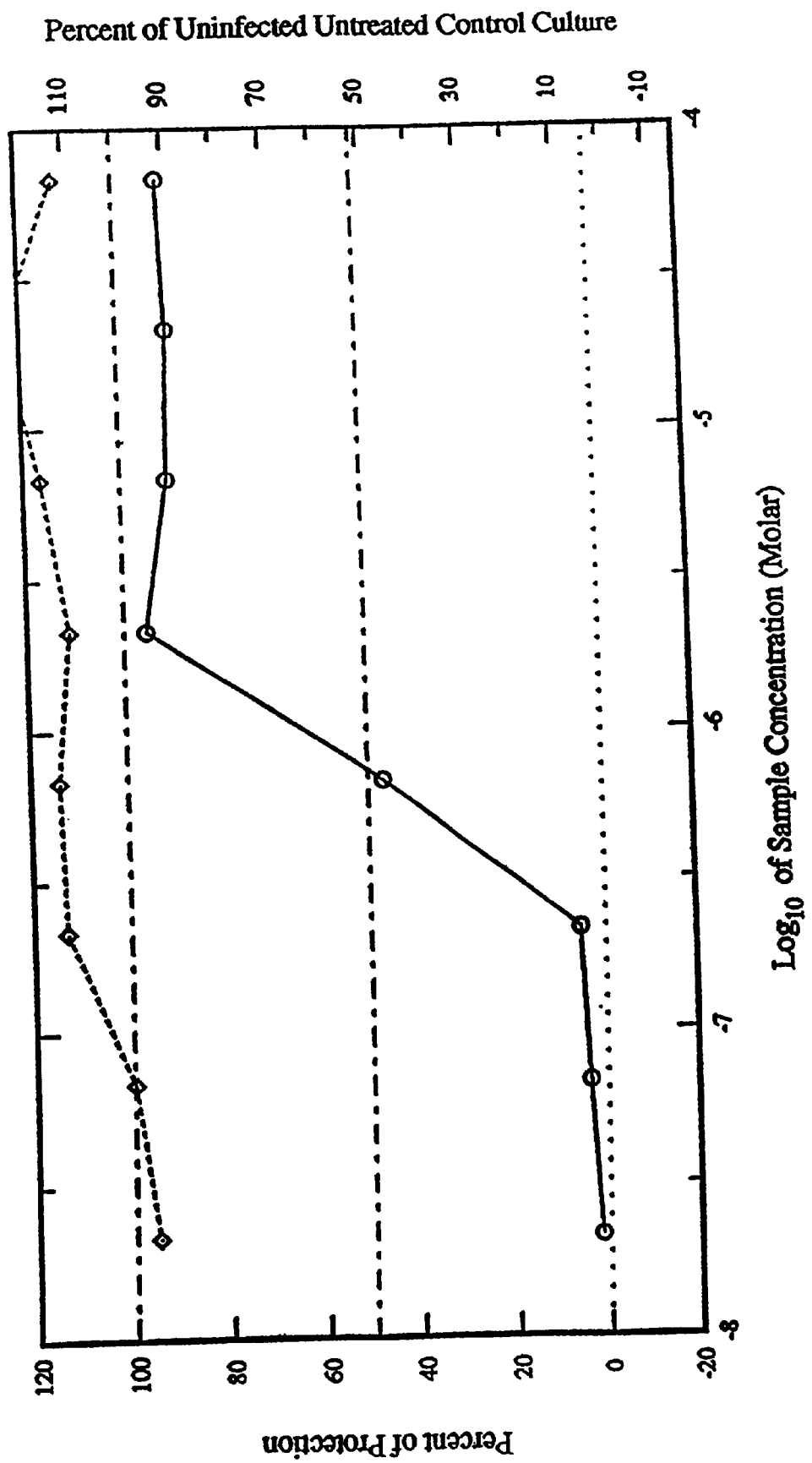

SEQUENCE LISTING

```
<160> NUMBER OF SEQ ID NOS: 26

<210> SEQ ID NO 1
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: MeBmt = (4R)
      -4-[(E)-2-butenyl]-4-N-methyl-(L)-threonine
<221> NAME/KEY: MOD_RES
<222> LOCATION: (2)
<223> OTHER INFORMATION: Abu
```

```
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeLeu = N-methyl-leucine
<221> NAME/KEY: MOD_RES
<222> LOCATION: (6)
<223> OTHER INFORMATION: MeLeu = N-methyl-leucine
<221> NAME/KEY: MOD_RES
<222> LOCATION: (8)
<223> OTHER INFORMATION: D-Ala = (D)-alanine
<221> NAME/KEY: MOD_RES
<222> LOCATION: (9)
<223> OTHER INFORMATION: MeLeu  = N-methyl-leucine
<221> NAME/KEY: MOD_RES
<222> LOCATION: (10)
<223> OTHER INFORMATION: MeLeu = N-methyl-leucine
<221> NAME/KEY: MOD_RES
<222> LOCATION: (11)
<223> OTHER INFORMATION: MeVal
<223> OTHER INFORMATION: Description of Artificial Sequence: synthetic
      polypeptide

<400> SEQUENCE: 1

Xaa Xaa Xaa Xaa Val Xaa Ala Ala Xaa Xaa Xaa
  1               5                  10

<210> SEQ ID NO 2
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu; BLOCKED
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: 4Lys(2Cl-Cbz) =
      2-chlorobenxyloxycarbonyl-protected lysine;
      BLOCKED
<223> OTHER INFORMATION: Description of Artificial Sequence: synthesized
      polypeptide

<400> SEQUENCE: 2

Xaa Val Xaa Lys
  1

<210> SEQ ID NO 3
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: MeSer(Obn) = benzyloxy-protected N-methyl-
      serine; BLOCKED
<221> NAME/KEY: MOD_RES
<222> LOCATION: (2)
<223> OTHER INFORMATION: MeLeu
<221> NAME/KEY: MOD_RES
<222> LOCATION: (4)
<223> OTHER INFORMATION: MeLeu
<221> NAME/KEY: MOD_RES
<222> LOCATION: (5    5)
<223> OTHER INFORMATION: Lys(2Cl-Cbz) = 2-chlorobenzyloxycarbonyl-
      protected lysine; BLOCKED
<223> OTHER INFORMATION: Description of Artificial Sequence: synthesized
      polypeptide

<400> SEQUENCE: 3
```

```
Xaa Xaa Val Xaa Lys
 1               5

<210> SEQ ID NO 4
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: BLOCKED, Abu
<221> NAME/KEY: MOD_RES
<222> LOCATION: (2)
<223> OTHER INFORMATION: (D)MeSer(OBn) = (D)-N-methyl-serine,
      benzyloxy-protected
<221> NAME/KEY: MOD_RES
<222> LOCATION: (3)
<223> OTHER INFORMATION: MeLeu
<221> NAME/KEY: MOD_RES
<222> LOCATION: (5)
<223> OTHER INFORMATION: MeLeu
<221> NAME/KEY: MOD_RES
<222> LOCATION: (6)
<223> OTHER INFORMATION: Lys(2Cl-Cbz) = 2-chlorobenzyloxycarbonyl-
      protected lysine;  BLOCKED
<223> OTHER INFORMATION: Description of Artificial Sequence: synthesized
      polypeptide

<400> SEQUENCE: 4

Xaa Xaa Xaa Val Xaa Lys
 1               5

<210> SEQ ID NO 5
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chlorobenzyloxycarbonyl-
      protected lysine;  BLOCKED
<223> OTHER INFORMATION: Description of Artificial Sequence: synthesized
      polypeptide

<400> SEQUENCE: 5

Xaa Xaa Xaa Xaa Val Xaa Lys
 1               5

<210> SEQ ID NO 6
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
```

```
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chlorobenzyloxycarbony-
      protected lysine;   BLOCKED
<223> OTHER INFORMATION: Description of Artificial Sequence: synthesized
      polypeptide

<400> SEQUENCE: 6

Xaa Xaa Xaa Xaa Val Xaa Lys
  1               5

<210> SEQ ID NO 7
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: (D) Ala;   BLOCKED
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
<221> NAME/KEY: MOD_RES
<222> LOCATION: (5)
<223> OTHER INFORMATION: MeLeu(3-OH) = 3-hydroxy-N-methyl-leucine
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: (D)MeSer(OBn) = (D)-N-methyl-serine,
      benzyloxy-protected
<221> NAME/KEY: MOD_RES
<222> LOCATION: (8)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 7

Xaa Xaa Xaa Xaa Xaa Xaa Xaa Xaa Val Xaa Lys
  1               5                   10

<210> SEQ ID NO 8
<211> LENGTH: 4
<212> TYPE: PRT
<213> ORGANISM: Artificial Sequence
<220> FEATURE:
<221> NAME/KEY: MOD_RES
<222> LOCATION: (1)
```

```
<223> OTHER INFORMATION: MeAla = N-methyl-alanine;  BLOCKED
<221> NAME/KEY: MOD_RES
<222> LOCATION: (3)
<223> OTHER INFORMATION: MeAla
<221> NAME/KEY: MOD_RES
<222> LOCATION: (4)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 8

Xaa Val Xaa Lys
  1

<210> SEQ ID NO 9
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: MeuLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) =
      2-chloro-benzyloxycarbonyl-protected lysine
<221> NAME/KEY: MOD_RES
<222> LOCATION: (8)
<223> OTHER INFORMATION: (D)-Ala
<221> NAME/KEY: MOD_RES
<222> LOCATION: (9)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: MeVal
<223> OTHER INFORMATION: Description of Artificial Sequence: synthesized
      polypeptide

<400> SEQUENCE: 9

Xaa Xaa Xaa Xaa Val Xaa Lys Ala Xaa Xaa Xaa
  1               5                  10

<210> SEQ ID NO 10
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)MeSer(OTBS) = (D)-N-methyl-serine,
      tert-butyldimethylsilyloxy-protected; BLOCKED
<221> NAME/KEY: MOD_RES
<222> LOCATION: (2)
<223> OTHER INFORMATION: MeLeu
<221> NAME/KEY: MOD_RES
<222> LOCATION: (4)
<223> OTHER INFORMATION: MeLeu
```

```
<221> NAME/KEY: MOD_RES
<222> LOCATION: (5)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 10

Xaa Xaa Val Xaa Lys
 1               5

<210> SEQ ID NO 11
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)MeSer = (D)-N-methyl-serine;  BLOCKED
<221> NAME/KEY: MOD_RES
<222> LOCATION: (2)
<223> OTHER INFORMATION: MeLeu
<221> NAME/KEY: MOD_RES
<222> LOCATION: (4)
<223> OTHER INFORMATION: MeLeu
<221> NAME/KEY: MOD_RES
<222> LOCATION: (5)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 11

Xaa Xaa Val Xaa Lys
 1               5

<210> SEQ ID NO 12
<211> LENGTH: 6
<212> TYPE: PRT
<213> ORGANISM: Artificial Sequence
<220> FEATURE:
<221> NAME/KEY: MOD_RES
<222> LOCATION: (1)
<223> OTHER INFORMATION: Abu; BLOCKED
<221> NAME/KEY: MOD_RES
<222> LOCATION: (2)
<223> OTHER INFORMATION: (D)-MeSer = (D)-N-methyl-serine
<221> NAME/KEY: MOD_RES
<222> LOCATION: (3)
<223> OTHER INFORMATION: MeLeu
<221> NAME/KEY: MOD_RES
<222> LOCATION: (5)
<223> OTHER INFORMATION: MeLeu
<221> NAME/KEY: MOD_RES
<222> LOCATION: (6)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 12

Xaa Xaa Xaa Val Xaa Lys
 1               5

<210> SEQ ID NO 13
<211> LENGTH: 7
<212> TYPE: PRT
<213> ORGANISM: Artificial Sequence
<220> FEATURE:
<221> NAME/KEY: MOD_RES
```

```
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)-MeSer
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chloro-benzyloxycarbony-
      protected lysine; BLOCKED
<223> OTHER INFORMATION: Description of Artificial Sequence: synthesized
      polypeptide

<400> SEQUENCE: 13

Xaa Xaa Xaa Xaa Val Xaa Lys
 1               5

<210> SEQ ID NO 14
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D) MeSer = (D)-N-methyl-serine
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 14

Xaa Xaa Xaa Xaa Val Xaa Lys
 1               5

<210> SEQ ID NO 15
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: (D)-Ala;   BLOCKED
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
```

```
<221> NAME/KEY: MOD_RES
<222> LOCATION: (5)
<223> OTHER INFORMATION: MeLeu(3-OH) = 3-hydroxy-N-methyl-leucine
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: (D)MeSer = (D)-N-methyl-serine
<221> NAME/KEY: MOD_RES
<222> LOCATION: (8)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 15

Ala Xaa Xaa Xaa Xaa Xaa Xaa Xaa Val Xaa Lys
 1               5                  10

<210> SEQ ID NO 16
<211> LENGTH: 11
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: (D)MeSer(OBn) = (D)-N-methyl-serine,
      benzyloxy-protected
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu
<221> NAME/KEY: MOD_RES
<222> LOCATION: (7)
<223> OTHER INFORMATION: Lys(2Cl-Cbz) = 2-chlorobenzyloxycarbonyl-
      protected lysine
<221> NAME/KEY: MOD_RES
<222> LOCATION: (8)
<223> OTHER INFORMATION: (D-Ala
<221> NAME/KEY: MOD_RES
<222> LOCATION: (9)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: MeVal
<223> OTHER INFORMATION: Description of Artificial Sequence: synthesized
      polypeptide

<400> SEQUENCE: 16

Xaa Xaa Xaa Xaa Val Xaa Lys Ala Xaa Xaa Xaa
 1               5                  10

<210> SEQ ID NO 17
<211> LENGTH: 6
<212> TYPE: PRT
<213> ORGANISM: Artificial Sequence
```

```
<220> FEATURE:
<221> NAME/KEY: MOD_RES
<222> LOCATION: (1)
<223> OTHER INFORMATION: BLOCKED, Abu
<221> NAME/KEY: MOD_RES
<222> LOCATION: (2)
<223> OTHER INFORMATION: MeGly
<221> NAME/KEY: MOD_RES
<222> LOCATION: (3)
<223> OTHER INFORMATION: MeAla = N-methyl-alanine
<221> NAME/KEY: MOD_RES
<222> LOCATION: (5)
<223> OTHER INFORMATION: MeAla
<221> NAME/KEY: MOD_RES
<222> LOCATION: (6)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 17

Xaa Xaa Xaa Val Xaa Lys
 1               5

<210> SEQ ID NO 18
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeAla
<221> NAME/KEY: MOD_RES
<222> LOCATION: (6)
<223> OTHER INFORMATION: MeAla
<221> NAME/KEY: MOD_RES
<222> LOCATION: (7)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 18

Xaa Xaa Xaa Xaa Val Xaa Lys
 1               5

<210> SEQ ID NO 19
<211> LENGTH: 7
<212> TYPE: PRT
<213> ORGANISM: Artificial Sequence
<220> FEATURE:
<221> NAME/KEY: MOD_RES
<222> LOCATION: (1)
<223> OTHER INFORMATION: MeLeu(3-OH) = 3-hydroxy-N-methyl-leucine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeAla
```

```
<221> NAME/KEY: MOD_RES
<222> LOCATION: (6)
<223> OTHER INFORMATION: MeAla
<221> NAME/KEY: MOD_RES
<222> LOCATION: (7)
<223> OTHER INFORMATION: Lys(2Cl-Cbz) =
      2-chloro-benzyloxycarbonyl-protected lysine;
      BLOCKED
<223> OTHER INFORMATION: Description of Artificial Sequence: synthesized
      polypeptide

<400> SEQUENCE: 19

Xaa Xaa Xaa Xaa Val Xaa Lys
  1               5

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: (D)-Ala: BLOCKED
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal
<221> NAME/KEY: MOD_RES
<222> LOCATION: (5)
<223> OTHER INFORMATION: MeLeu(3-OH) = 3-hydroxy-N-methyl-leucine
<221> NAME/KEY: MOD_RES
<222> LOCATION: (6)
<223> OTHER INFORMATION: Abu
<221> NAME/KEY: MOD_RES
<222> LOCATION: (7)
<223> OTHER INFORMATION: (D)-MeSer(OBn) = (D)-methyl-serine,
      benzyloxy-protected
<221> NAME/KEY: MOD_RES
<222> LOCATION: (8)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: Lys(2Cl-Cbz) =
      2-chloro-benzyloxycarbonyl-protected lysine;
      BLOCKED

<400> SEQUENCE: 20

Ala Xaa Xaa Xaa Xaa Xaa Xaa Xaa Val Xaa Lys
  1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: MeLeu(3-OH) = 3-hydroxy-N-methyl-leucine;
      BLOCKED
<221> NAME/KEY: MOD_RES
<222> LOCATION: (2)
<223> OTHER INFORMATION: Abu
<221> NAME/KEY: MOD_RES
```

```
<222> LOCATION: (3)
<223> OTHER INFORMATION: MeGly
<221> NAME/KEY: MOD_RES
<222> LOCATION: (4)
<223> OTHER INFORMATION: MeAla
<221> NAME/KEY: MOD_RES
<222> LOCATION: (6)
<223> OTHER INFORMATION: MeAla
<221> NAME/KEY: MOD_RES
<222> LOCATION: (7)
<223> OTHER INFORMATION: Lys(2Cl-Cbz) =
      2-chloro-benzyloxycarbonyl-protected lysine
<221> NAME/KEY: MOD_RES
<222> LOCATION: (8)
<223> OTHER INFORMATION: (D)-Ala
<221> NAME/KEY: MOD_RES
<222> LOCATION: (9)
<223> OTHER INFORMATION: MeLeu
<221> NAME/KEY: MOD_RES
<222> LOCATION: (10)
<223> OTHER INFORMATION: MeLeu
<221> NAME/KEY: MOD_RES
<222> LOCATION: (11)
<223> OTHER INFORMATION: MeVal

<400> SEQUENCE: 21

Xaa Xaa Xaa Xaa Val Xaa Lys Ala Xaa Xaa Xaa
 1               5                  10

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: BLOCKED
<221> NAME/KEY: MOD_RES
<222> LOCATION: (2)
<223> OTHER INFORMATION: HEA = hydroxyethyl amine
<221> NAME/KEY: MOD_RES
<222> LOCATION: (5)
<223> OTHER INFORMATION: BLOCKED

<400> SEQUENCE: 22

Phe Xaa Pro Ile Phe
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: Asn(Trt) = trityl-protected asparagine;
      BLOCKED
<221> NAME/KEY: MOD_RES
<222> LOCATION: (3)
<223> OTHER INFORMATION: HEA = hydroxyethyl amine
<221> NAME/KEY: MOD_RES
<222> LOCATION: (6)
<223> OTHER INFORMATION: BLOCKED

<400> SEQUENCE: 23

Asn Phe Xaa Pro Ile Phe
 1               5

<210> SEQ ID NO 24
```

```
<211> LENGTH: 6
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: Abu
<221> NAME/KEY: MOD_RES
<222> LOCATION: (2)
<223> OTHER INFORMATION: MeGly
<221> NAME/KEY: MOD_RES
<222> LOCATION: (3)
<223> OTHER INFORMATION: MeLeu
<221> NAME/KEY: MOD_RES
<222> LOCATION: (5)
<223> OTHER INFORMATION: MeLeu

<400> SEQUENCE: 24

Xaa Xaa Xaa Val Xaa Ala
 1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: MeBMT =
      (4R)-4-[(E)-2-butenyl]-4-N-methyl-(L)-threonine
<221> NAME/KEY: MOD_RES
<222> LOCATION: (2)
<223> OTHER INFORMATION: Abu
<221> NAME/KEY: MOD_RES
<222> LOCATION: (3)
<223> OTHER INFORMATION: MeGly
<221> NAME/KEY: MOD_RES
<222> LOCATION: (4)
<223> OTHER INFORMATION: MeLeu
<221> NAME/KEY: MOD_RES
<222> LOCATION: (6)
<223> OTHER INFORMATION: MeLeu

<400> SEQUENCE: 25

Xaa Xaa Xaa Xaa Val Xaa Ala
 1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: synthesized
      polypeptide
<221> NAME/KEY: MOD_RES
<222> LOCATION: (1)
<223> OTHER INFORMATION: (D)]-Ala
<221> NAME/KEY: MOD_RES
<222> LOCATION: (2)
<223> OTHER INFORMATION: MeLeu
<221> NAME/KEY: MOD_RES
<222> LOCATION: (3)
<223> OTHER INFORMATION: MeLeu
<221> NAME/KEY: MOD_RES
<222> LOCATION: (4)
<223> OTHER INFORMATION: MeVal

<400> SEQUENCE: 26

Ala Xaa Xaa Xaa
```

NON-IMUUNOSUPPRESSIVE CYCLOSPORINS AND THEIR USE IN THE PREVENTION AND TREATMENT OF HIV INFECTION

Priority is claimed to provisional application Ser. No. 60/057,751, filed Aug. 26, 1997.

GOVERNMENT RIGHTS

This invention was made with United States government support awarded by the following agencies: NIH Grant Nos: AR32007 and GM50113. The United States has certain rights in this invention.

FIELD OF THE INVENTION

The invention is directed to non-immunosuppressive cyclosporin analogs and conjugates thereof which possess anti-HIV activity. The compounds and compositions containing the same are useful in the prevention and treatment of HIV infection in humans.

DESCRIPTION OF THE PRIOR ART

Cyclosporin A (CsA) 1.1, marketed by Sandoz under the trademark "SANDIMMUNE," currently is the drug of choice for preventing rejection of transplanted human organs. CsA is a highly lipophilic, cyclic undecapeptide, cyclo(-MeBmt[1]-Abu[2]-Sar[3]-MeLeu[4]-Val[5]-MeLeu[6]-Ala[7]-(D)-Ala[8]-MeLeu[9]-MeLeu[10]-MeVal[11]-)a (SEQ. ID. NO: 1), that contains 7 N-methyl amino acid residues and the novel amino acid (4R)-4-{(E)-2-butenyl}-4-N-methyl-(L)-threonine (abbreviated as MeBmt) in the 1-position. A number of synthetic routes are known in the art for solution-phase or solid-phase synthesis of CsA. See, for example, Rich et al. (1995), "Solid Phase Synthesis of Cyclosporin Peptides." *J. Am. Chem. Soc.* 117:7279–7280; Wenger, R. M. (1984), *Helv. Chim. Acta* 67:502; and Wenger, R. M. (1985), *Angew. Chem. Int. Ed. Engl.* 24:77. CsA is depicted in structure 1.1:

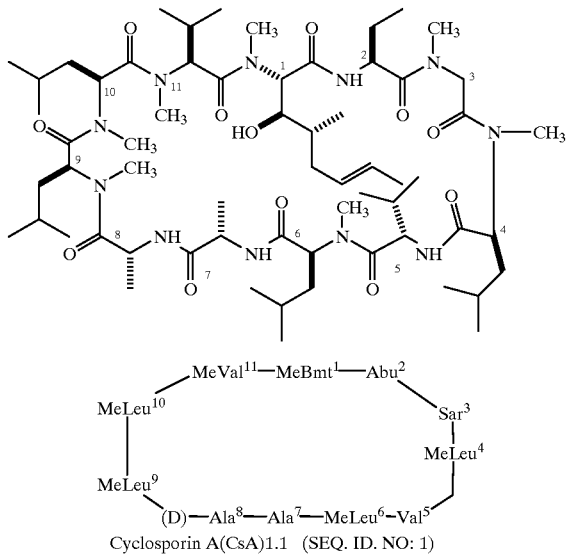

Cyclosporin A(CsA)1.1 (SEQ. ID. NO: 1)

CsA is produced by the fungus *Tolypocladium niveum* and was first isolated in 1976 by workers at Sandoz. In 1983, CsA was approved by the U.S. Food and Drug Administration for use as an immunosuppressant in the United States.

The structure of CsA has been confirmed by total synthesis, Wenger (1984), *Helv. Chim. Acta,* 67:502, and the conformations of CsA free in solution and bound to the protein cyclophilin have been solved by NMR and X-ray crystallography. Looslie et al. (1985), *Helv. Chim. Acta,* 68:682 and Mikol (1993), *J. Mol. Biol.,* 234:1119, respectively.

Several modified cyclosporin derivatives are described in the prior art. A shorthand notation for designating cyclosporin analogs has developed in which any modified amino acids and their positions relative to unmodified CsA are listed. This makes for a very simple and unambiguous designation of cyclosporin analogs based upon their differences from natural CsA. For example, an analog of CsA possessing a serine residue in place of the normal valine as the fifth amino acid residue is designated (Ser[5])-CsA. This conventional shall be consistently employed herein.

CsA analogs containing modified amino acids in the 1-position are reported by Rich et al. (1986), *J. Med. Chem.,* 29:978. Strongly immunosuppressive, anti-inflammatory, and anti-parasitic CsA analogs are described in U.S. Pat. Nos. 4,384,996; 4,771,122; and 5,284,826, all assigned to Sandoz. Among the CsA analogs described in these patents are (AllylGly[2])-CsA, ((D)-Ser[8])-CsA, and (O-(2-hydroxyethyl)(D)Ser[8]) CsA.

In 1984, Handschumacher et al. reported the discovery of a CsA binding protein, named cyclophilin (Cyp), that binds CsA with a dissociation constant of approximately 20 nM. Handschumacher et al. (1984) *Science* 226:544. It was later shown that Cyp is homologous with peptidyl prolyl-isomerase (PPIase) a ubiquitous family of proteins found in a variety of cell types. See Takahashi (1989), *Nature* 337:473 and Fischer et al. (1989) *Nature* 337:476. Cyclophilins catalyze the cis-trans isomerization of Xaa-Pro bonds and are hypothesized to play a role in protein folding, although this functionality remains uncertain. See, for instance, Fischer (1994), *Angew. Chem. Int. Ed. Engl.* 33:1415 and Schmid (1993), *Ann. Rev. Biophys. Biomol. Struct.* 22:123.

The identification of Cyp as a PPIase suggested that CsA exerts its immunosuppressive effect by inhibiting the PPIase activity of Cyp, thereby causing improper folding of proteins which are crucial to the immune response. Signal et al. (1991), *J. Exp. Med.* 173:619. This hypothesis was originally strengthened by the discovery that the macrolide FK506, 1.2, has potent immunosuppressive activity and inhibits the PPIase activity of FK506 binding protein (FKBP). Siekerka et al. (1989), *Nature* 341:755.

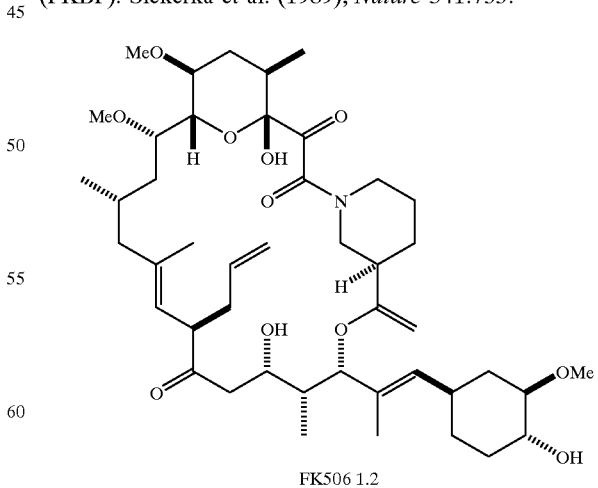

FK506 1.2

Further investigations, however, revealed several discrepancies regarding the inhibition of PPIase as a mechanism leading to immunosuppression. Foremost, the concentrations of CsA and FK506 required to ellicit immunosuppression are far lower than the concentrations of Cyp within a cell. Additionally, mutants of yeast and neurospora which lack the Cyp gene are resistant to cyclosporin but are still viable. See Agarwal et al. (1987), *Transplantation* 42:627; Tropschung et al. (1989), *Nature* 342:953; and Hayano et al. (1991), *Biochem.* 30:3041. Another observation at odds with the original hypothesis was that although CsA and FK506 exhibit very similar in vivo and in vitro effects, CsA does not bind to FKBP and FK506 does not bind to Cyp. Schreiber and Crabtree (1992), *Immunology Today* 13:136. The PPIase inhibition hypothesis was further weakened with the discovery that several potent PPIase inhibitors do not cause immunosuppression. See, for example, Somers et al. (1991), *J. Am. Chem. Soc.* 113:8045.

In 1991, Liu et al. reported that the CsA-Cyp complex binds with high affinity to calcineurin, a calcium dependent serine/threonine phosphatase, Liu et al. (1991), *Cell* 66:807; and Liu et al. (1992), *Biochem.* 31:3896. Calcineurin is thought to cleave a phosphate group from the nuclear factor of activated T-cells (NF-AT), allowing its translocation into the nucleus where it activates the gene for interleukin-2. See Schreiber and Crabtree (1992), supra. Inhibition of calcineurin is now generally accepted as the mechanism of immunosuppression by both CsA and FK506. See, for example, Ho et al. (1996), *Clin. Immun. and Immunopathology,* 80:S40. CsA binds to Cyp by an interaction between residues 9-10-11-1-2 of the CsA and an active site on Cyp residues. 9-10-11-1-2 of CsA are therefore referred to as the "binding domain." Calcineurin is bound to CsA by an analogous interaction including residues 4-5-6-7-8 of CsA. These residues are therefore referred to as the "effective domain":

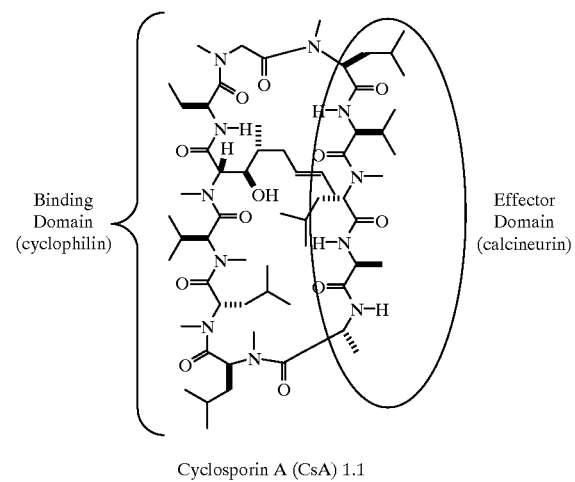

Cyclosporin A (CsA) 1.1

In the late 1980's, CsA was reported to exhibit anti-HIV activity. See, for instance, Wainberg et al. (1988), *Blood,* 72:1904; Karpas et al. (1992), *Proc. Natl. Acad. Sci. USA,* 89:8351; and Bell et al. (1993), *Proc. Natl. Acad. Sci. USA,* 90:1411. Although it originally seemed counterintuitive to use an immunosuppressant suppressant to treat a viral infection that compromises the immune system, the anti-HIV activity of CsA was at first attributed to the inhibition of T-cell activation. However this hypotheses was disproved when non-immunosuppressive CsA analogs were also found to have anti-HIV activity. Bartz et al. (1995), *Proc. Natl. Acad. Sci. USA,* 92:5381; and Rosenwirth et al. (1994), *Antimicrobial Agents and Chemotherapy,* 38:1763.

Regarding HIV and its replication in human T-cells, HIV protease is an aspartic protease that cleaves the immature viral protein gag-pol into mature structural proteins and enzymes. HIV protease is an essential enzyme in the replication of the HIV virus. Katz et al. (1994), *Annual Rev. Biochem.,* 63:133. A decade of intense research has produced four FDA-approved HIV protease inhibitors, saquinivar 1.9, ritonavir 1.10, indinivar 1.11, and nelfinivar 1.12; and one compound currently in phase III trials, VX-478 1.13. The structure of these compounds are shown below:

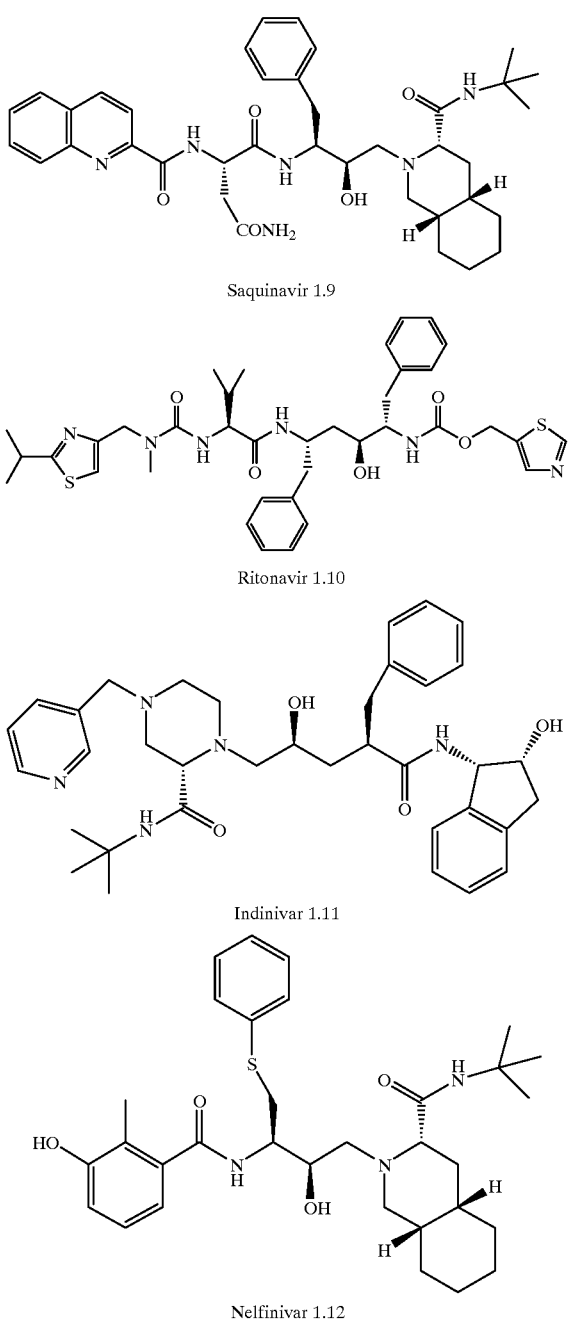

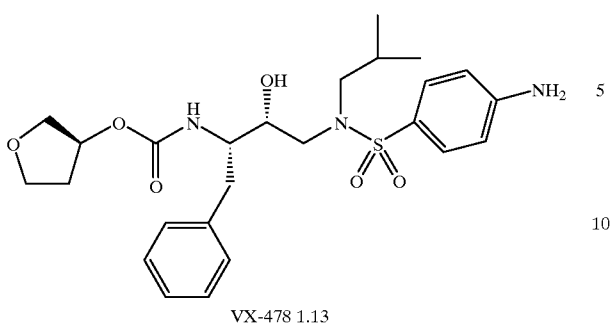

VX-478 1.13

Unfortunately, initial reports of clinical success by treatment with a single protease inhibitor have been tempered by the rapid onset of resistance. Molla et al. (1996), *Nature Medicine*, 2:760. Due to the poor fidelity of reverse transcriptase, the enzyme that produces double-stranded DNA from the viral RNA, a large number of genetic mutations of the virus are produced. The low fidelity of the reverse transcriptase reaction is compounded by the massive turnover of viral particles during the HIV life cycle. Ho et al. (1996), *Science*, 271:1582, have calculated that the decay half-life of virions is on the order of 0.24 days and that for infected cells the decay half-life is 1.5 days. These numbers indicate that every six hours approximately one-half of the circulating virus is removed and replenished and that approximately 10.3 billion virions are produced and released into the bloodstream each day in an infected individual. Due to the low fidelity of the reverse transcriptase, mutations will occur at virtually every position in the viral genome, along with some double mutants. The rapid emergence of resistance to single-compound therapies is therefore not surprising.

Although the first generation protease inhibitors, in combination with reverse transcriptase inhibitors, have provided the most effective anti-HIV therapies to date, there is still a need for more potent HIV protease inhibitors which have increased bioavailability and half-life, and less susceptibility to loss of efficacy due to mutations in the virus.

Recently, DuPont-Merck researchers reported several cyclic ureas that bind tightly to HIV protease in nanomolar concentrations. However, clinical trials on one of these compounds (DMP-323) 1.14 were discontinued to poor water solubility and first-pass metabolism. DeLucca (1997), *Drug Disc. Today*, 2:6). DMP-450 1.15, a second generation cyclic urea, has comparable potency to DMP-323 and achieves much higher plasma concentrations. Another cyclic urea, designated SD-146 1.16 displays excellent anti-HIV potency ($IC_{90}$=5.1 nM). However, the compound is extremely insoluble in both water and most oils. Jadhav et al. (1997), *J. Med. Chem.*, 40:181. The structure of these cyclic urea HIV protease inhibitors are shown below:

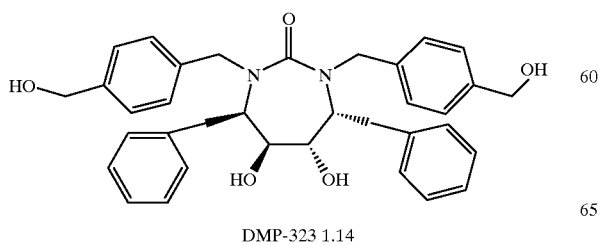

DMP-323 1.14

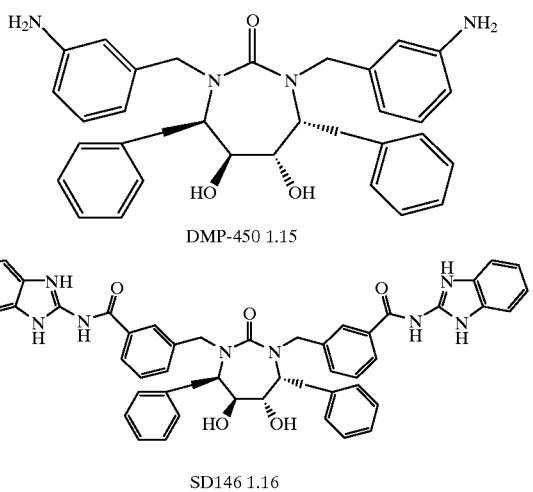

Other non-peptide HIV protease inhibitors have been reported by investigators at Upjohn and Gilead:

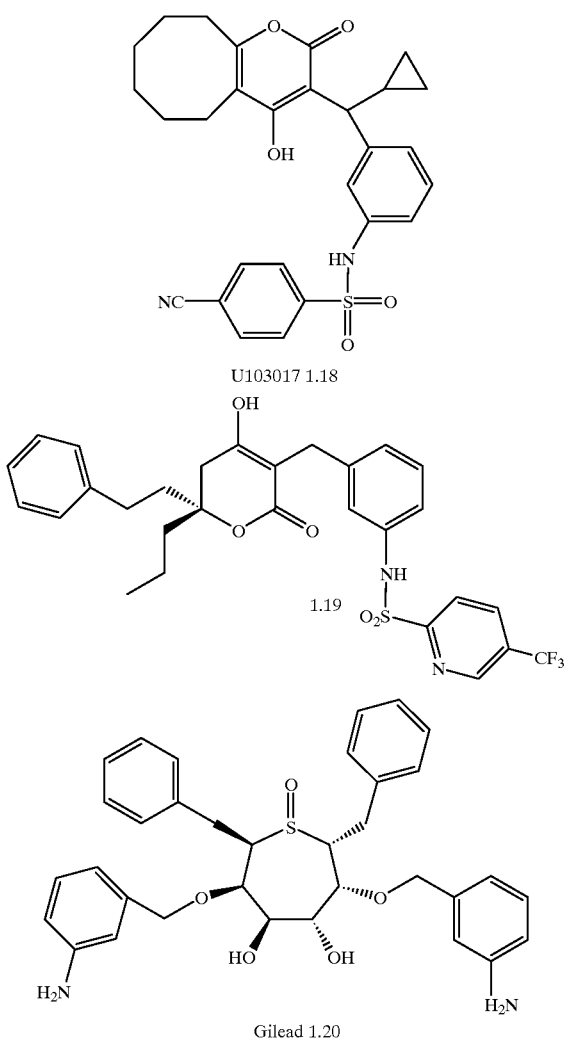

SUMMARY OF THE INVENTION

In a first embodiment, the invention is directed to non-immunosupressive cyclosporins comprising a cyclic undecapeptide of Formula I:

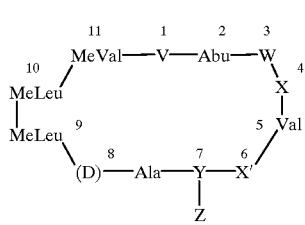

Formula (I)

wherein V is a MeLeu(3-OH), MeLeu, MeSer, MeSer-PG, MeThr, or MeThr-PG residue; W is a (D)-N-methyl-amino acid residue (or N-methylglycyl, which is non-chiral), preferably (D)-N-methylserinyl, or (D)-N-methylserinyl-PG, wherein each PG is, independently, a side-chain protecting group; X and X' are independently an N-methyl-leucinyl or an N-methylalanyl residue; Y is a lysyl, homo-lysyl, ornithinyl, lysyl-PG, homo-lysyl-PG, or ornithinyl-PG residue, wherein each PG is, independently, a side-chain protecting group; and Z is absent or is an HIV protease inhibitor moiety conjugated to Y via a side-chain on Y; and salts thereof.

In the preferred embodiments, V is a MeLeu(3-OH) residue, W is a (D)-N-methylserinyl residue, X and X' are N-methyl-leucinyl residues, Y is a lysyl residue, and Z is selected from the group consisting of:

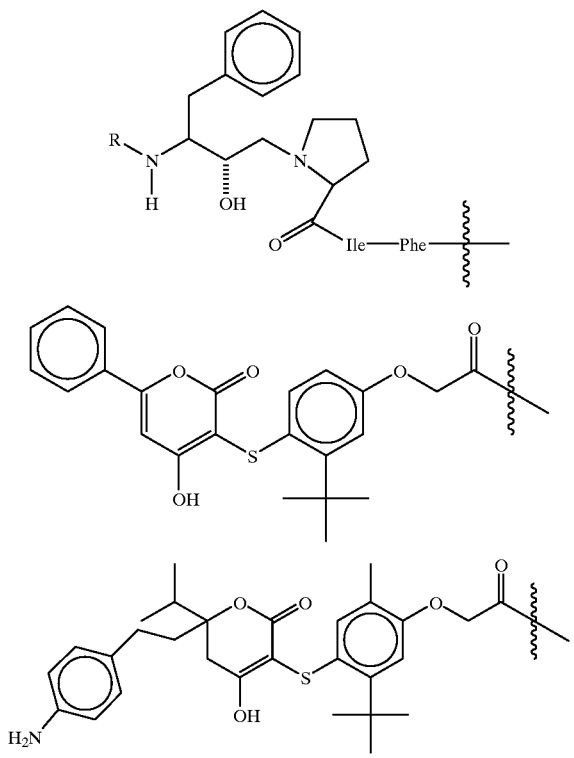

and

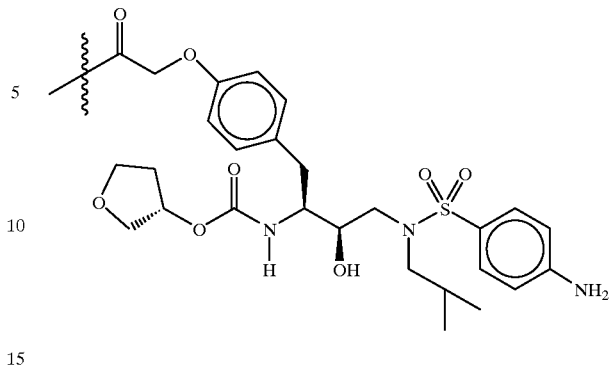

wherein R is Ac-Ser-Leu-Asn or Cbz-Asn.

In a second embodiment, the invention is also drawn to pharmaceutical compositions for the prevention and treatment of HIV-mediated disorders, including AIDS, in humans. The pharmaceutical compositions contain an effective HIV protease-inhibiting amount of one or more of the Formula I compounds or pharmaceutically-acceptable salts of the compounds. The preferred pharmaceutical composition contains the Formula I compound wherein W is a (D)-N-methylserinyl residue, X and X' are N-methyl-leucinyl residues, Y is a lysyl residue and Z is

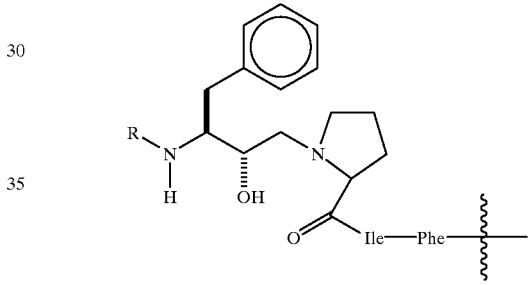

wherein R is Cbz-Asn.

A third embodiment of the invention is drawn to a method of treating HIV-mediated disorders, including AIDS, in humans. The method comprises administering to a human subject in need thereof an effective HIV protease-inhibiting amount of one or more compounds of Formula I, or pharmaceutically-acceptable salts thereof.

A fourth embodiment of the invention is directed to a compound comprising a conjugate which is produced by forming a cyclosporin analog comprising a lysyl residue having an ε-aminobutyl side-chain at 7-position of the cyclosporin analog; and then conjugating an HIV protease inhibitor to the ε-aminobutyl side-chain of the lysyl residue. These conjugates simultaneously bind to and inhibit the action of cyclophilin and HIV protease. Consequently, they are useful in the treatment of HIV-mediated disorders, including AIDS.

A distinct advantage of the present invention is that it provides novel CsA analogs which are non-immunosuppresive and which are potent inhibitors of HIV protease. These compounds are therefore highly effective inhibitors of HIV replication.

Another advantage of the invention is that it provides a generalized approach for preparing compounds which are effective to inhibit HIV protease by conjugating an HIV protease inhibitor moiety to a CsA analog having a lysyl residue in the 7-position of the cyclosporin skeleton. When conjugated to this position, the inhibitor moiety does not interfere with the ability of the CsA to bind to and inhibit the PPIase activity of the Cyp, while simultaneously enabling the conjugate to bind to and inhibit HIV protease. Because the ε-aminobutyl side-chain of the 7-position lysyl residue extends away from the CsA ring, virtually any molecule can be attached to the aminobutyl side-chain without adversely affecting the binding of the CsA analog to Cyp.

A notable benefit to this approach is that compounds which exhibit HIV protease inhibitor activity, when conjugated to the CsA analog, display increased bioavailability and cell penetration and are targeted to Cyp, an enzyme believed to play an as yet undetermined role in the replication of the HIV. This places the inhibitor moiety in a position to disrupt the HIV replication cycle by inhibiting HIV protease, while the "binding domain" of the CsA analog simultaneously binds to and inhibits Cyp.

A striking aspect of the invention which is confirmed by the National Cancer Institute screenings presented in the Examples is that the subject analogs and conjugates are taken into cells. This is remarkable because the molecular weight of the conjugates is on the order of 2,000 Da. It is commonly accepted that compounds having a molecular weight greater than about 500 Da are only poorly taken into cells. Consequently, a primary utility of the invention is to take compounds having a good anti-HIV activity, but poor bioavailability, and conjugating them to a CsA analog, thereby increasing the bioavailability and anti-HIV activity of the compound. The invention can be practiced with any anti-HIV moiety which can be conjugated to an amino moiety.

Another advantage to the compounds of the invention is that by inserting a MeLeu(3-OH) residue in the 1-position, the compounds are rendered non-immunosuppressive but maintain their anti-HIV activity.

BRIEF DESCRIPTION OF THE DRAWINGS

FIG. 1 is a graph depicting the anti-HIV activity of the compound 2.8 according to the U.S. National Cancer Institute's "In Vitro Anti-AIDS Drug Discovery Program."

FIG. 2 is a graph depicting the anti-HIV activity of compound 2.6 as determined by the same assay as in FIG. 1.

FIG. 3 is a graph depicting the anti-HIV activity of compound 2.10 as determined by the same assay as in FIG. 1.

FIG. 4 is a graph depicting the anti-HIV activity of compound 4.20 as determined by the same assay as in FIG. 1.

DETAILED DESCRIPTION OF THE INVENTION

Abbreviations and Definitions

To aid in a consistent understanding of the invention, the following abbreviations and definitions shall be used herein:

AIDS: Acquired Immune Deficiency Syndrome, as defined by the United States Centers for Disease Control.

Binding Domain of CsA: The sub-domain of cyclosporin and cyclosporin analogs which binds to cyclophilin. The binding domain generally includes residues 9-10-11-1-2 of cyclosporin.

Cyclophilin (Cyp): A ubiquitous cytosolic protein having PPIase activity. Cyclosporins bind to and inhibit the action of cyclophilin.

Cyclosporin A (CsA): As used herein, the terms "cyclosporin," "cyclosporin derivative," and "cyclosporin analog" denote any compound having the fundamental structure of cyclosporin A, namely a cyclic undecapeptide having a number of N-methyl-substituted amino acid residues, with amino acid substitutions at defined positions within the molecule.

Cyclosporin Conjugates: A CsA analog or derivative conjugated to an exocyclic moiety, especially but not exclusively at position-7 of the CsA skeleton. Cyclosporin conjugates are molecules which retain the ability to bind to cyclophilin.

Effector Domain of CsA: In unmodified CsA, the sub-domain which binds to calcineurin. Generally includes residues 4-5-6-7-8 of the CsA molecule. In CsA analogs and conjugates, the effector domain is the region of the CsA skeleton where various anti-HIV substituents are attached to the CsA molecule to alter the specificity of the CsA analog or conjugate.

Human Immuno-Deficiency Virus (HIV): Any of a class of virus which are believed to be causative of AIDS in man.

HIV protease: HIV protease is an aspartic protease that cleaves the immature viral protein gag-pol into mature structural proteins and enzymes. HIV protease is an essential enzyme in the replication of the HIV virus.

HIV protease inhibitor: Any compound now known or developed in the future which inhibits or prevents the action of HIV protease, thereby inhibiting or preventing the replication of HIV.

Modified Residues, Reagents, Protecting Groups, and Solvents: Abu=$\alpha$-aminobutyric acid, Bn=benzyl, Boc=t-butoxycarbonyl, BOP=benzotriazolyl-N-oxy-tris (dimethylamino)phosphonium hexaflurophosphate BOP-Cl=bis(2-oxo-3-oxazolidinyl phosphonic chloride, Cbn=benzylcarbonyl, Cbz=benzyloxycarbonyl, DCC=dicyclohexyl carbodiimide, DCM=dichloromethane, DCU=dicyclohexylurea, DIBAL=diisobutylaluminum hydride, DIEA=diisopropylethylamine, DIPCDI=diisopropylcarbodiimide, DMAP=4-dimethylaminopyridine, DMF=dimethylformamide, EthOAc=ethylacetate, FABMS=Fast Atom Bombardment Mass Spectrometry, Fmoc=9-fluorenylmethoxycarbonyl, HATU=O-(7-azabenzotriazol-1-yl)-1,1,2,2-tetramethyluronium hexafluorophosphate, HEA=hydroxyethyl amine, HOBt=1-hydroxybenzotriazole, LAH=lithium alumunium hydroxide, MeLeu(3-OH)=3-hydroxy-N-methyl-leucine, MTBE=methyl-t-butyl ether, NMM: N-methylmorpholine, NMP=N-methyl pyrrolidinone, OBn=benzyloxy, OTBS=t-butyldimethylsilyloxy, PyAOP=7-azabenzotriazole-1-yl oxytris (pyrodidino) phosphonium hexafluorophosphate, Sar=sarcosine, TBAF=tetrabutylammonium fluoride, TBS=t-butyldimethylsilyl, TBS-Cl=t-butyldimethylsilyl chloride, TEA=triethyl amine, TFA=trifluoroacetic acid, THF=tetrahydrofuran, TMS=tetramethylsilyl, TLC=thin layer chromatography, Trt=trityl (i.e., triphenylmethyl).

Peptidyl prolylisomerase (PPIase): The functional class of enzymes to which cyclophilin belongs. PPIase catalyzes the cis-trans conversion of Xaa-Pro bonds.

Overview

The invention is drawn to CsA analogs and conjugates which simultaneously bind to cyclophilin and HIV protease in a biological system. In particular, the invention encompasses a class of CsA analogs in which amino acid substitutions have been made at the 1, 3, and 7-positions of the CsA skeleton. By judiciously altering the structure of natural CsA, the CsA analogs described herein are non-immunosuppresive and strongly inhibitory of HIV replication as shown in a standard, widely-accepted assay (see the Examples).

The invention is also drawn to conjugates of these CsA analogs. In its most general approach, the invention is drawn to conjugating an HIV protease inhibitor to a residue within the effector domain of the CsA skeleton, preferably the residue at position-7. This allows the HIV protease moiety to be exposed to solution, even when the binding domain of the CsA molecule is joined to Cyp. Because Cyp is believed to play a role in HIV replication, conjugating an HIV protease inhibitor moiety to the effector domain of CsA disposes the inhibitor in close proximity to the HIV virion during replication (or likewise disposes the non-immunosuppresive CsA analog in close proximity to the HIV virion during replication), thereby increasing its ability to inhibit the replication process.

Additionally, because endogenous Cyp levels are much higher than HIV protease levels in infected cells, higher levels of the conjugated HIV protease inhibitor are attainable than are using the isolated protease inhibitor itself. This further aids in inhibiting HIV replication.

While not being limited to any particular molecular mechanism, it is believed that the conjugates assert their anti-HIV action by simultaneously binding to and inhibiting both Cyp and HIV protease.

What follows is a description of the chemical reactions by which the CsA analogs and conjugates are made, followed by a description of incorporating the analogs and conjugates into pharmaceutical compositions for the treatment of HIV-mediated disorders. The "Examples" section includes illustrative synthetic protocols and third party-generated data showing the anti-HIV activity of the compounds.

Chemistry

Synthesis of (2S,3R)-MeLeu(3-OH)

Route 1: The first route to (2S,3R)-MeLeu(3-OH), is based on a (2R,3R)-Leu(3-OH) synthesis reported by Evans et al (1987), *Tetrahedron Lett.,* 28:39 uses a boron enolate mediated Evans aldol reaction and an efficient epimerization of a cis- to trans-oxazolidonone as the key steps (Scheme 3.3). Boron triflate-mediated condensation of the bromoacetyl chiral auxiliary 3.7, obtained from the chiral auxiliary in 82% yield, with isobutrylaldehyde yielded the aldol product 3.8 in 50% yield.

Scheme 3.3.
Synthesis of intermediate carbamate 3.9 using an Evans aldol Reaction 3.7

-continued 3.8

3.9

Reaction of the methylisocyanate with 3.8 catalyzed by $BF_3OEt_2$, produces the carbamate 3.9 in 80% yield. Removal of the chiral auxiliary with LiOH and cyclization of the carbamate with tert-butoxide gives the cis-oxazolidinone 3.10 in 74% yield (Scheme 3.4). Reaction of acid 3.10 with TMS-diazomethane gives the cis-oxazolidinone methyl ester 3.11, which is efficiently epimerized to the desired trans-oxazolidinone acid 3.12 with KOH/ethanol and then hydrolysed to (2S,3R)-MeLeu(3-OH) 3.6 with KOH(aq) in 73% overall yield. Although this chiral synthesis of (2S,3R)-MeLeu(3-OH) requires fewer purification steps and affords easy isolation of intermediates, the mass of the chiral auxiliary made scaling up impractical on >0.5 g reactions.

Scheme 3.4.
Synthesis of 2S,3R MeLeu(3-OH) 3.6 using an Evans Aldol Reaction 3.9

3.10

3.11

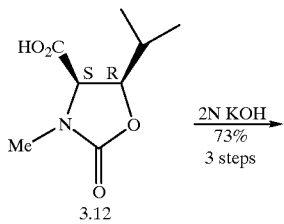

3.12

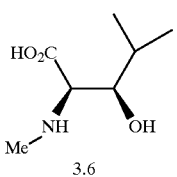

3.6

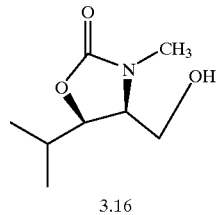

3.16 a see Scheme 3.7 for conditions

Scheme 3.6.
Synthesis of 2S,3R MeLeu(3-OH) 3.6 using the Sharpless asymmetric epoxidation reaction.

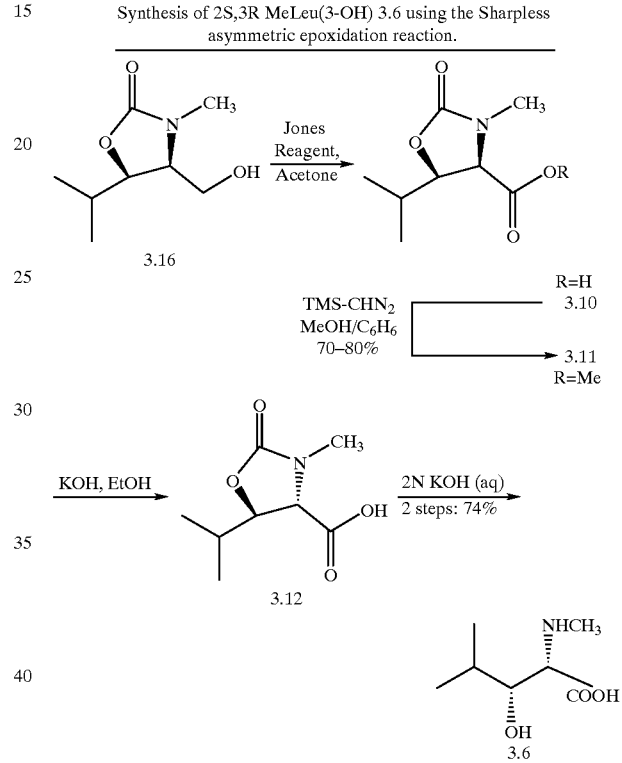

Route 2

Synthesis of (2S,3R)-MeLeu(3-OH)

A second synthesis of (2S,3R)-MeLeu(3-OH) was developed based on a Leu(3-OH) synthesis (all 4 isomers) reported by Omura et al. (1993), *Tetrahedron Lett.* 34:4447; and (1996), *J. Am. Chem. Soc.* 118:3584. The Sharpless asymmetric epoxidation reaction is used to set the stereocenters and the cis to trans-oxazolidinone epimerization described in Route 1 is used to produce the correct stereochemistry of the final product (Scheme 3.5). The α,β-unsaturated ester 3.13 is reduced with DIBAL to the allylic alcohol 3.14, which is epoxidized using D-diethyl tartarate to yield the epoxy alcohol 3.15 in good yield. Treatment of 3.15 with NaH and MeNCO at reflux produces a mixture of oxazolidinone isomers, some decomposition products, and only a low yield of the desired oxazolidinone 3.16. Oxidation of the alcohol 3.16 with a Jones reagent gives acid 3.10, which is treated with TMS-diazomethane to give the methyl ester 3.11 in 70% overall yield (Scheme 3.6). Epimerization and hydrolysis of the (2R,3R) methyl ester 3.11 with KOH/ethanol gives (2S,3R) oxazolidinone acid 3.12, which is not isolated, but hydrolysed directly with KOH(aq) to the desired (2S,3R)-MeLeu(3-OH) 3.6.

Scheme 3.5.
Synthesis of 2R,3R oxazolidinone 3.16 using the Sharpless asymmetric epoxidation reaction.

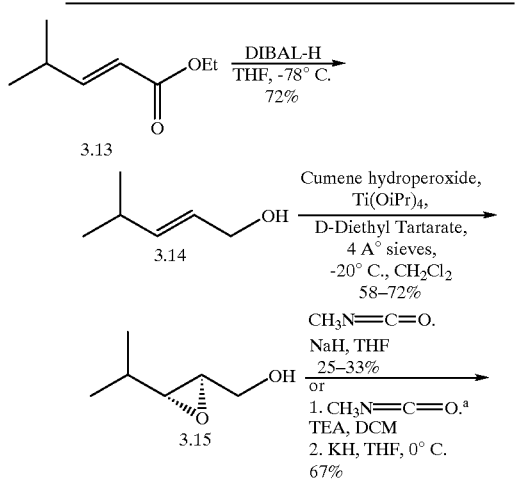

Optimized Route to Oxazolidinone 3.16.

The synthesis of (2S,3R)-MeLeu(3-OH) in Scheme 3.5 is not optimal in that the conversion of the epoxy alcohol 3.15 to the desired oxazolidinone isomer 3.16 proceeds in consistently low yields. This is overcome by pre-forming the carbamate before oxazolidinone formation, by using a stronger base in the oxazolidinone isomerization step, and by varying the reaction temperature (Scheme 3.7). Treatment of the epoxy alcohol 3.15 with Et₃N and MeNCO produces the epoxy carbamate 3.17 in excellent yield. Reaction of the carbamate 3.17 with NaH/THF at reflux yields the desired oxazolidinone 3.16, in the same yield as the one-pot reaction. KH, a stronger base than NaH, causes significantly larger amounts of decomposition at reflux temperatures. It was found that treatment of the epoxycarbamate 3.17 with 1.5 equivalents of KH at 0° C. for 1 hour, followed by warming to room temperature for 2 hours gives an 85% yield of the products with a 4:1 ratio of the desired oxazolidinone 3.16 isomer to the undesired oxazolidinone 3.18. Thus, a novel synthesis of (2S,3R)-MeLeu(3-OH) has been achieved by use of the Sharpless assymmetric epoxidation, followed by oxazolidinone isomerization with KH, and oxazolidinone epimerization to the desired trans-oxazolidinone. This synthesis is rapid, requires few purification steps, and facilitates the large scale synthesis of (2S,3R)-MeLeu(3OH) for incorporation into CsA analogs.

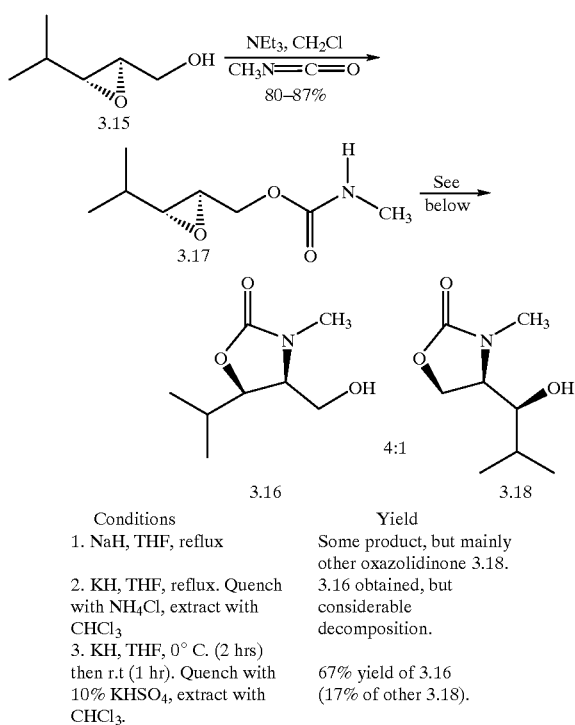

Scheme 3.7.
Optimization of oxazolidinone isomerization reaction to form 3.16.

| Conditions | Yield |
|---|---|
| 1. NaH, THF, reflux | Some product, but mainly other oxazolidinone 3.18. |
| 2. KH, THF, reflux. Quench with NH$_4$Cl, extract with CHCl$_3$ | 3.16 obtained, but considerable decomposition. |
| 3. KH, THF, 0° C. (2 hrs) then r.t (1 hr). Quench with 10% KHSO$_4$, extract with CHCl$_3$. | 67% yield of 3.16 (17% of other 3.18). |

Synthesis of CsA Analogs

The synthesis of the CsA analogs follows the modified Wenger procedure reported by Colucci et al. (1990), *J. Org. Chem.* 55:2895 (Scheme 4.1). Notable parts of the synthesis include the undecapeptide cyclization between the Ala[7]-DAla[8] residues, the "7+4" (1–7 residues+8–11 residues) segment coupling to produce the undecapeptide, and use of BOP-Cl reagent for peptide couplings. (See "Wenger's CsA Strategy.")

Cyclization between the alanines encounters the least steric bulk, no N-methylated residues, and an intramolecular hydrogen bonding pattern that may facilitate cyclization. The improved cyclization procedure involves simultaneous double deprotection of the Fmoc-protected N-terminus and the benzyl ester-protected C-terminus of the undecapeptide with NaOH(aq)/ethanol. The undecapeptide is formed via a "7+4" segment coupling so that the valuable β-OH amino acid (MeBmt[1]-(2S,3R) or MeLeu(3-OH)[1]) can be incorporated late in the synthesis. Undecapeptide formation also employs the BOP reagent which results in little epimerization of MeVal[11].

Wenger's synthesis of the "4" (8–11 position residues) segment tetrapeptide is based on an unconventional synthetic strategy in that the synthesis proceeds from the left to the right in order to avoid rapid diketopiperazine formation of the H-MecLeu-MeVal-OBn dipepetide Scheme 4.2. Tung et al. (1986), *J. Org. Chem.* 51:3350 found that by using Fmoc/tBu protection, diketopiperazine formation is inhibited so that conventional right to left synthesis proceeds without epimerization of each stereogenic center (see scheme "Strategies for synthesis of 8–11 CsA tetrapeptide"). Another major improvement over the Wenger procedure is the use of BOP-Cl for coupling of N-methyl amino acids. In his original synthesis of the 8–11 and 2–7 segments, Wenger used the mixed anhydride method, which requires low temperatures and long reaction times. The use of BOP-Cl as a N-alkyl peptide coupling reagent significantly improves the ease of CsA synthesis due to its manageable temperatures (0° C. to RT) and shorter reaction times. Thus, the combination of Wenger's overall strategy with the improved synthetic procedures described herein produces a very powerful method for generating diverse CsA analogs.

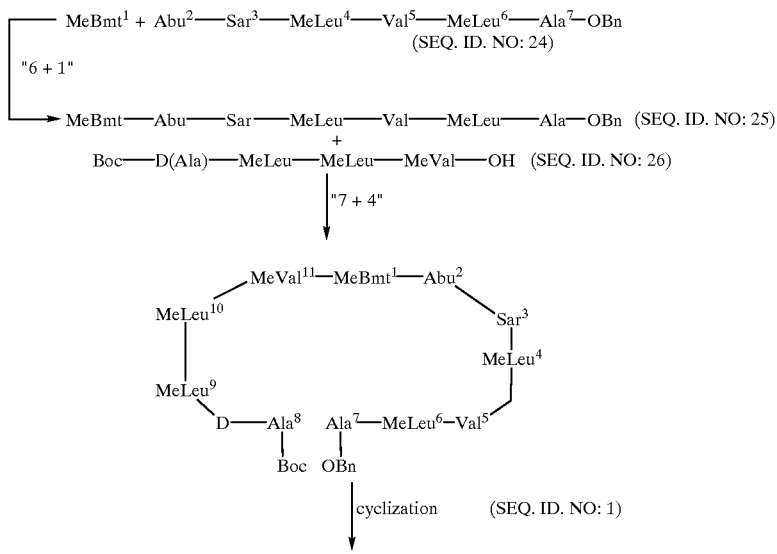

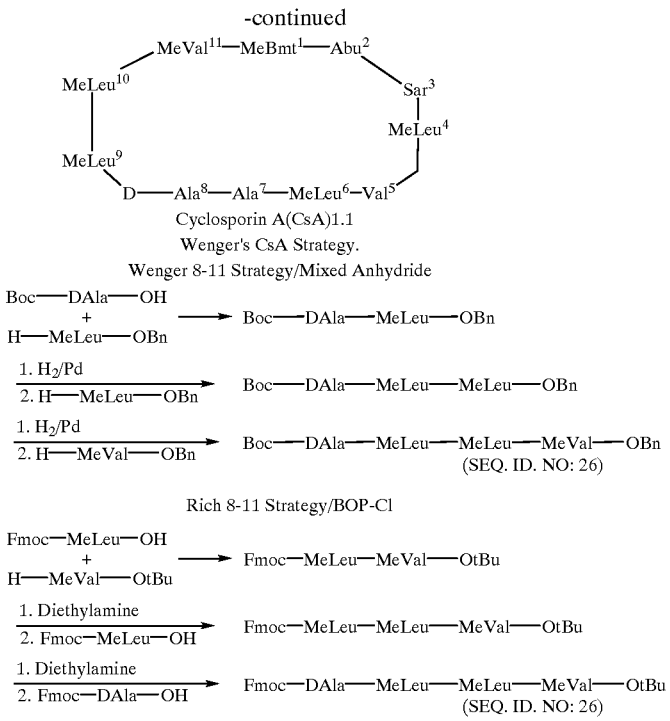

Cyclosporin A(CsA)1.1
Wenger's CsA Strategy.

Strategies for the synthesis of 8–11 CsA tetrapeptide.

Synthesis of ([MeLeu(3-OH)$^1$, D-MeSer (OBn)$^3$, Lys(2Cl-Cbz)$^7$])CsA

The synthesis of 1, 3, and 7-position substituted CsA analogs follows the procedure reported by Colucci et al (Scheme 4.1), modified so that the 2–7 segment is synthesized linearly (Scheme 4.1) and not in a "4+2" fashion due to problems with epimerization. When the 2–3 dipeptide with D-MeSer(OBn) in the 3-position is coupled to the CsA 4–7 tetrapeptide, significant epimerization if the D-MeSer) OBn) residue was observed (Scheme 4.2). Wenger attempted to synthesize the 2–7 CsA sequence linearly, but was unsuccessful due to rapid dikepiperazine formation of the Sar$^3$-MeLeu$^4$ fragment. However, we were able to synthesize the D-MeSer(OBn)$^3$2–7 CsA peptide linearly without any observed diketopiperazine formation. Furthermore, Seebach et al. (1993), *Helv. Chim. Acta.* 76:1564, has also reported a successful linear synthesis of a 2–7 CsA analog with MeAla in the 3-position.

Lys($\epsilon$N-2Cl-Cbz)$^7$ and D-MeSer(OBn)$^3$ side-chain protection was chosen because both protecting groups survive the acidic conditions required for the CsA analog synthesis, and because hydrogenation cleaves both groups without decomposing the CsA analog. Furthermore, hydrogenation of the Lys($\epsilon$N-2Cl-Cbz)$^7$ produces a free amine which is used as a "handle" to attach other compounds to the CsA analog.

Synthesis of 2–7 Peptide:

Scheme 4.1.
Synthesis of (2-7) hexapeptide 4.5 precursor of [MeLeu(3-OH)$^1$, DMeSer(OBN)$^3$, Lys(2Cl-Cbz)$^7$]CsA.

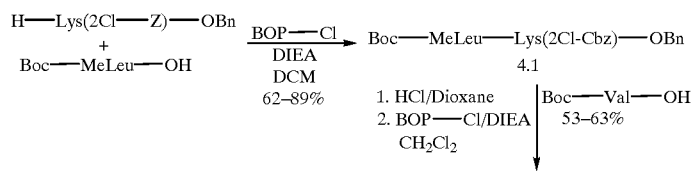

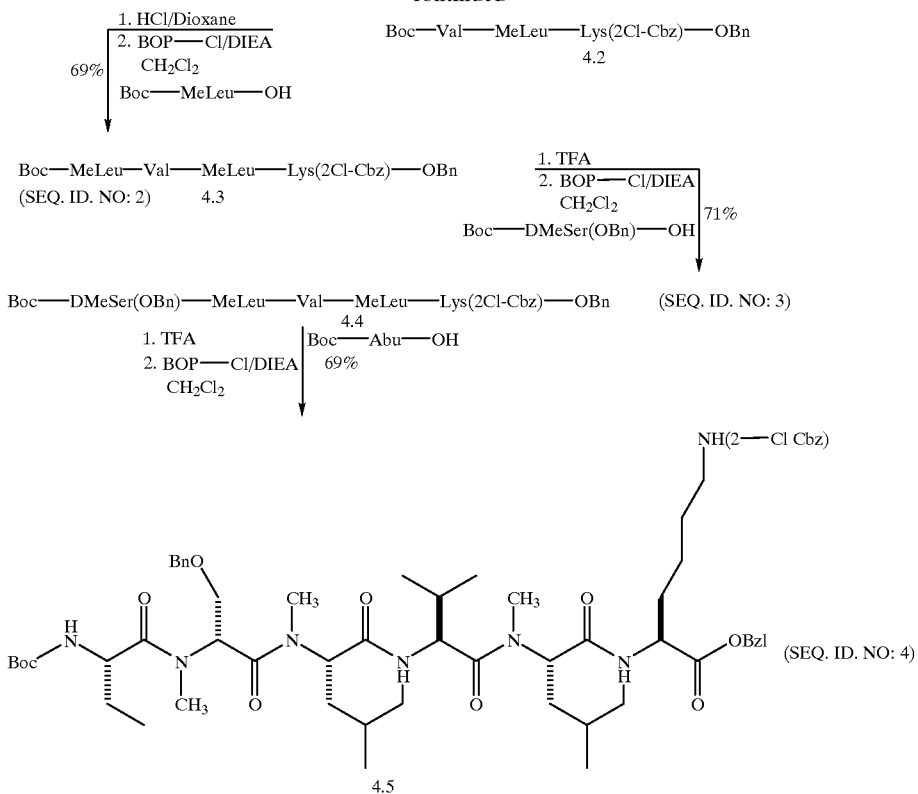

Boc-MeLeu-OH was coupled with H-Lys(2Cl-Z)-OBn to yield dipeptide 4.1 on good yield (Scheme 4.1). Cleavage of the Boc group from 4.1 with HCl/dioxane followed by reaction with Boc-Val-OH gives the tripeptide 4.2 in fair yield consistent with yields reported by Colucci et al for coupling to Boc-Val-OH. Deprotection of 4.2 and coupling with Boc-MeLeu-OH produces the 4–7 tetrapeptide 4.3 in 69% yield. Treatment of tetrapeptide 4.3 with TFA to cleave the Boc group, neutralization of the salt with NaHCO₃, followed by coupling to Boc-D-MeSer(OBn)-OH produces 4.4 in 71% yield. Cleavage of the Boc group from 4.4, neutralization and coupling to Boc-Abu-OH with BOP-Cl produces the hexapeptide 4.5 in 69% yield. No detectable epimerization of diketopiperazine formation is observed for this step. When a "4+2" coupling between Boc-Abu-D-MeSer(OBn)-OH+H-Meleu-Val-MeLeu-Lys(2Cl-Z)-OBn is attempted, significant epimerization of the D-MeSer(OBn) residue occurrs as expected for an acyl-peptide coupling (Scheme 4.2).

Scheme 4.2. Epimerization of DMeSer(OBn)₃ in "4 + 2" coupling.

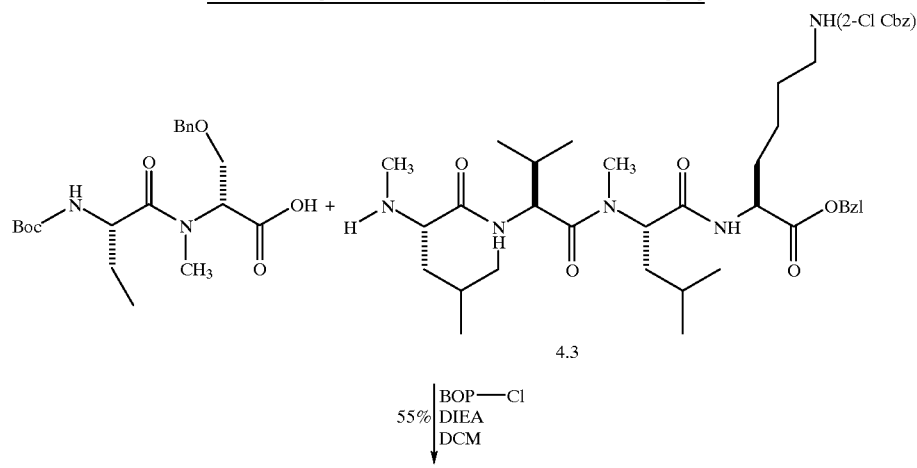

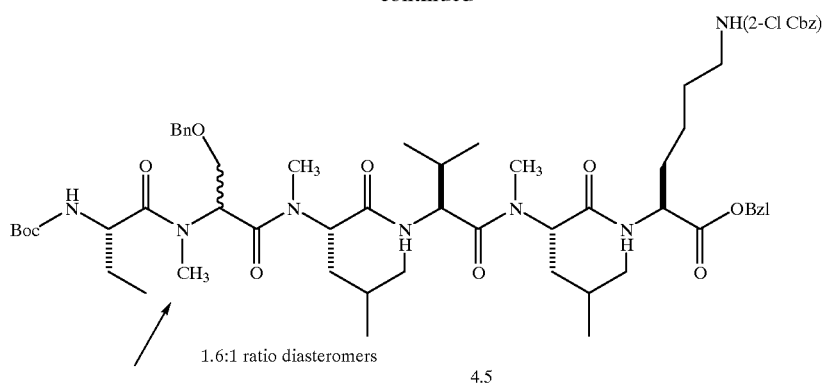
1.6:1 ratio diasteromers
4.5
20
Completion of CsA Analog
Scheme 4.3.
Synthesis of undecapeptide 4.9 precursor of [MeLeu(3-OH)¹, DMeSer(OBN)³, Lys(2Cl-Cbz)⁷]CsA.
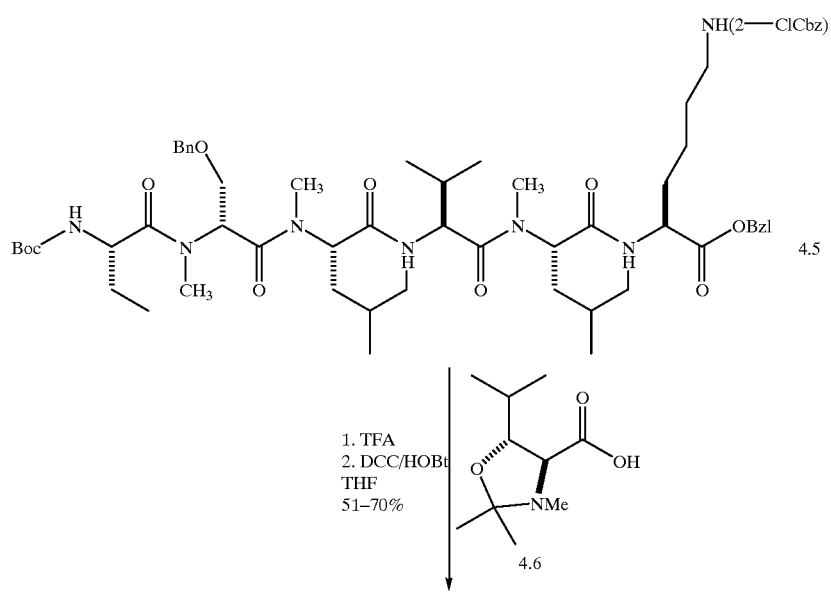

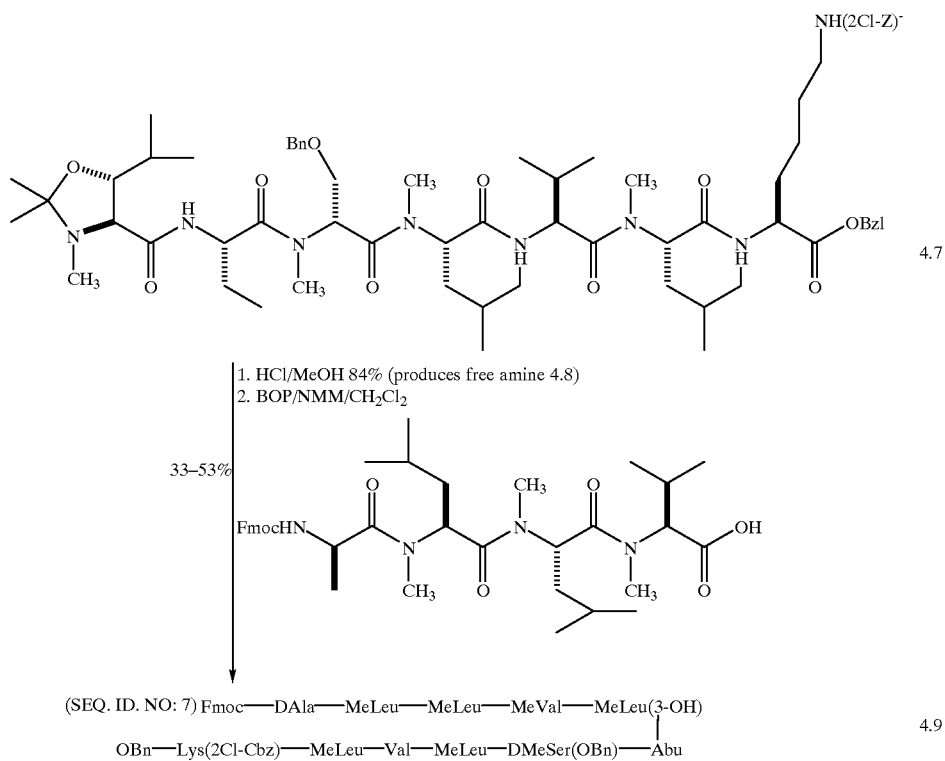

4.7

1. HCl/MeOH 84% (produces free amine 4.8)
2. BOP/NMM/CH$_2$Cl$_2$

33–53%

4.9

(SEQ. ID. NO: 7) Fmoc—DAla—MeLeu—MeLeu—MeVal—MeLeu(3-OH)
OBn—Lys(2Cl-Cbz)—MeLeu—Val—MeLeu—DMeSer(OBn)—Abu The final stages of the CsA analog synthesis follows the procedure first developed by Wenger, supra. The 2–7 hexapeptide 4.5 is coupled to the acetonide-protected MeLeu(3-OH) 4.6 with EDCI/HOBt to yield the 1–7 heptapeptide 4.7 in yields of 51–70% (Scheme 4.3). Cleavage of the acetonide with standard HCl(aq) conditions and neutralization of the HCl salt with NaHCO$_3$ gives 4.8, which is coupled to the 8–11 tetrapeptide with the BOP reagent to produce the undecapeptide 4.9 in 33–53% yield. Simultaneous cleavage of the Fmoc and benzyl ester groups with NaOH(aq)/ethanol followed by cyclization of the linear undecapeptide with DMAP/Propyl phosphonic anydride in CH$_2$Cl$_2$ gives (MeLeu(3-OH)$^1$, D-MeSer(OBn)$^3$, Lys(2Cl-Cbz)$^7$)CsA 4.10 in fair to good yields of 30–60% (Scheme 4.4).

Scheme 4.4.
Undecaptide cyclization to form [MeLeu(3-OH)$^1$, (DMeSEr(OBn)$^3$, Lys(2Cl-CBz)$^7$]CsA 4.10/

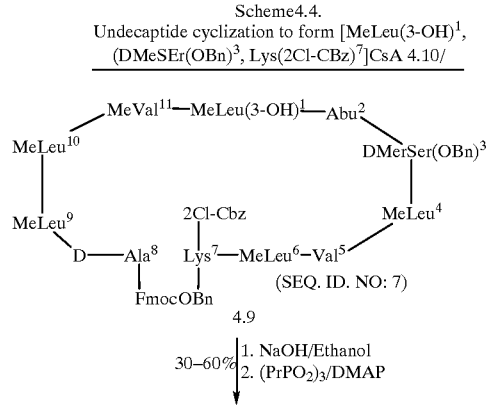

(SEQ. ID. NO: 7)
4.9

30–60% 
1. NaOH/Ethanol
2. (PrPO$_2$)$_3$/DMAP

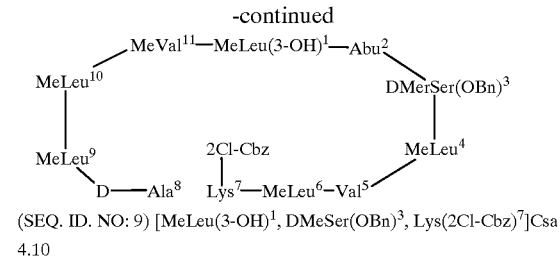

(SEQ. ID. NO: 9) [MeLeu(3-OH)$^1$, DMeSer(OBn)$^3$, Lys(2Cl-Cbz)$^7$]Csa
4.10

Synthesis of (MeLeu(3-OH)$^1$, D-MeSer (OH)$^3$, Lys (2Cl-Cbz)$^7$)CsA

Scheme 4.6.
Synthesis of 3-7 pentapeptide 4.14 precursor of [MeLeu(3-OH)$^1$, DMeSer(OH)$^3$, Lys(2Cl-Cbz)$^7$]CsA.

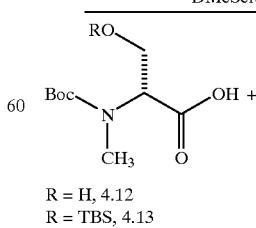

R = H, 4.12
R = TBS, 4.13

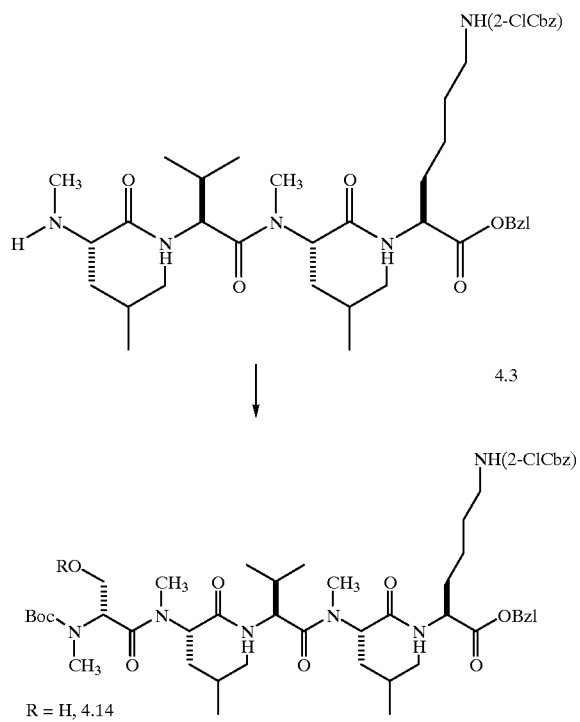

| Product | Conditions | yield |
|---|---|---|
| 4.14 | BOP—Cl | 37% |
| 4.14 | HOAT/DIPCDI | 49%[a] |
| 4.14 | HATU | 26–37% |
| 4.15 | BOP—Cl | 58–65% |

[a] product contaminated with urea formed during the reaction

The Boc group is cleaved from tetrapeptide 4.3, and the resulting free amine HCl salt is coupled to Boc-D-MeSer-OH 4.12 with BOP-Cl, to give the desired pentapeptide 4.14 (Scheme 4.6). Other coupling reagents, such as HATU or DIPCDI/HOAT can also be used (Scheme 4.6). Temporary hydroxyl protection, which is cleaved after pentapeptide formation, improves the yield of product and the ease of purification. To this end, Boc-D-MeSer(OTBS-OH 4.13 is smoothly coupled to the tetrapeptide 4.3 with BOP-Cl to give pentapeptide 4.15 in 65% yield (Scheme 4.6). The TBS group was cleaved from pentapeptide 4.15 with TBAF/THF in 70% yield, or with mild HF/pyridine treatment in 90% yield to give 4.24 (Scheme 4.7). Removal of the Boc group from pentapeptide 4.14 with TFA, followed by neutralization of the TFA salt with $NaHCO_3$, gives a free amine which is coupled with Boc-Abu-OH to give the desired hexapeptide 4.16 in 68% yield.

The Boc group is removed from hexapeptide 4.16, neutralized, and coupled with the acetonide-protected MeLeu(3-OH) 4.6 to give heptapeptide 4.17 in 58–80% yield. Acetonide-protected Meleu(3-OH) is formed by refluxing MeLeu(3-OH) in acetone overnight. Cleavage of the acetonide from heptapeptide 4.17 with HCl/MeOH, followed by neutralization with $NaHCO_3$, gives the heptapeptide amine 4.18 in 58–80% yield. The heptapeptide 4.17 is then coupled with 8–11 tetrapeptide under standard conditions to give undecapeptide 4.19 in 32–50% yield (Scheme 4.8). After cyclization of the undecapeptide 4.19 with $(PrPO_2)_3$/DMAP, the CsA analog [MeLeu(3-OH)[1], D-MeSer(OH)[3], Lys(2Cl-Cbz)[7]CsA 4.20 is obtained in 41–53% yield. To allow coupling of the HIV protease inhibitor or another compound to the CsA analog, the Cbz group is cleaved with $Pd(OH)_2/H_2$ to yield the desired free amine CsA analog 4.11 in quantitative yield.

Scheme 4.7.
Synthesis of 1-7 heptapeptide 4.18 precursor of [MeLeu(3-OH)[1], DMeSer(OH)[3], Lys(2Cl-Cbz)[7]]CsA.

-continued
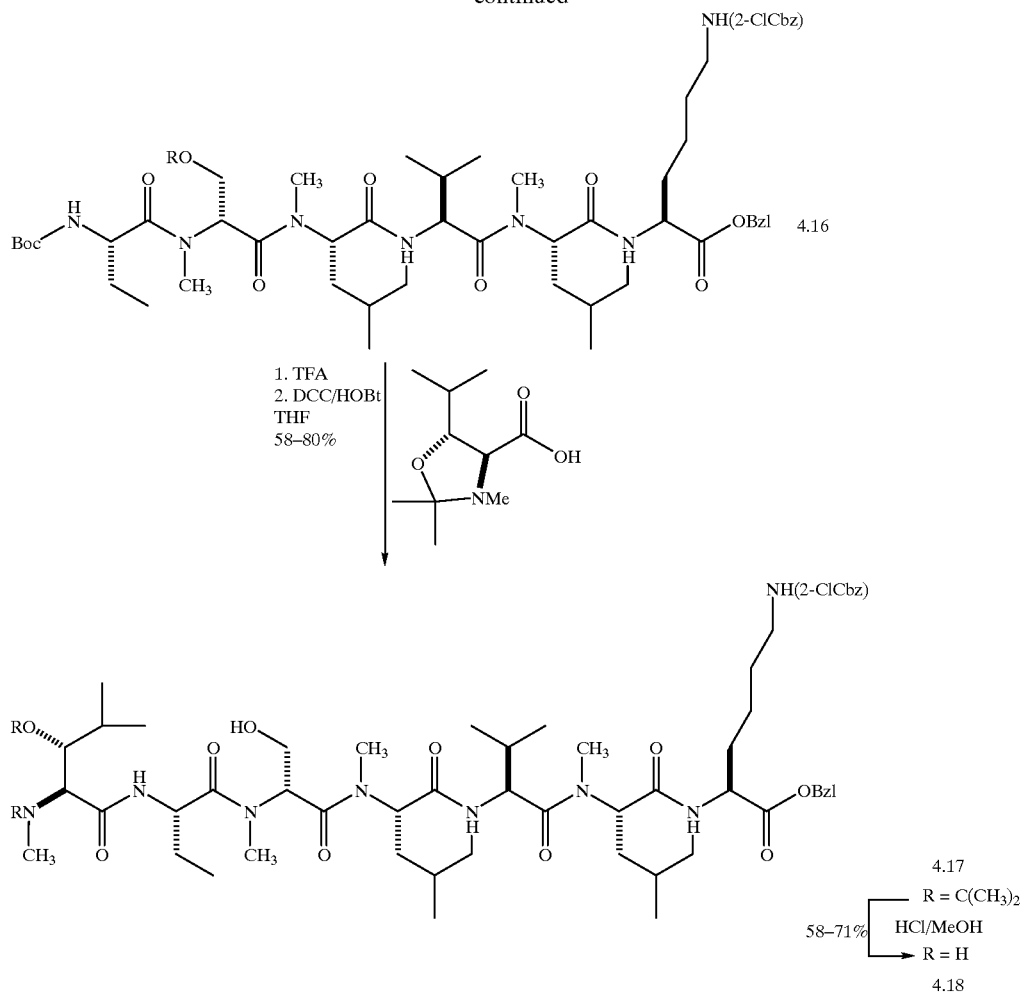
4.16
4.17
R = C(CH₃)₂
HCl/MeOH
R = H
4.18
Scheme 4.8.
Synthesis of [MeLeu(3-OH)¹, DMeSer(OH)³, Lys⁷]CsA 4.11.
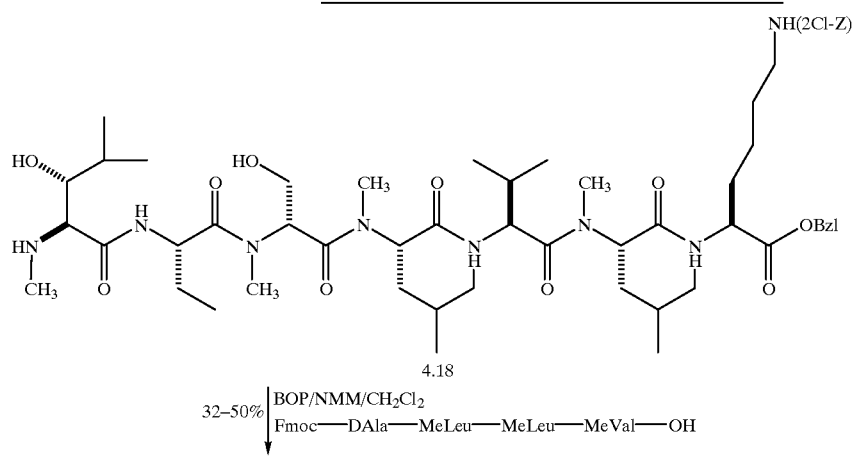

-continued

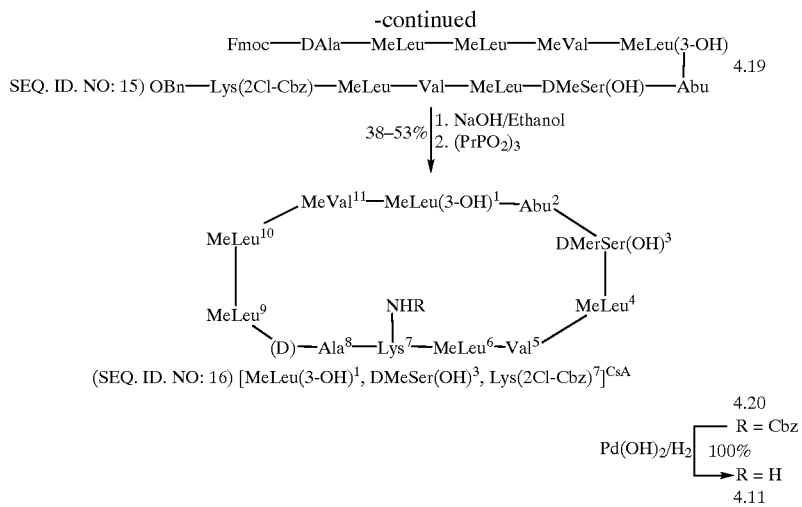

4.20
Pd(OH)₂/H₂ [ R = Cbz
100%
R = H
4.11

Synthesis of η-Hydroxycyclosporin A (OL-17) from CsA

The semisynthetic cyclosporin A derivative, OL-17 is synthesized by the procedure of Eberle and Nuninger (1992), *J. Org. Chem.* 57:2689 (Scheme 4.9). Cyclosporin A is treated with acetylchloride and DMAP to yield acetylcyclosporin A 4.21 in 65% yield. Allylic bromination with 1.2 equivalent of NBS.AIBN(cat.) in CCl₄ at reflux gives allylic bromide 4.22 which is used crude in the next reaction. As noted by Eberle and Nuninger, the bromination reaction cannot be followed by TLC because the starting material and product have identical $R_f$ values. Thus, crude allylic bromide 4.22 is dissolved in 2-butanone, treated with NMe₄OAc/cat.NaI, and the reaction is heated to 60° C. to give η-acetoxyacetyl cyclosporin A 4.23 in 47% yield after purification by flash chromatography. The bisacetate 4.23 is treated with to NaOMe to give the final product, OL-17 2.11 in 50% yield.

Scheme 4.9. Synthesis of OL-17 2.11.

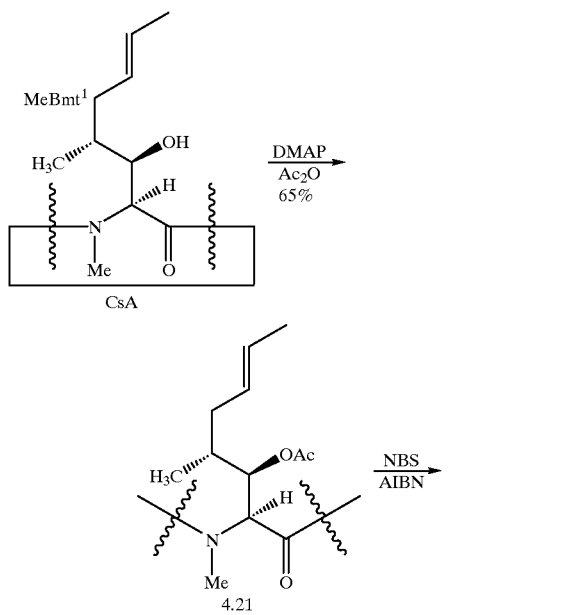

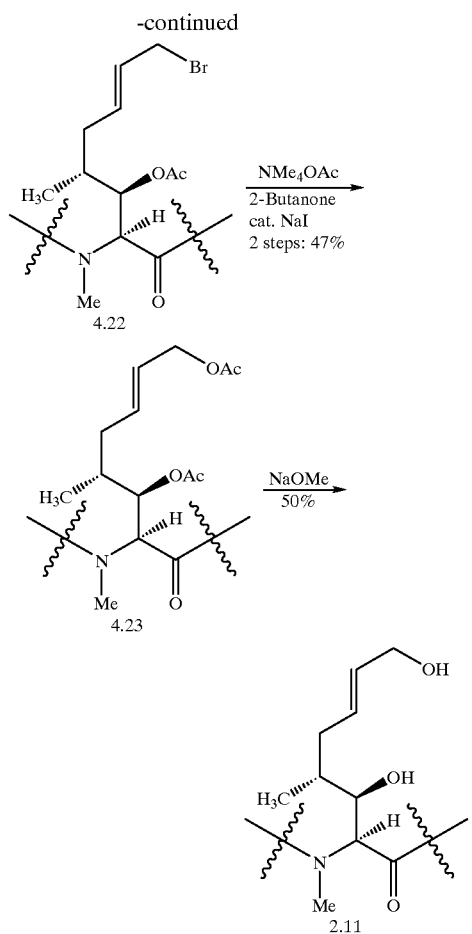

Synthesis of CS-131 Acid Analog

The synthesis of CS-131 2.2, a truncated analog of the HIV protease inhibitor JG-365 2.1, follows the procedure of Rich et al., except that the original C-terminal methyl ester is replaced with an allyl ester. Incorporation of the allyl ester into the HIV protease inhibitor permits either sanctification or palladium-mediated C-terminal deprotection prior to coupling with CsA analog. The key step in the synthesis of the allyl ester analog of CS-131 involves reaction of the (2R,3S)

Boc-Phe epoxide with the tripeptide Pro-Ile-Phe-allyl as shown in the retrosynthetic scheme (Scheme 5.1).

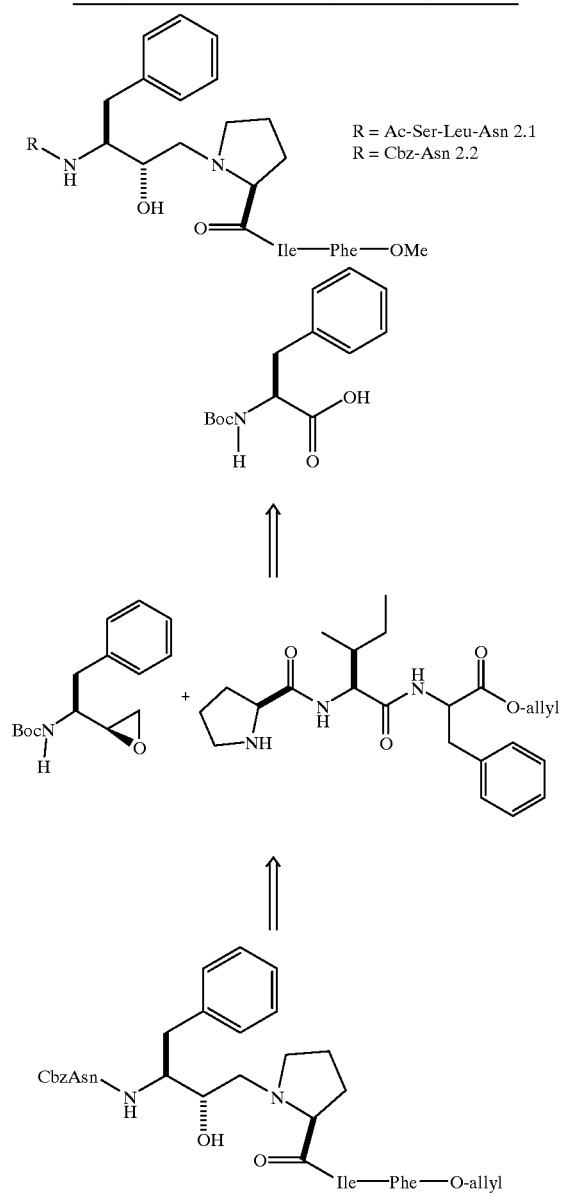

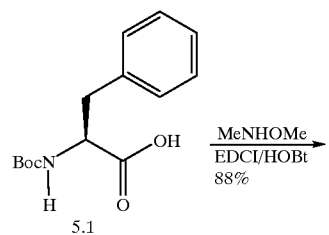

Scheme 5.1.a. Synthesis of 2R,3S Boc-Phe-epoxide 5.5.

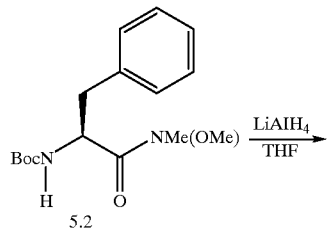

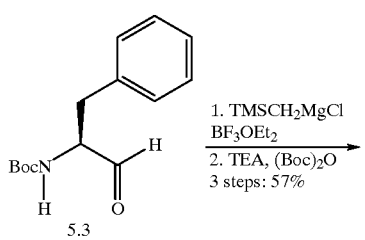

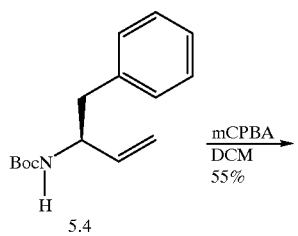

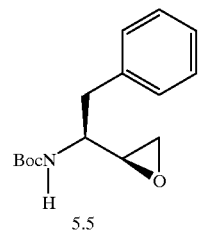

Synthesis of (2R,3S) Boc-Phe Epoxide 5.5

The key (2R,3S) Boc-Phe-epoxide is synthesized by following the procedures of Thompson et al. (1992), *J. Med. Chem.* 35;1685 and Romeo and Rich (1994), *Tetrahedron Lett.* 35:4939 (Scheme 5.1.a, above). Reaction of Boc-Phe-OH 5.1 with N,O-dimethylhydroxylamine hydrochloride and EDCI/HOBt produces the Weinreb amide 5.2 in 88% yield. Reduction of the Weinreb amide 5.2 with LiAlH$_4$ gives the aldehyde 5.3. The crude aldehyde 5.3 is converted via the Peterson olefination reaction to the alkene, which after reprotection of the amine with di-tert-butylpyrocarbonate, gives the alkene 5.4 in 57% yield. Epoxidation of the alkene 5.4 with mCPBA under the conditions of Romeo and Rich gives the desired (2S,3R) epoxide 5.5 in 55% yield.

Synthesis of CS-131 Allyl Ester Analog 5.9

The tripeptide Boc-Phe-Ile-Phe-O-allyl 5.6 is synthesized in 56% overall yield using conventional EDCI/HOBt mediated peptide couplings (Scheme 5.2). The tripeptide 5.6 is treated with HCl/dioxane and the resulting free amine HCl salt 5.7 was refluxed with epoxide 5.5 to give Boc-Phe-[HEA]-Pro-Ile-Phe-O-allyl 5.8 in 80% yield (Scheme 5.3). Cleavage of the Boc group in 5.8 with HCl/dioxane, and coupling of the resulting HCl salt with Cbz-Asn-OH to Phe-[HEA]-Pro-Ile-Phe-O-allyl with both EDCI/HOBt and Cbz-Asn-OpNP consistently gives low yields of 5.9 and complex reaction products which were difficult ro purify. Activation of Cbz-Asn-OH can cause the formation of β-cyanoalanine, but additives, such as HOBt, are known to suppress these side reactions. Additionally, incorporation of asparagine into the inhibitor decreases the solubility of the product in $CH_2Cl_2$, especially after removal of the allyl ester.

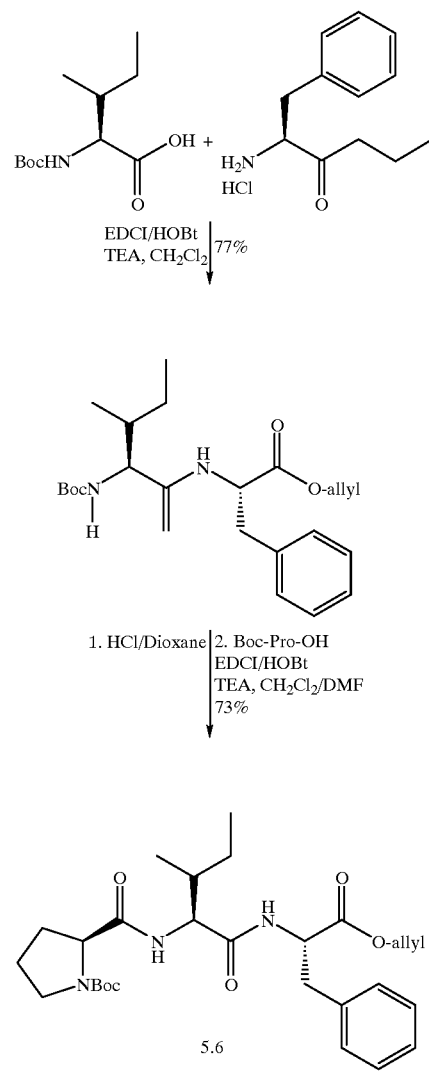

Scheme 5.2. Synthesis of Boc-Pro-Ile-Phe-O-allyl 5.6.

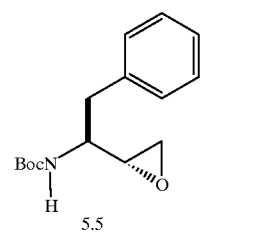

Scheme 5.3. Synthesis of allyl ester CS-131 analog 5.9.

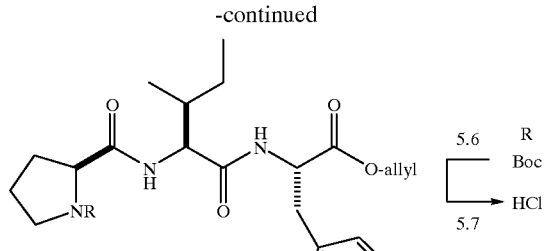

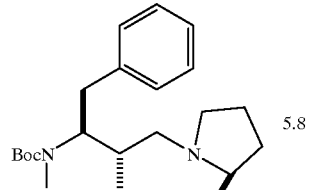

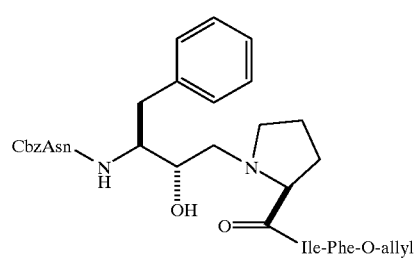

Synthesis of Trityl CS-131 Allyl Ester Analog 5.9 and CS-131 Acid 5.11

Cbz-Asn(Trt)-OH 5.10 is made using the conditions of Sieber and Riniker (Scheme 5.4). Coupling of Cbz-Asn(Trt)-OH with HCl-Phe-[HEA]-Pro-Ile-O-allyl gave 5.11 cleanly in 74% yield and was easy to purify by flash chromatography. As hoped for, the solubility characteristics of both ester 5.11 and acid 5.12 were greatly improved and facilitated conversion to the completely deprotected CS-131 derivative 5.13 (Scheme 5.5). To this end, ester 5.11 was saponified with LiOH to give 5.12, which was treated with TPA/DCM to cleave the trityl group and give completely deprotected inhibitor 5.13 in 88% yield (Scheme 5.5).

Scheme 5.4
Synthesis of allyl ester CS-131(trityl) analog 5.11

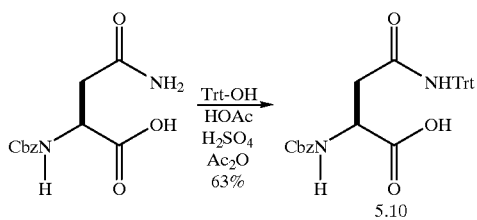

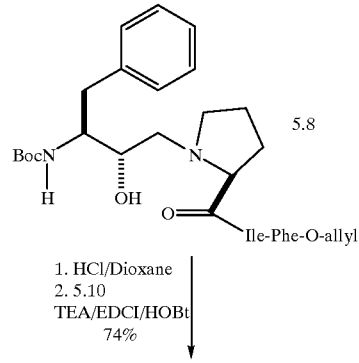

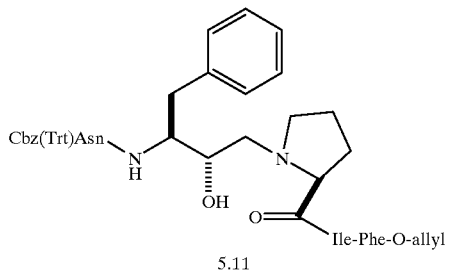

Scheme 5.5
Synthesis of CS-131 Acid 5.13

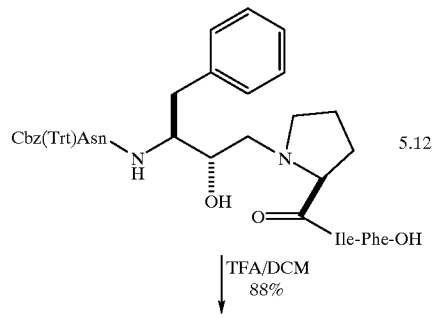

4-Hydroxypyran-2-one HIV Protease Inhibitor Synthesis

The retrosynthesis of the desired 4-hydroxypyrone inhibitor 2.4 is shown in Scheme 6.1. The inhibitor is constructed by reaction of a 6-phenyl-4-hydroxy-pyran-2-one with 2-tbutyl-4-hydroxy-benzenethiosulfonate under basic conditions in refluxing ethanol. 2-tbutyl-4-hydroxy-benzenethiosulfonate is derived from tert-butylhydroquinone via a Newman-Kwart Reaarangement followed by reaction with toluenesulfonyl bromide.

Scheme 6.1
Retrosynthetic analysis of pyrone inhibitor 2.4

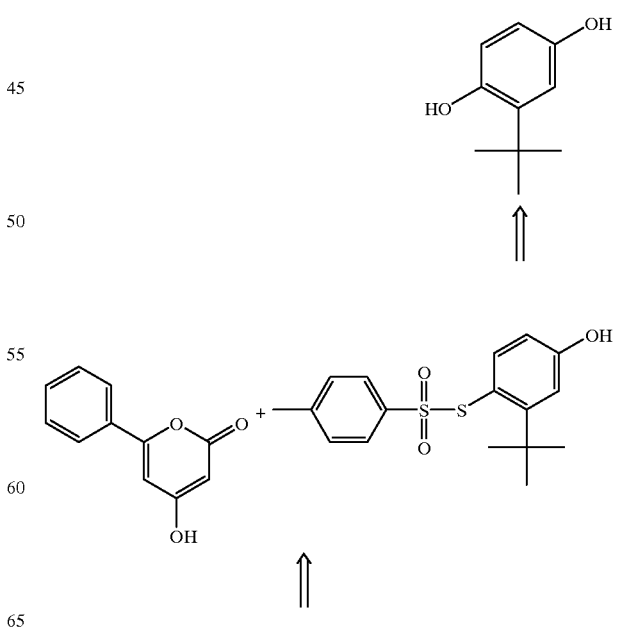

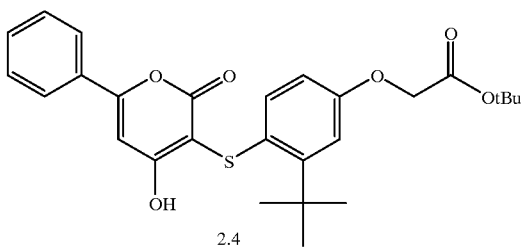

2.4

Synthesis of 2-t-butyl-4-t-butyldimethsilyhydroxy-benzenethiosulfonate 6.5

The less hindered hydroxyl group in tert-butylhydroquinone 6.1 is selectively protected as the TBS ether by reaction with TBS-Cl to give 6.2 in 88% yield (Scheme 6.1.a). Reaction of phenol 6.2 with NaH and N,N-dimethylthiocarbamoyl chloride produces the thiocarbonate 6.3 in 50% yield. Next, the Newman-Kwart rearrangement is performed by heating oxygen-linked N,N-dimethylthiocarbamate 6.3 to 275–300° C. (in a sand bath) for approximately 20 minutes to give the thiol-lonked product 6.4 in 50–70% yield (Scheme 6.2).

Scheme 6.1.a
Reaction of dimethylthiocarbamoyl chloride with TBS protected hydroquinone 6.2

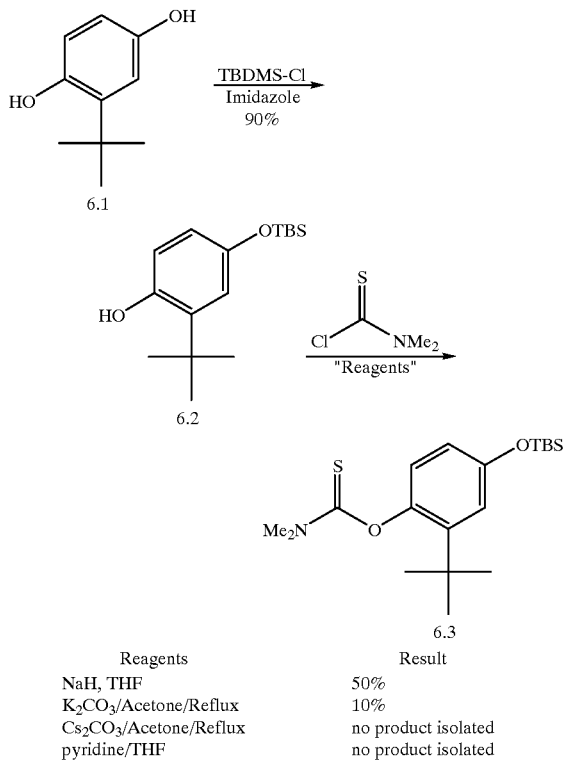

| Reagents | Result |
| --- | --- |
| NaH, THF | 50% |
| K$_2$CO$_3$/Acetone/Reflux | 10% |
| Cs$_2$CO$_3$/Acetone/Reflux | no product isolated |
| pyridine/THF | no product isolated |

Scheme 6.2
Newman-Kwart Rearrangement of TBS ether 6.3

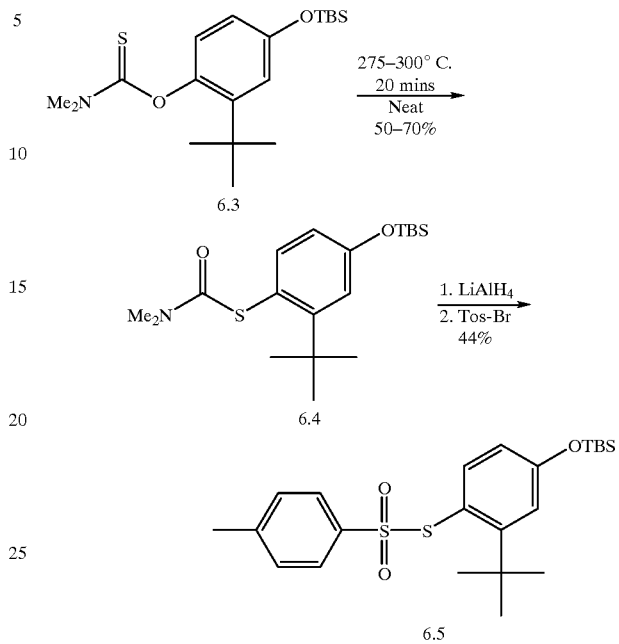

After rearrangement, the N,N-dimethylthiocarbamate 6.4 is reduced with LiAlH$_4$ to the free thiol, which is reacted with tosyl-bromide to give the desired thiosulfonate 6.5 in 44% yield (Scheme 6.2). Reaction of similar thiophenols with less reactive tosyl-chloride leads to disulfide formation, due to the unreacted thiophenol reacting with the thiosulfonate as it is produced.

Synthesis of Allyl Protected 4-hydroxypyran-2-one Inhibitor

Since the pyrone target compound 2.4 contains a carboxyl group for attaching to the CsA analog, t-butyl acetyl group was selected as a protected linker for the inhibitor. Thus, the carboxyl group could be unmasked at tie end of the pyrone inhibitor synthesis for coupling to the CsA analog.

The TBS group in 6.4 is cleaved with TBAF to give the phenol 6.9, which is reacted with NaH and t-butyl chloroacetate/TBAI to form the ester 6.10 in 97% yield (Scheme 6.6). However, attempts to saponify the N,N-dimethylthiocarbamate selectively over the t-butyl ester failed; only refluxing KOH/MeOH was able to cleave both the ester and the highly hindered thiocarbamate to give 6.12 (Scheme 6.6). All other conditions resulted in saponification of only the ester to give 6.11. The ease of the t-butyl ester saponification may be due to the small steric hindrance provided by the α-hydroxy phenyl group.

Scheme 6.6
Alkylation of phenol 6.9 and saponification of thiocarbamate 6.10

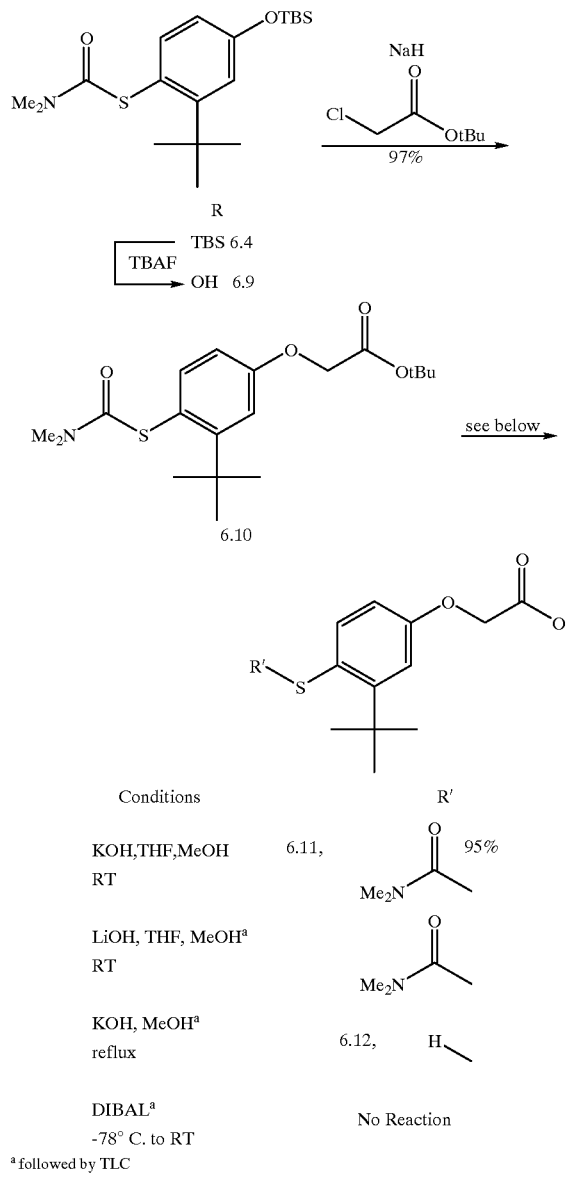

| Conditions | R' | |
|---|---|---|
| KOH,THF,MeOH RT | 6.11, Me₂N-C(O)- | 95% |
| LiOH, THF, MeOH[a] RT | Me₂N-C(O)- | |
| KOH, MeOH[a] reflux | 6.12, H- | |
| DIBAL[a] -78° C. to RT | No Reaction | |

[a] followed by TLC

To circumvent this problem, allyl ether protection was chosen for pyrone inhibitor synthesis (Scheme 6.7). After cleavage of the TBS group, the crude alcohol 6.9 is reacted with NaH/allyl iodide to give the allyl ether 6.13 in 85% overall yield. The thiocarbamate 6.13 is reduced with LiAlH₄ to give a free thiol, which is reacted crude with tosyl bromide to form the allyl protected thiosulfonate 6.14 in 44–75% yield. Finally, reaction of thiosulfonate 6.14 with pyrone 6.6, as previously described, smoothly yields the desired allyl-protected pyrone inhibitor 6.15 in 69% yield (Scheme 6.7).

Cleavage of Allyl Group From Pyrone Inhibitor 6.15

To attach the pyrone inhibitor 6.15 to a CsA derivative, the allyl ether has to be cleaved and a linking functionality installed. To cleave the allyl group, a number of palladium mediated reactions conditions were tested, but only decomposition or no reaction was observed (Scheme 6.8). The use of SnBu₃H/THF/HOAc/Pd(PPh₃)₄ reaction conditions gives a 50% yield of phenol 6.16. By switching the reaction solvent to CH₂Cl₂, the yield of 6.16 was increased to 74%. Furthermore, by using Pd(OAc)₂ and PPh₃ to form Pd(0) in situ, the reaction proceeds more consistently. Na₂CO₃ extraction, followed by washing with ether, acidification of the aqueous phase with conc. HCl, and extraction with CH₂Cl₂ provides the product in sufficient purity (>95% by ¹HNMR) to take directly on to the next reaction without further purification.

Scheme 6.7
Synthesis of allyl protected pyrone inhibitor 6.15

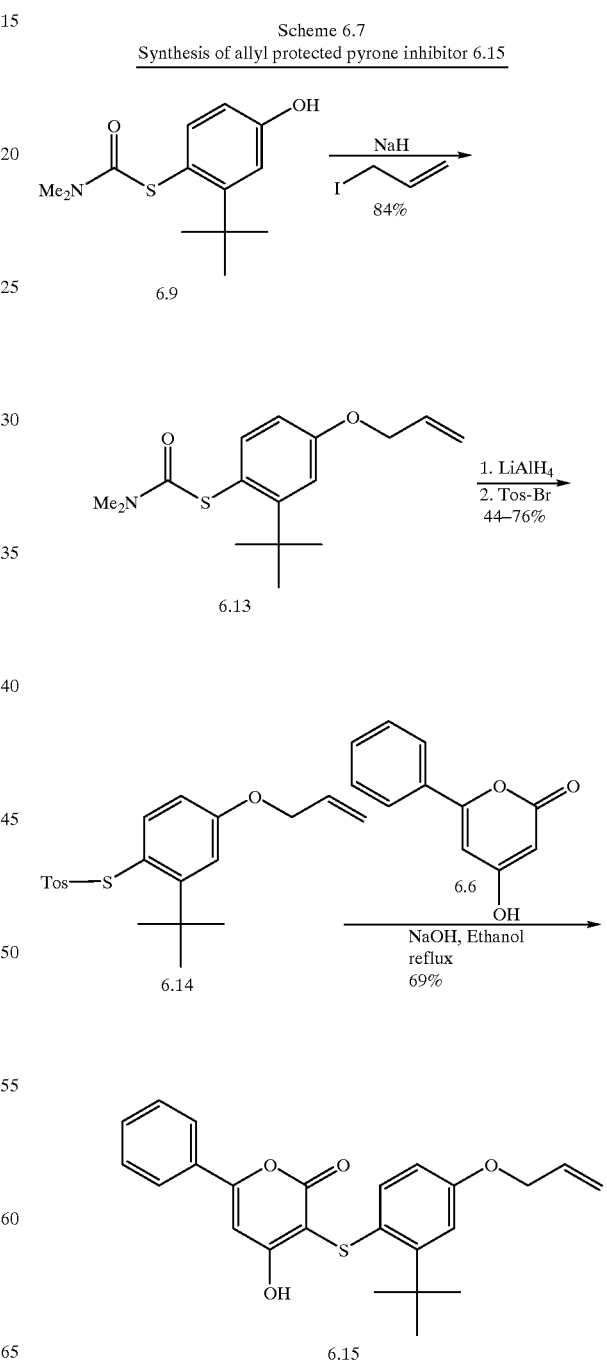

Scheme 6.8
Cleavage of allyl ether from pyrone inhibitor 6.15

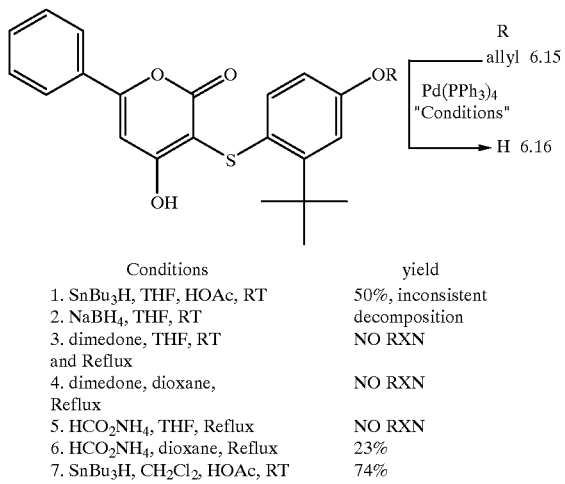

| Conditions | yield |
|---|---|
| 1. SnBu₃H, THF, HOAc, RT | 50%, inconsistent |
| 2. NaBH₄, THF, RT | decomposition |
| 3. dimedone, THF, RT and Reflux | NO RXN |
| 4. dimedone, dioxane, Reflux | NO RXN |
| 5. HCO₂NH₄, THF, Reflux | NO RXN |
| 6. HCO₂NH₄, dioxane, Reflux | 23% |
| 7. SnBu₃H, CH₂Cl₂, HOAc, RT | 74% |

Synthesis of 4-hydroxypyran-2-one Ester Inhibitor 2.4

The last step of the pyrone inhibitor synthesis requires installation of the linking functionality. Phenol 6.16 is reacted with NaH/tert-butyl chloracetate (cat.) at 0° C. followed by warming to RT overnight to give the product 2.4, some decomposition products, and mostly starting material (Scheme 6.9). Addition of tetrabutylammonium iodide (TBAI) to the reaction mixture increases the rate of alkylation, but still only a low yield of pyrone ester 2.4 (20–30%) and significant amounts of a high running spot, presumed to be alkylation of the pyrone-OH, are obtained (Scheme 6.9).

Scheme 6.9
Low yielding alkylation of pyrone inhibitor 6.16 with NaH/THF

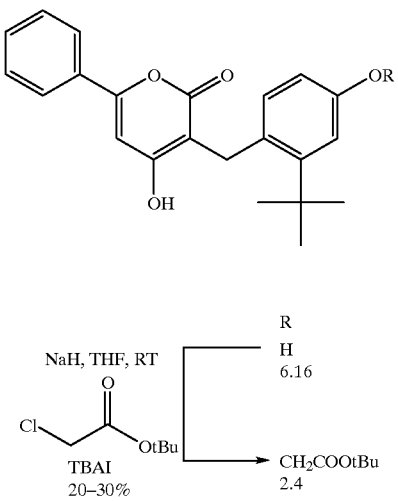

The more robust protecting groups benzyl and allyl were evaluated (Scheme 6.10). The allyl-protected pyrone inhibitor 6.15 is reacted with Cs₂CO₃/BnBr in NMP at 60° C. to give a 65% yield of the benzyl ether 6.17. The allyl ether in 6.17 is cleaved to give the phenol derivative 6.18, which was alkylated with Cs₂CO₃ at 60° C. to yield the benzyl ether pyrone ester 6.19 in 82% yield.

Scheme 6.10
Synthesis of benzyl ether protected tert-butyl acetoxy pyrone 6.19

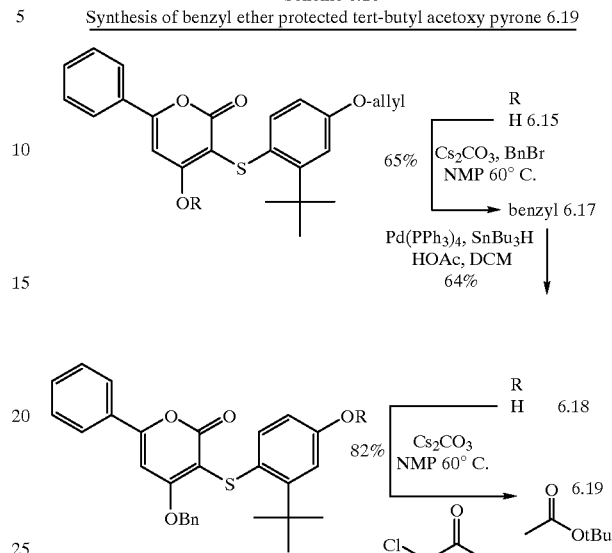

Alternatively, another approach takes advantage of the pyrone-OH acidity (Scheme 6.11). The pyrone hydroxyl proton in 6.16 is selectively deprotonated and alkylated with allyl iodide/DIEA give the mono-protected allyl ether 6.20 in 48% yield. Alkylation of the phenol 6.20 under the conditions previously described produces the ester 6.21 in 82% yield. However, when allyl ether 6.21 is saponified, the product 6.22 contained a methyl ether. This indicates that methoxide adds to the pyrone in 1,4 conjugate fashion, releasing allyl oxide (Scheme 6.12). Because of the extra steps and the poor overall yields, this protecting group "shuffle" is not preferred.

Scheme 6.11
Synthesis of allyl ether protected tert-butyl acetoxy pyrone 6.21

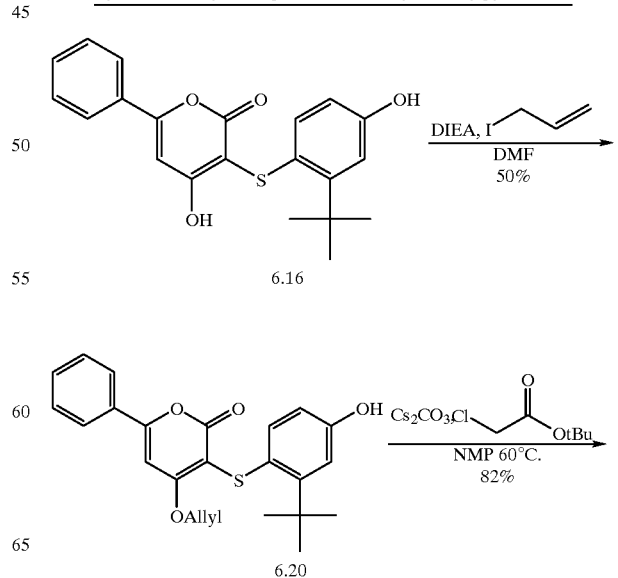

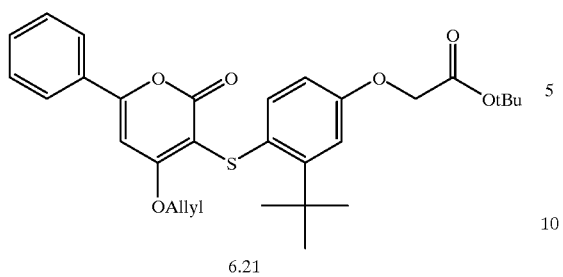

6.21

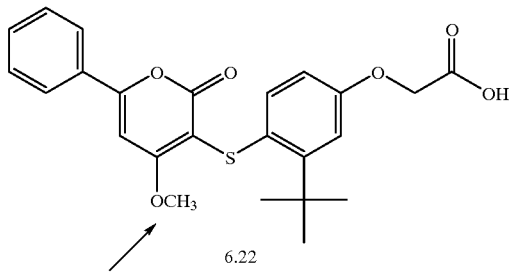

6.22

Since a one-step alkylation is the easiest route to the pyrone ester 2.4, direct alkylation of the unprotected pyrone 6.16 with tbutyl chloroacetate was employed. Reaction of 6.16 with tBuOK/tert-butyl chloroacetate/TBAI at 0° C. warming to room temperature gives 2.4 in 30–70% yield (Scheme 6.13). The potassium phenoxide anion reacts faster with tert-butyl chloroacetate/TBAU than does the sodium phenoxide anion, and also reacts faster than the pyrone anion, allowing better yields of the product 2.4. The best yields are obtained by keeping the reaction temperature at 0° C. and carefully monitoring the reaction products by TLC.

Taking advantage of the ease of the ester hydrolysis, mild LiOH(aq) treatment cleanly produces the acid 6.23 in 78–85% yield. The amide 6.24 was synthesized in 74% yield by reaction of acid 6.23 with mono-Boc protected hexane diamine (Scheme 6.13).

Compound 6.25 can be synthesized using an identical approach. See also Hagen et al. (1997), J. Med. Chem. 40:3707–3711.

Scheme 6.12
Saponification of allyl ether protected tert-butyl acetoxy pyrone 6.21

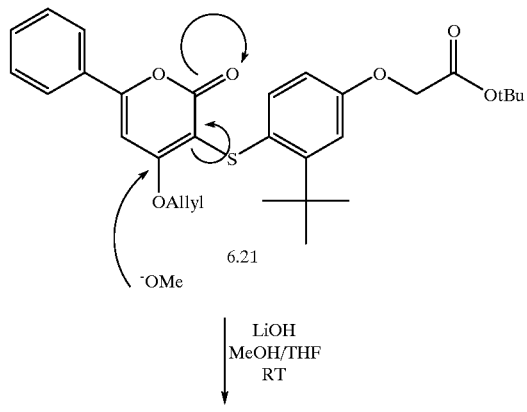

Scheme 6.13
Synthesis of acetoxy acid pyrone inhibitor 6.23 and acetoxy hexane diamine amide pyrone inhibitor 6.24

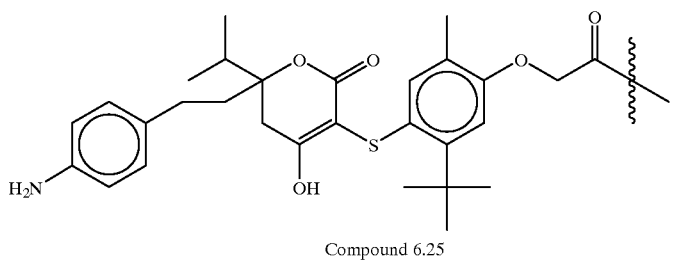

Compound 6.25

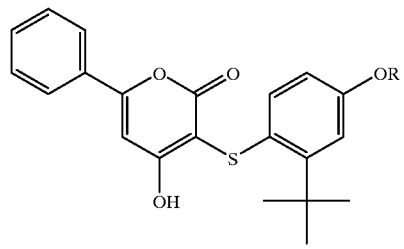

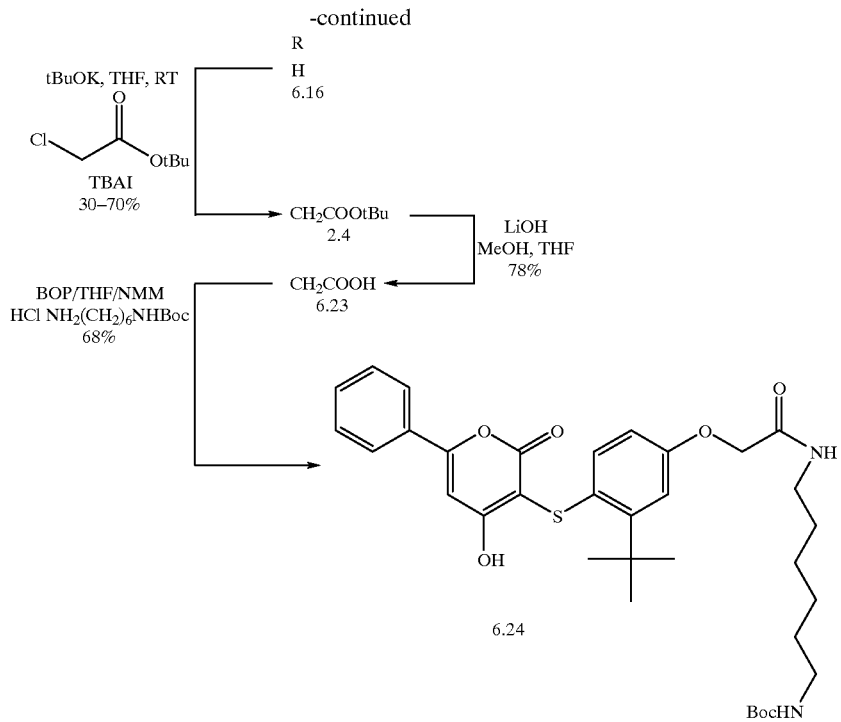

VX-478 Analog Synthesis

Compound 2.6, a VX-478 analog modified to contain Tyr(OCH₂CO₂Et) in the P₁ position instead of a Phe, is synthesized from an appropriate epoxide, isobutylamine, and sulfonyl chloride (Scheme 7.1). In contrast to CS-131 2.2, which is derived from (2R,3S) Boc-Phe-epoxide, MES-14-069 2.6 is derived from the (2S,3S)-Tyr-epoxide and thus requires a different synthesis than used previously for CS-131. An approach based on a procedure reported by Kempf et al. (1995), Synlett 613 is used to synthesize (S,S) Boc-Tyr(OBn)-epoxide, which was successfully transformed into 2.6.

Scheme 7.1.
Synthesis of Bn₂N-Tyr(OBn)-epoxide 7.5.

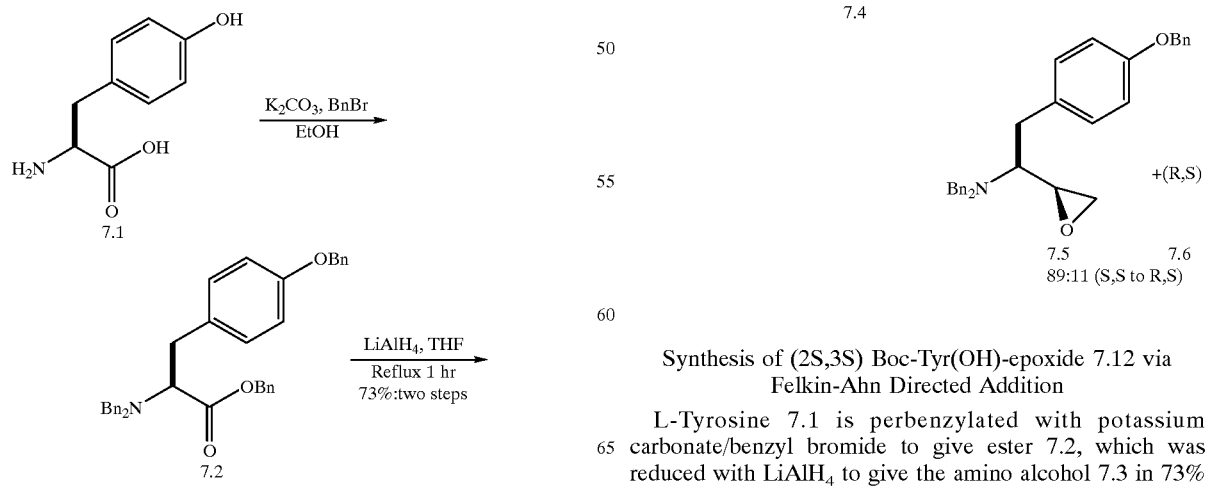

Synthesis of (2S,3S) Boc-Tyr(OH)-epoxide 7.12 via Felkin-Ahn Directed Addition L-Tyrosine 7.1 is perbenzylated with potassium carbonate/benzyl bromide to give ester 7.2, which was reduced with LiAlH₄ to give the amino alcohol 7.3 in 73% yield after recrystallization from ethyl acetate/hexane (Scheme 7. 1). Alcohol 7.3 is oxidized with pyridine-SO₃ to aldehyde 7.4, which is reacted with chloromethyl lithium to give a mixture of 7.5 (2S,3S) and 7.6 (2R,3S) epoxides in 89:11 ratio via Felkin-Ahn directed addition. The chloromethyl lithium reagent used for the aldehyde addition was derived from lithiation of bromochloromethane with lithium metal. Since these epoxides are unstable to silica gel, crystallization of the HCl salts is required for purification. The crude epoxides 7.5 and 7.6 are treated with HCl(aq)/THF to form the chlorohydrin HCl salts 7.7 and 7.8 which can be recrystallized at 5° C. to give a 30% yield of the pure (2S,3S) diastereomer 7.7 (Scheme 7.2).

Scheme 7.2.
Synthesis of 2S,3S HCl H₂N-Tyr-chlorohydrin 7.9.

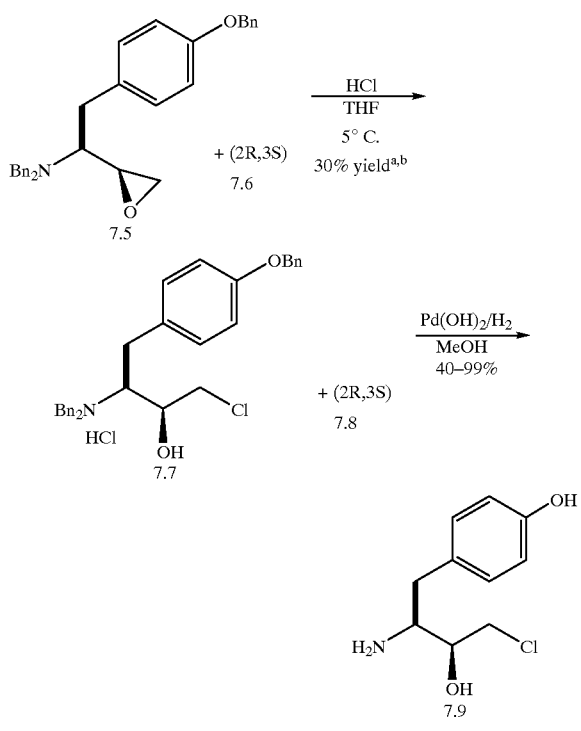

[a] 30% yield of recrystallized 7.7 from amino alcohol 7.3.
[b] ¹HNMR shows one diastereomer.

HCl salt 7.9 is acylated with di-tert-butyl dicarbonate and then epoxidized with KOH/MeOH to give Boc-Tyr(OH)-epoxide 7.12 in 25–50% yield (Scheme 7.4).

Scheme 7.4.
Synthesis of Boc-Tyr(OBn)-epoxide 7.12 from chlorohydrin 7.9.

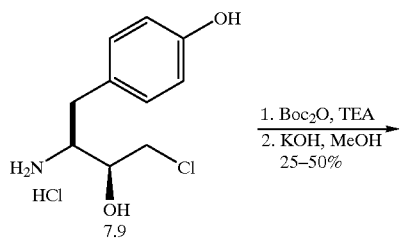

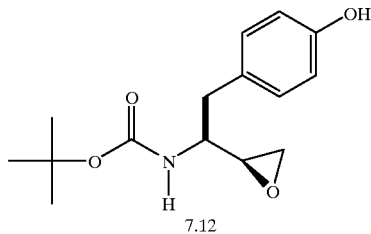

Synthesis of (2S,3S) Boc-Tyr(OBn)-epoxide 7.19
via chelation-controlled addition This synthesis was adapted for the synthesis of Boc-Tyr (OBN)-epoxide (Scheme 7.5). Boc-Tyr(OBn)-OH 7.13 is reacted with Cs₂CO₃MeI to form the methyl ester 7.14. The crude ester 7.14 is reduced to the aldehyde with DIBAL and treated with vinylmagnesium bromide in situ to give ca. 4:1 ration of (3S,4S) to (3R,4S) allylic alcohols 7.15 and 7.16, which are separable by column chromatography. The (3S, 4S) allylic alcohol 7.15 is treated with mesyl chloride to give 7.17 (Scheme 7.6). Crude mesylate 7.17 is ozonolyzed to the adlehyde, which is reduced with NaBH₄ to give alcohol 7.18 in excellent yield. Reaction of 7.18 with NaH in refluxing THF smoothly produces (2S,3S) Boc-Tyr(OBn)-epoxide 7.19 in 86% yield.

FIG. 7.5.
Synthesis of allyl alcohol 7.15.

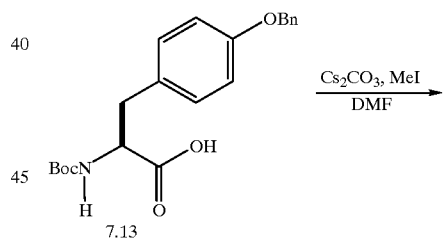

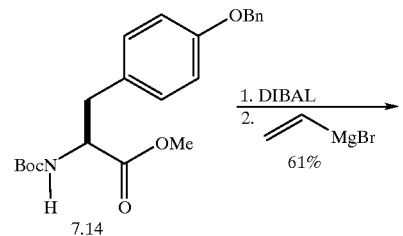

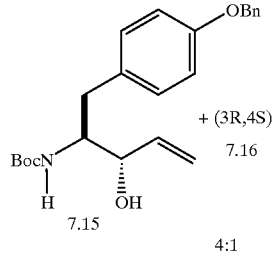

Scheme 7.6.
Synthesis of (2S,3S)-Boc-Tyr(OBn)-Epoxide 7.19.

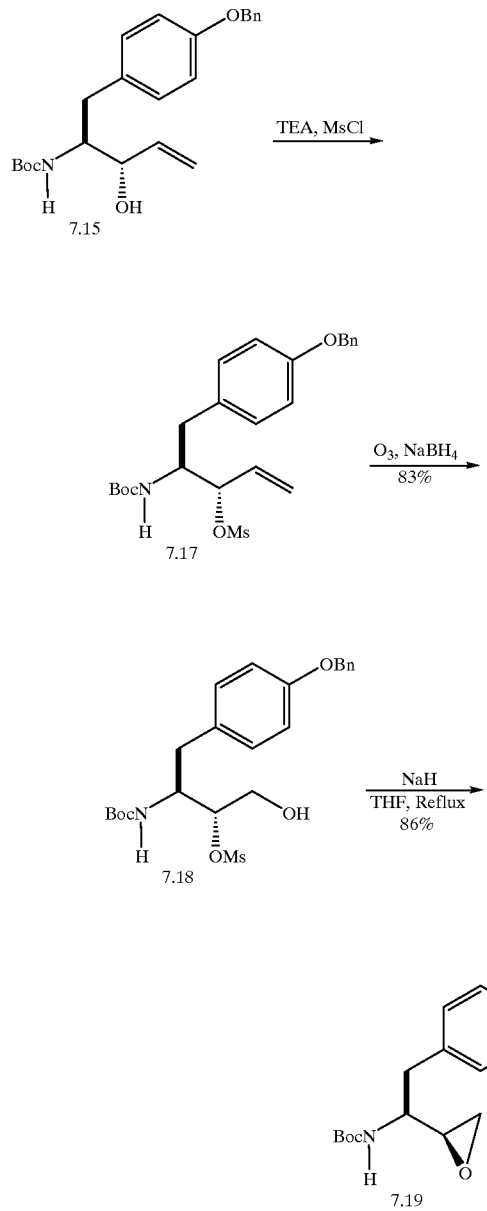

Scheme 7.7.
Reaction of sulfonyl chloride with hydroxyethylamine 7.20 produces sulfonates 7.21 and 7.22.

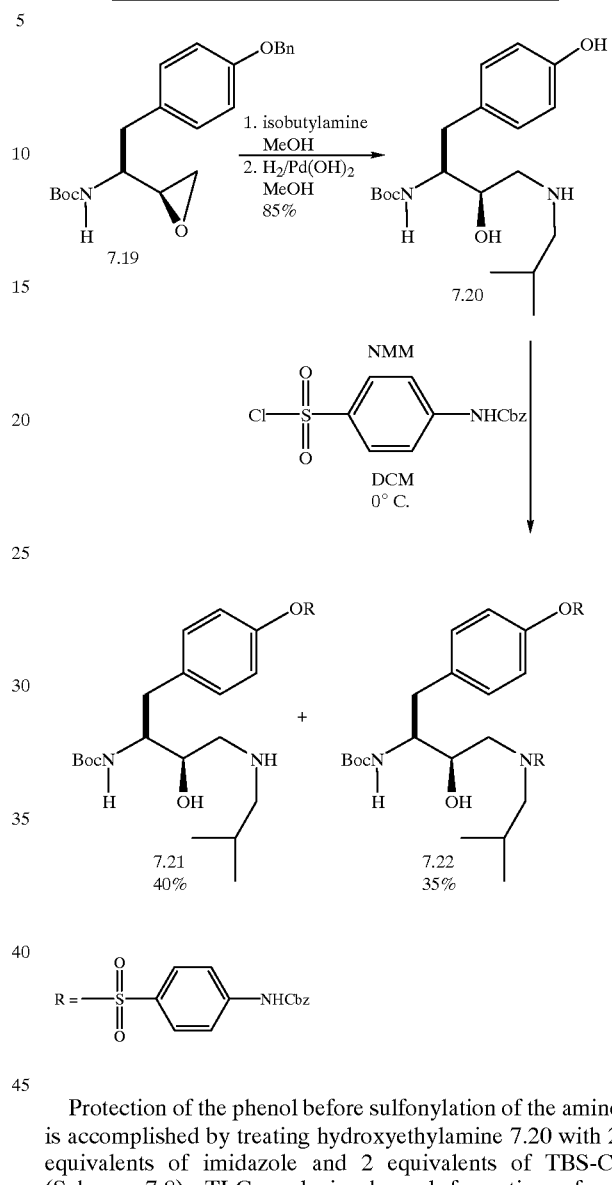

Completion of Compound 2.6

The hydroxyethylamine isostere is constructed by reaction of the epoxide 7.19 with isobutylamine (Scheme 7.7). After stirring overnight in methanol, the reaction mixture is concentrated from ether several times and then hydrogenated over Pd(OH)$_2$/methanol to give the fully deprotected hydroxymethylamine 7.20 in 85% yield. Although 7.20 can be recrystallized from ethyl acetate/hexane, it is generally more convenient to use the crude product directly in the next reaction. To the fully deprotected hydroxyethylamine 7.20 in CH$_2$Cl$_2$ at 0° C., was added 4-carbobenzyloxyaminophenylsulfonyl chloride dropwise. This yields two products; a very polar spot 7.21 in 40% yield, and a high running spot 7.22 in 35% yield. The products correspond to mono-sulfonylation of the phenol 7.21 and di-sulfonylation of the phenol and amine 7.22, indicating that the phenol reacts preferentially over the amine.

Protection of the phenol before sulfonylation of the amine is accomplished by treating hydroxyethylamine 7.20 with 2 equivalents of imidazole and 2 equivalents of TBS-Cl (Scheme 7.8). TLC analysis showed formation of an intermediate, followed by formation of a higher running spot, which suggested that the TBS-Cl was reacting with both the free amine and the phenol. After aqueous workup which presumably cleaves the N-TBS bond, treatment of the crude OTBS-protected intermediate with 4-carbobenzylaminophenylsulfonyl chloride/TEA in THF smoothly produces the desired N-sulfonylated/O-TBS protected product 7.23 in 61% yield (Scheme 7.8). The TBS group is cleaved with HF/pyridine to give the phenol, which is reacted directly with Cs$_2$CO$_3$/ethyl bromoacetate in dioxane at 40–50° C. for 3 hours to form the ester 7.24 in 71% overall yield. The ester 7.24 is reacted with HCl/dioxane to give the HCl salt, which is treated with 3-(S)-hydroxytetrahydrofuran p-nitrophenyl carbonate/TEA to give Cbz-protected analog 7.5 (Scheme 7.9). At this point, the ester can be hydrolyzed to give the free acid 7.26 or it can be hydrogenated with Pd(OH)$_2$ to give 2.6 in quantitative yield.

Scheme 7.8.
Synthesis of Cbz protected MES-14-069 7.24 from hydroxyethylamine 7.20.

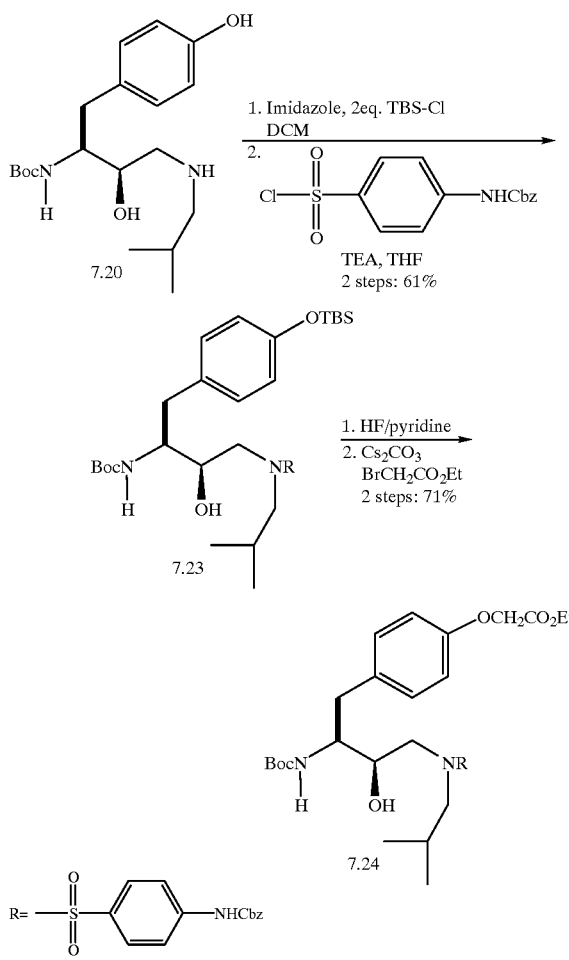

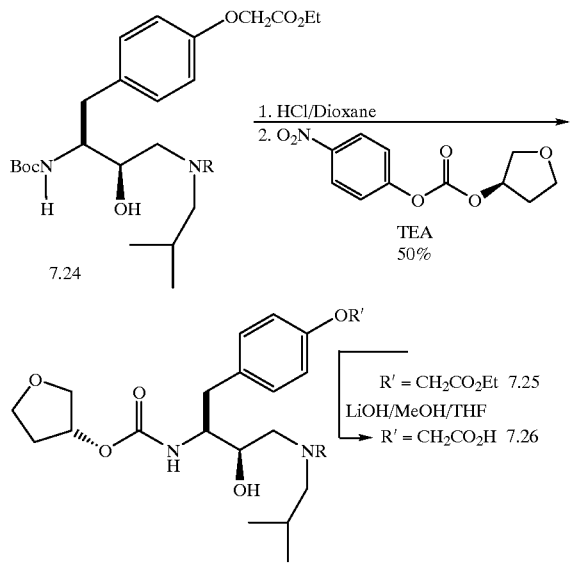

Scheme 7.9.
Synthesis of MES-14-069 2.6.

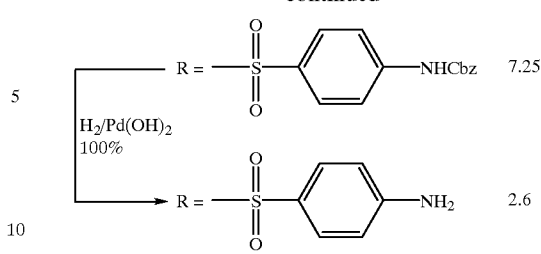

Synthesis of Conjugates 2.8, 2.10, and 2.12

(MeLeu(3-OH)[1], D-MeSer[3], Lys(2CL-Cbz)[7])CsA 4.20 (Scheme 4.9) is hydrogenated using Pd(OH)$_2$/MeOH to give the free amine 4.11, which was used in the next reaction without further purification. The completely deprotected CS-131 acid derivative 5.13 is coupled to the CsA analog free amine 4.11 with PyAOP to give the desired conjugate 2.8 in 50% yield (Scheme 8.2).

Scheme 8.2.
Synthesis of conjugate 2.8.

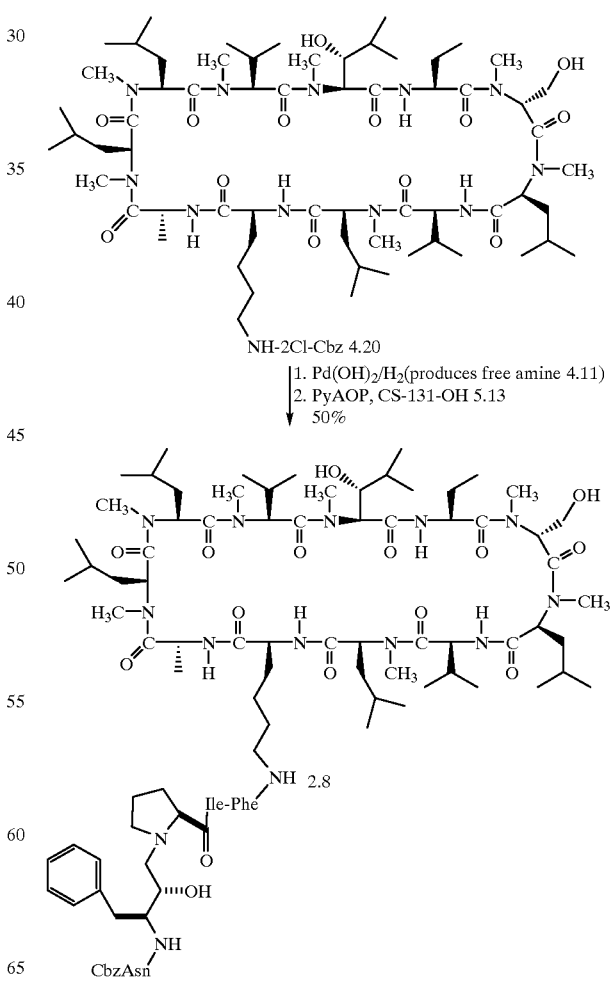

Similarly, the pyrone inhibitor 6.23 is coupled to the CsA analog free amine with PyAOP to give the conjugate 2.9 in 56% yield (Scheme 8,3), and to Cbz protected 7.26 to give the Cbz-protected conjugate 8.2 in 50% yield. Cleavage of the Cbz group from 8.2 produces the fully deprotected conjugate 2.10 (Scheme 8.4).
Scheme 8.3.
Synthesis of conjugate 2.9.
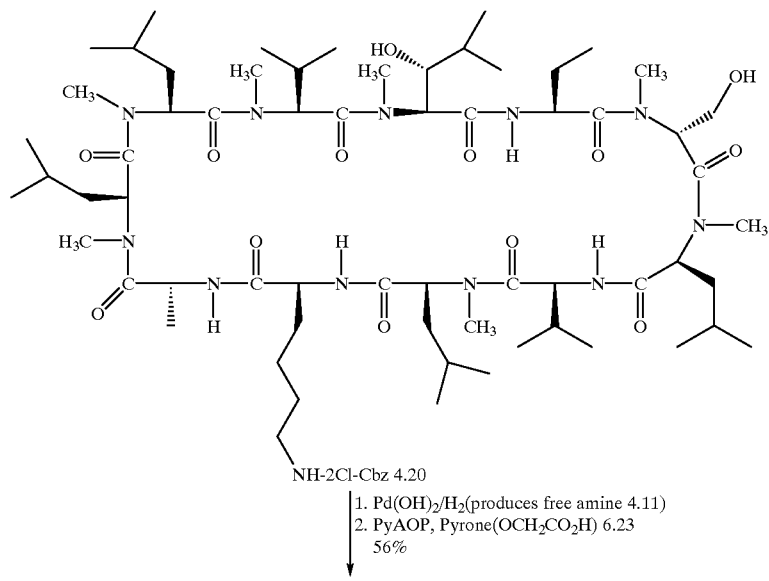
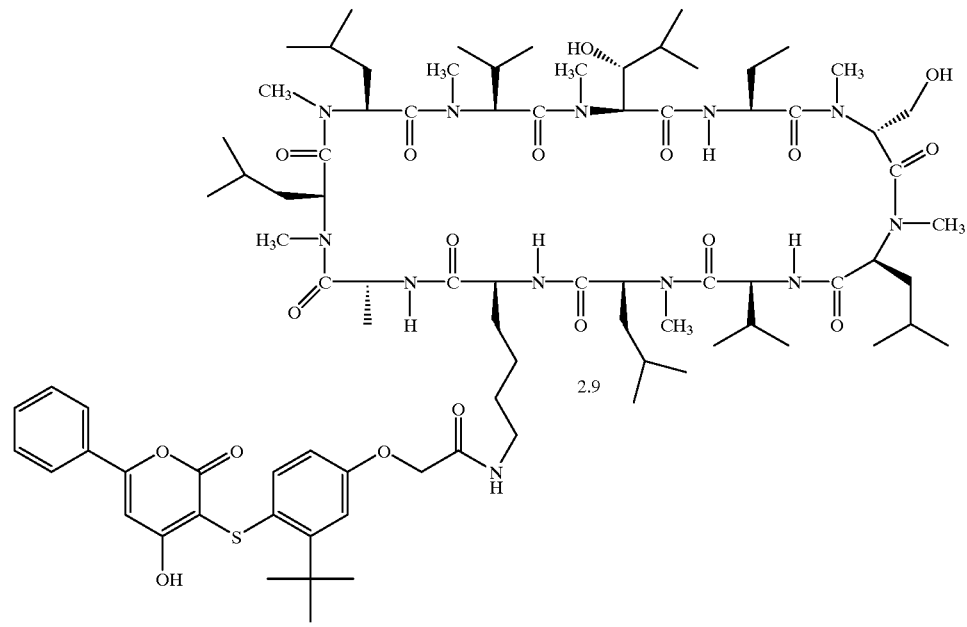

Scheme 8.4.
Synthesis of conjugate 2.10.

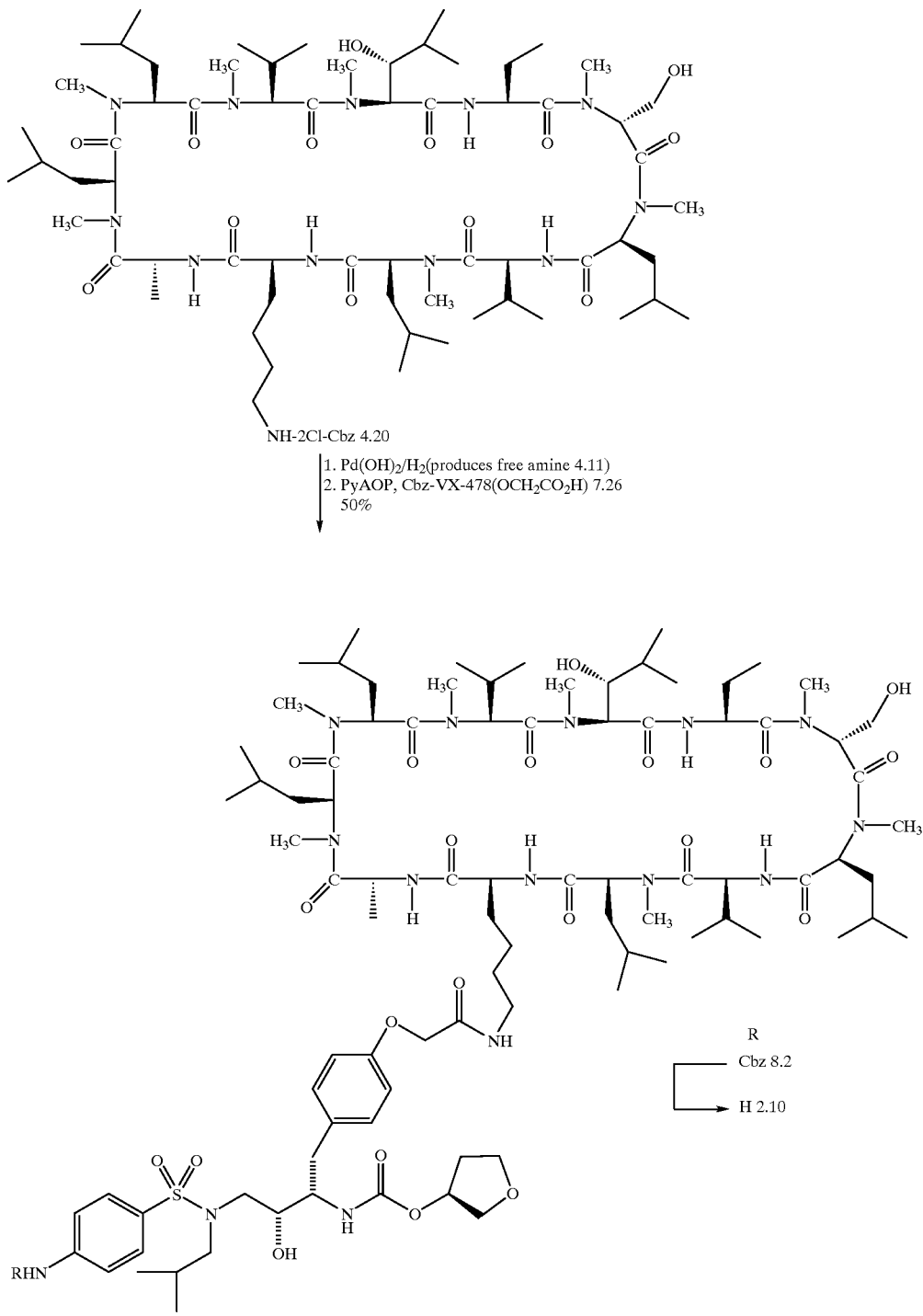

To provide a reactive group for coupling of the HIV protease inhibitors, them semisynthetic derivative OL-17, 2.11 is reacted with p-nitrophenol chloroformate to produce the carbonate 8.3 in 74% yield (Scheme 8.5). After cleavage of the Boc group in pyrone inhibitor 6.24, the resulting HCl salt was reacted with the carbonate 8.3 in THF to give the semisynthetic conjugate 2.12 in 24% yield.

Scheme 8.5.
Synthesis of semisynthetic pyrone conjugate 2.12.

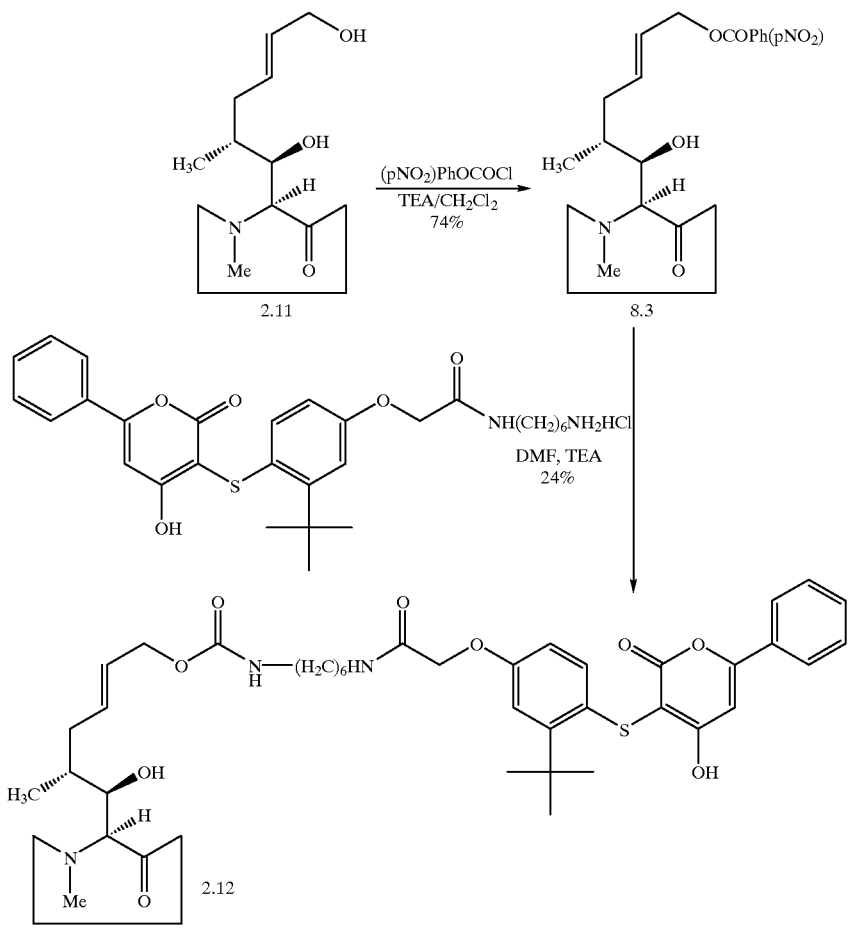

Conjugate 2.8 (Scheme 12.1), which incorporates (MeLeu (3-OH)[1], D-MeSer[3], Lys[7])CsA and the hydroxyethylamine HIV protease inhibitor 5.13, exhibits potent activity against HIV protease ($K_i$=1 nM) and against cyclophilin ($K_i$=20 nM). This result clearly shows that each domain in the conjugate retains the ability to independently inhibit each enzyme. The conjugate also binds to both enzymes simultaneously: preincubating the conjugate with a 1000-fold excess of cyclophilin did not alter the HIV protease inhibitory activity of the conjugate. Additionally, a preliminary ultracentrifugation experiment indicated that a complex (30 KDa) which was larger than either enzyme (18 and 22 KDa) had been formed, which corroborates the initial data that the conjugate binds simultaneously to cyclophilin and HIV protease.

The pyrone conjugate 2.9 (Scheme 12.2) also strongly inhibits both cyclophilin ($K_i$=9.3 nM) and HIV protease ($K_i$=3.4 nM). Since the parent Parke-Davis HIV protease inhibitor has a $K_i$=7.3 nM against HIV protease, the acetoxy group/lysine side-chain has no effect on the conjugate's ability to inhibit HIV protease.

FIG. 12.1. The structures of CS-131 allyl ester analog 5.9 and 2.8.

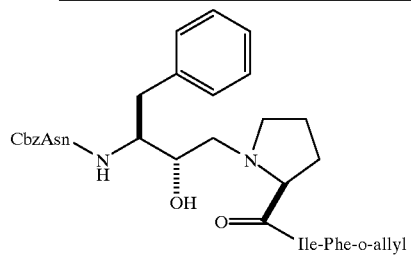

CS-131 allyl ester analog 5.9.

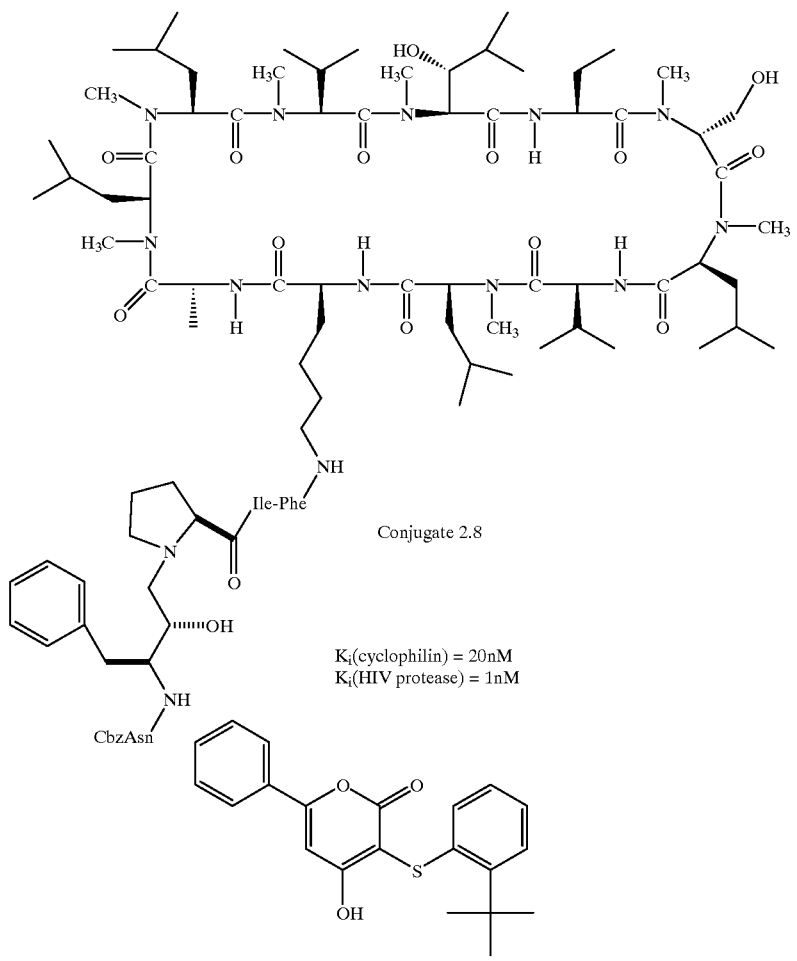
Conjugate 2.8
$K_i$(cyclophilin) = 20nM
$K_i$(HIV protease) = 1nM
Parke Davis pyrone inhibitor 2.3
FIG. 12.2. The structures of pyrone inhibitor 2.3, conjugate 2.9, and designed pyrone inhibitor 6.24.
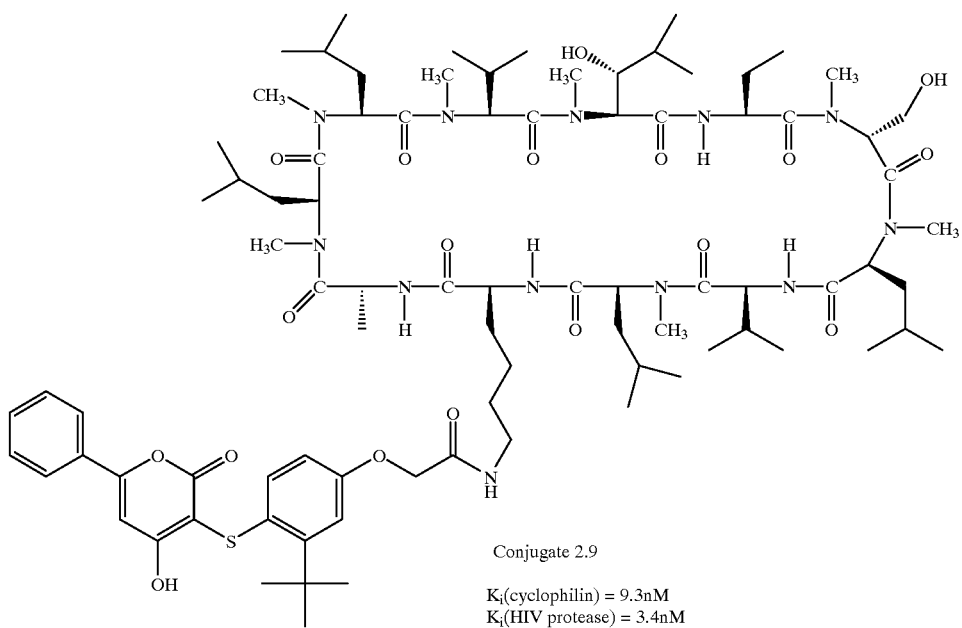
Conjugate 2.9
$K_i$(cyclophilin) = 9.3nM
$K_i$(HIV protease) = 3.4nM -continued

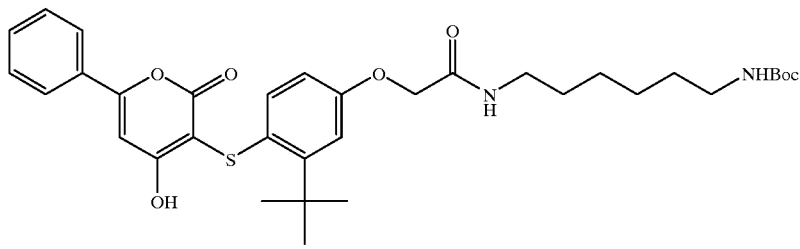

designed pyrone inhibitor 6.24

Design, Synthesis and Biological Activity of the Conjugate Containing the Acetoxy Acid-Modified VX-478 inhibitor 7.26

VS-478 2.5 (Scheme 12.3) has excellent bioavailability and antiviral activity, and thus provided an inhibitor with a different cell penetration profile than those used for conjugates 2.8 and 2.9. In the design and synthesis of conjugates 2.9 and 2.9, the C-terminus of the known inhibitor CS-131 and the corresponding "C-terminus" end of the pyrone inhibitor are available for functionalization. In 2.5, the C-terminal position corresponds to the aniline nitrogen of the sulfonamide group. However, the x-ray structure of VS-478 complexed with HIV protease indicates that this nitrogen is hydrogen bonded to the enzyme and sterically constrained, so much so that derivatization of the aniline nitrogen would lead to unfavorable interactions with the enzyme. In contrast, the para position of the benzyl group in the $P_1$ position is exposed to solvent and therefore used as the functionalization position. An acetoxy group was chosen to provide the linking functionality as in conjugate 2.9. The coupling of the modified VS-478 inhibitor 7.26 to the CsA analog 4.11 proceeds in a straight-forward manner, to give the desired conjugate 2.10 (Scheme 12.3). Notably, inhibitor 7.26 was soluble in DCM which was used as the coupling solvent.

Compound 2.6, which is modified VX-478 inhibitor containing an ethyl acetoxy linking group, shows approximately the same activity against HIV protease ($K_i$=1 nM) as VS-478 2.5 ($K_i$=0.6 nM), thereby establishing that modification of VX-478's $P_1$ substituent has no effect on its inhibition of HIV protease. The conjugate 2.10 (Scheme 12.2) also exhibits potent activity against both cyclophilin ($K_i$=6 nM) and HIV protease ($K_i$=2.3 nM), indicating that the CsA analog has no effect on the inhibition of HIV protease.

Conjugates 2.8, 2.10, and 2.12 have been evaluated for anti-HIV activity in infected cell lines against both susceptible and protease-resistant HIV; see the Examples.

FIG. 12.3. The structures of VX-478 2.5 and conjugate 2.10.

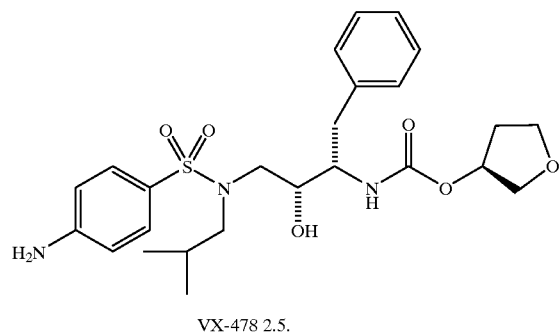

VX-478 2.5.

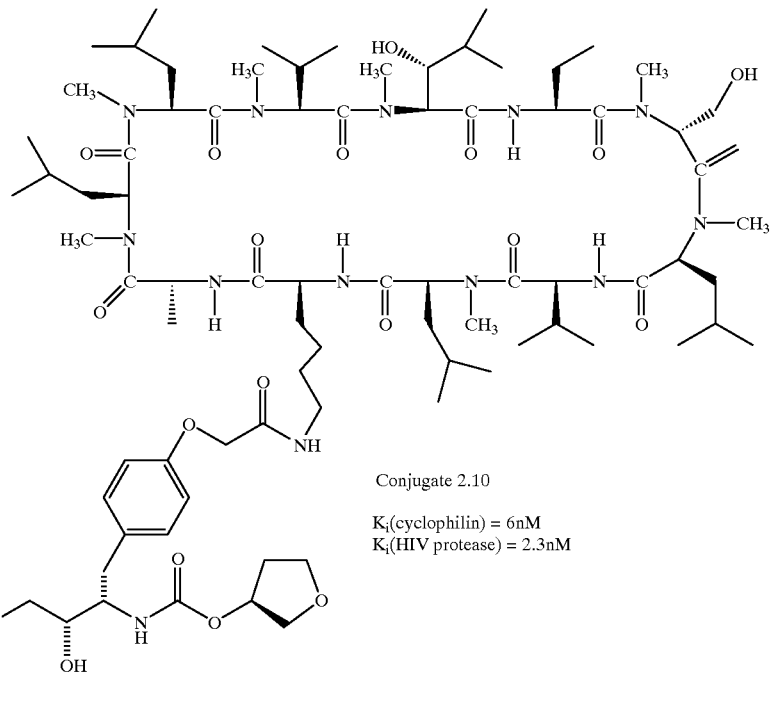

Conjugate 2.10

$K_i$(cyclophilin) = 6nM
$K_i$(HIV protease) = 2.3nM

Treatment of HIV-Mediated Disorders using Pharmaceutical Compositions Containing the Subject Compounds The invention includes a method of inhibiting or treating HIV-mediated disorders in mammals (especially humans). The method includes administering to a subject in need thereof an effective HIV-replication inhibiting amount of one or more of the subject compounds. The compounds may be administered neat or in the form of a pharmaceutical composition comprising one or more active ingredients in combination with a pharmaceutically-acceptable carrier.

In mammalian subjects, the compounds of Formula I can be administered orally, parenterally (including subcutaneous, intradermal, intramuscular and intravenous injection), rectally, and topically (including dermal, buccal, and sublingual administration) in combination with an inert liquid or solid pharmaceutically-acceptable carrier which is suitable for the method of administration chosen. The carrier must be pharmaceutically acceptable in the sense of being compatible with the other ingredients of the formulation and not deleterious to the recipient thereof. Such pharmaceutical carriers are well known in the art. The preferred route of administration is orally.

In in vitro applications, such as in the study of mutant cell types, virus types, or other cellular investigations, the pharmaceutical compositions of the present invention are preferably administered to the cells by adding a predefined amount of a compound of Formula I, diluted in a suitable diluent, to the cell culture medium. As used herein, the terms "administering" or "administration" are synonymous with "treating" or "treatment." In essence, administering to cells in vitro one or more of the compounds of Formula I entails contacting the cells with the compounds or salts of the compounds.

The in vivo dosage in humans and other mammals depends largely upon the affliction being treated, the time since onset of the condition, the progression of the disease, and the age and general health of the patient being treated. Determining the optimum dosage for any given patient is essentially an empirical and ongoing process. Inhibition or prevention of HIV-mediated disorders in infants and children who are diagnosed early in the progression of the condition may optimally require a more (or less) aggressive treatment than in older patients in more terminal stages of AIDS. Of primary importance in optimizing the most effective dosage is that each patient be carefully monitored throughout the course treatment to follow the progression, if any, of the condition.

A suitable effective dose for most conditions ranges from about 1 mg/kg body weight to about 2 g/kg body weight per day, and is preferably in the range of from about 5 to about 500 mg/kg body weight per day (calculated as the non-salt form of the Formula I compound). The total daily dose may be given as a single dose, multiple doses, e.g., two to six times per day, or by intravenous infusion for a selected duration. Dosages above or below the above-cited ranges are within the scope of the invention and such dosages may be administered to individual patients if the circumstances so dictate.

For example, in a 75 kg mammal, a typical daily dosage might fall within the range of from about 75 mg to about 7.5 g per day. If discrete multiple doses are indicated, treatment might typically comprise 4 equal fractional doses given at 8 hour intervals to supply the total daily dosage.

The active ingredients used in the above-described method are analogs and conjugates of CsA and pharmaceutically-acceptable salts thereof. All optical, geometric, and positional isomers of the compounds of Formula I, including racemic mixtures or pure or enriched enantiomeric forms, geometric isomers, and mixtures thereof, are within the scope of this invention.

By the term "pharmaceutically-acceptable salt" is meant any salt conventionally used in the formulation and administration of pharmaceutical preparations. This term encompasses inorganic salts such as nitrates, phosphates, sulfates, and chlorides, as well as mono and di-substituted basic salts of sodium, potassium, calcium, and the like. Organic salts such as malonates, fumarate, succinates, crotonates, and the like are also encompassed by the term "pharmaceutically-acceptable salt." The foregoing list is exemplary, not exclusive. A large number of salts acceptable for pharmaceutical administration are known to those of skill in the art.

The pharmaceutical composition may conveniently be presented in unit dosage form and may be prepared by any of the methods well known in the art of pharmacy. The term "unit dosage" or "unit dose" means a predetermined amount of the active ingredient sufficient to be effective for treating HIV-mediated disorders in man. All methods include the step of bringing the active compound(s) into association with a carrier and one or more optional accessory ingredients. In general, the formulations are prepared by uniformly and intimately bringing the active compound into association with a liquid or solid carrier and then, if necessary, shaping the product into desired unit dosage form.

Formulations of the present invention suitable for oral administration may be presented as discrete units such as capsules, cachets, tablets, boluses or lozenges, each containing a predetermined amount of the active compound; as a powder or granules; or in liquid form, e.g., as an aqueous solution, suspension, syrup, elixir, emulsion, dispersion, or the like.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine a mixture of the powdered active compound with any suitable carrier.

Formulation suitable for parenteral administration conveniently comprise a sterile preparation of the active compound in, for example, water for injection, saline, a polyethylene glycol solution and the like, which is preferably isotonic with the blood of the recipient.

Useful formulations also comprise concentrated solutions or solids containing the compound(s) of Formula I which upon dilution with an appropriate solvent give a solution suitable for parenteral administration.

Preparations for topical or local applications comprise aerosol sprays, lotions, gels, ointments, suppositories etc., and pharmaceutically-acceptable vehicles therefore such as water, saline, lower aliphatic alcohols, polyglycerols such as glycerol, polyethylene glycerol, esters of fatty acids, oils and fats, silicones, and other conventional topical carriers. In topical formulations, the compounds of Formula I are preferable utilized at concentration of from about 0.1% to 5.0% by weight.

Compositions suitable for rectal administration comprise a suppository, preferably bullet-shaped, containing the active ingredient and pharmaceutically acceptable vehicles therefore, such as hard fat, hydrogenated cocoglyceride, polyethylene glycol, and the like. In suppository formulations, the compounds of Formula (1) are preferably utilized at concentrations of from about 0.1% to 10% by weight.

Compositions suitable for rectal administration further comprise a rectal enema unit containing the active ingredient and pharmaceutically acceptable vehicles therefore such as, for example, 50% aqueous ethanol or an aqueous salt solution which is physiologically compatible with the rectum or colon. The rectal enema unit comprises an applicator tip protected by an inert cover, preferably comprised of polyethylene, lubricated with a lubricant such as white petrolatum and preferably protected by a one-way valve to prevent back-flow of the dispensed formula, and of sufficient length, preferably two inches, to be inserted into the colon via the anus. In rectal formulations, the compounds of Formula (1) are preferably utilized at concentrations of from about 5.0% to 10% by weight. Useful formulations also comprise concentrated solutions or solids containing the active ingredient which upon dilution with an appropriate solvent, preferably saline, give a solution suitable for rectal administration. The rectal compositions include aqueous and non-aqueous formulations which may contain conventional adjuvants such as buffers, bacteriostats, sugars, thickening agents and the like. The compositions may be presented in rectal single dose or multi-dose containers.

In pharmaceutical compositions suitable for administration by inhalation, the active ingredient(s) is combined with a carrier comprising a solid in a micronized powder having a particle size in the range of about 5 microns or less to about 500 microns, or a liquid carrier, for rapid inhalation through the oral passage from a conventional metered-dose inhaler or nebulizer. Suitable liquid nasal compositions include conventional nasal sprays, nasal drops and the like, of aqueous solutions of the active ingredient and optional adjuvants.

In addition to the aforementioned ingredients, the pharmaceutical formulations of this invention may further include one or more optional accessory ingredient(s) utilized in the art of pharmaceutical formulations, i.e., diluents, buffers, flavoring agents, colorants, binders, surface active agents, thickeners, lubricants, suspending agents, preservatives (including antioxidants) and the like.

EXAMPLES

The following Examples are included solely to aid in a more complete understanding of the invention disclosed and claimed herein. The Examples do not limit the scope or utility of the invention in any fashion.

General Experimental Procedures

General Procedure A. BOP-Cl Couplings

A solution of the N-protected amino acid (1.1 eq) and amino acid ester or peptide amino acid ester (1.0 eq) was cooled to 0° C. in DCM (0.15 M). To the cooled solution was added TEA (2.1 eq) and then BOP-Cl (1.1 eq) in one portion. (An extra equivalent of TEA was added if the amino acid ester or peptide ester was in the form of an HCl salt). The cloudy solution was stirred overnight, warming to room temperature, at which point the solution became clear. The reaction was poured into ethyl acetate (3×reaction volume) and washed with $KHSO_4$, $H_2O$, $NaHCO_3$ and then brine. After drying over $Na_2SO_4$ and filtering, the filtrate was concentrated in vacuo to an oil and purified by flash chromatography.

General Procedure B. BOP-Cl Couplings via Pre-activation

A solution of the N-protected amino acid (1.1 eq) was cooled to 0° C. in DCM (0.15 M). TEA (1.1 eq) and BOP-Cl (1.1 eq) were added and the reaction was stirred at 0° C. for one hour. A solution of the amino acid ester or peptide ester HCl salt and TEA (1.1 eq) in ca. 1 M DCM was then added to the reaction. After stirring overnight and allowing the reaction to warm to room temperature, the reaction was poured into ethyl acetate (3×reaction volume) and washed with $KHSO_4$, $H_2O$, $NaHCO_3$, and then brine. After drying over $Na_2SO_4$ and filtering, the filtrate was concentrated in vacuo to an oil and purified by flash silica gel chromatography.

General Procedure C. EDCI/HOBt Peptide Coupling

A solution of the N-protected amino acid (1.1 eq) and amino acid ester HCl salt (or peptide amino acid ester HCl salt) (1.0 eq) in DCM or DMF (0.20 M) was cooled to 0° C. and treated with TEA (1.05 eq), HOBt (1.5 eq), and EDCI (1.1 eq) in one portion. The solution was stirred overnight while warming to room temperature, poured into ethyl acetate (3×reaction volume) and washed with $KHSO_4$, $H_2O$, $NaHCO_3$, and then brine. After drying over $Na_2SO_4$ and filtering, the filtrate was concentrated in vacuo to an oil and purified by flash silica gel chromatography.

General Procedure D. Boc Group Cleavage with 4N HCl/Dioxane

The Boc-protected amine was dissolved in 4 N HCl/dioxane (20–100 eq) at room temperature and stirred until TLC showed consumption of starting material (ca. 1 hr). The reaction was concentrated in vacuo and then concentrated from ether (3×) and DCM (3×) to produce a white solid.

General Procedure E. TFA Cleavage of Boc Groups

A solution of the Boc-protected amine in DCM (0.2 M) was cooled to −15° C. in a MeOH/ice bath and treated with TFA, bringing the total concentration of the reaction to 0.1M. The reaction was stirred in the cold, until TLC showed consumption of starting material (ca. 1–2 hr), and then added dropwise into a slurry of $NaHCO_3$ (1.1 g per ml of TFA) in $H_2O$ and DCM. The phases were separated and the aqueous phase was extracted with DCM (3×). The organic layers were combined, dried over $Na_2SO_4$, filtered, and concentrated in vacuo to give the neutral free amine.

General Procedure F. Acetonide Protection of MeLeu(3-OH)

2S,3R MeLeu(3-OH) 3.6 was refluxed overnight in freshly distilled acetone (0.003 M) until an almost clear solution of acetonide-protected MeLeu(3-OH) 4.6 was obtained. After concentrating the reaction volume to 1.5–5.0 ml, the amino acid was added directly to the coupling reaction described in general procedure G.

General Procedure G. Synthesis of CsA Heptapeptide by Acetonide-Protected MeLeu(3-OH)

To solution of the hexapeptide free amine (1.0 eq), N-methylmorpholine (1.1 eq), and HOBt (2.2 eq) in THF (0.05M) was added acetonide-protected MeLeu(3-OH) 4.6 (1.1 eq). The mixture was cooled to 0° C. and DCC (1.1 eq) was added in one portion. After stirring the reaction overnight, the dicyclohexylurea (DCU) that precipitated was removed by filtration through celite and washed with small portions of DCM (3×). The filtrate was concentrated in vacuo and dissolved in ethyl acetate which precipitated additional DCU that was filtered off as before. The filtrate was concentrated in vacua and the residue was purified by flash chromatography using acetone/hexane gradients.

General Procedure H. Cleavage of N,O-Isopropylidene from Acetonide-Protected Heptapeptide To a solution of the N,O-isopropylidene-protected peptide in methanol (0.05 M) was added 1.0 N HCl (aq) (4.0 eq) and the reaction was stirred for 12 hours at room temperature. $NaHCO_3$ (12 eq) was added and the reaction was concentrated in vacuo. The resulting white slurry was taken up in 2–4% MeOH/DCM and purified by flash chromatography with 2–4% MeOH/DCM to yield a white foam.

General Procedure I. CsA Linear Undecapeptide Synthesis via "7+4" Coupling

To a solution of the amine heptapeptide benzyl ester (1.0 eq) and N-protected tetrapeptide acid (1.3 eq) in DCM (0.05 M) was added BOP reagent (1.3 eq) and N-methylmorpholine methylmorpholine (2.0 eq). The reaction was stirred for 3 days at room temperature and then concentrated in vacuo. The residue was dissolved in DCM and washed with $H_2O$, the phases were separated, and the aqueous layer was washed with DCM (2×). The organic layers were combined and dried over $Na_2SO_4$, filtered, concentrated in vacuo, and purified by flash chromatography using MeOH/DCM mixtures as the eluant.

General Procedure J. Cyclization of Undecapeptide to Form Cyclosporin A Analogs

A solution of the undecapeptide in ethanol at 0° C. was treated with 0.2 N NaOH. The reaction was stirred at 0° C. for 1.5 hours, at which point an additional 1.0 eq of 0.2 N NaOH was added and the stirring was continued at 0° C. for 6–10 more hours. After acidification with 0.2 N HCl to pH 6, the solution was diluted with brine and extracted with DCM (4×), the organic layers were combined, dried over $Na_2SO_4$, filtered and concentrated in vacuo. The residue was dissolved in DCM and propylphosphonic anhydride (50% w/v in DCM) and DMAP were added. The mixture was stirred at room temperature for 3 days under argon, concentrated in vacuo, and purified by flash chromatography using acetone/hexanes as the eluant to yield a white foam.

General Procedure K. Cleavage of the Cbz Group from the 7-Position of the CsA Analogs A round bottom flask containing the CsA analog and $Pd(OH)_2$ (10–50% by weight) were thoroughly flushed with argon and dissolved in methanol (1–2 ml). The flask was then evacuated and the vacuum was broken with hydrogen (repeated 3×). After stirring for 1–3 hours under I atm of $H_2$, the mixture was filtered through an acrodisk and the filtrate was concentrated in vacuo to give the free amine CsA analog which was used directly in the next reaction.

Example 1

Synthesis of 2S,3R MeLeu(3-OH)

Route 1

Syn-(4S,2'S,3'R)-3-(4'-methyl-3'-hydroxy-2'-bromo-1'-pen tanoyl)4-benzyl-2-oxazolidinone 3.8

A solution of (4S)-3-bromoacetyl-4-phenyl-2-oxazolidinone 3.7 (1.7 g. 5.7 mmol) in ether (28 ml) was cooled to −78° C., and treated with TEA (1.11 ml, 7.98 mmol), followed by di-n-butylboron triflate (1.73 ml, 6.04 mmol). The cooling bath was removed and the reaction was stirred at room temperature for 1.5 hours. After cooling the reaction back to −78° C. with vigorous stirring, isobutyrlaldehyde (0.545 ml, 5.91 mmol) was added and the resulting reaction mixture was stirred at −78° C. for 0.5 hours and at 0° C. for 2 hours. The reaction was diluted with ether (50 ml), washed with $KHSO_4$ (2X), and concentrated in vacuo. The residue was brought up in 1:1 $MeOH/H_2O$ (20 ml), cooled to 0° C., followed by addition of 30% $H_2O_2$ (7 ml). After stirring the reaction for 1 hour at 0° C., it was concentrated in vacuo to give a residue that was diluted with ether (50 ml) and washed with $H_2O$, 1 N $NaHCO_3$, brine, dried over $Na_2SO_4$, filtered and concentrated in vacuo. The residue was purified by flash chromatography (25–30–35% EthOAc/hexane) to give 919 mgs (44% yield) of the aldol product as a foam. $R_f$=0.32 (30% EthOAc/hexane). $[\alpha]_D^{23}$ −+51.9 (c 0.30, $CDCl_3$), $^1$H NMR (300 MHz, $CDCl_3$) δ7.42–7.18 (m, 5H), 5.91 (d, 1H, J=2.3 Hz), 4.8–4.65 (m, 1H), 4.31–4.19 (m, 2H), 3.51 (dd, 1H, J=3, 7.6 Hz), 3.32 (dd, 1H, J=13.5, 3.3 Hz), 2.81 (dd, 1H, J=9.5, 13.5 Hz), 1.96–1.83 (m, 1H), 1.07 (d, 3H, J=6.7 Hz), 0.97 (d, 1H, J=6.7 Hz). $^{13}$C NMR (75.5 MHz, $CDCl_3$) δ169.55, 152.37, 134.61, 129.47, 129.08, 127.56, 75.59, 66.35, 55.24, 48.93, 36.99, 31.96, 18.78, 18.23. HR-EI: calculated for $C_{16}H_{20}NO_4Br$ 369.0576, found 369.0585.

Syn-(4S,2'S,3'R)-3-(4'-methyl-3'-O-N-methylcarbamoyl-2'-bromo-1'-pentanoyl)-4-benzyl-2-oxazolidinone 3.9

A solution of the aldol product 3.8 (694 mg, 1.87 mmol) in toluene (6.5 ml) at room temperature was treated with N-methylisocyanate (0.551 ml, 9.35 mmol) and $BF_3$-$OEt_2$ (0.276 ml, 2.24 mmol). The reaction was stirred for 1 hour, quenched with 5% $NaHCO_3$ (6 ml) and stirred for an additional 30 minutes. After diluting with $H_2O$ (25 ml) and extracting with DCM (3×25 ml), the organic phases were combined, dried over $Na_2SO_4$, filtered, and concentrated in vacuo. The residue was purified by flash chromatography (25–30–35% EthOAc/hexane) to give 583 mgs (73% yield) of the carbamate as a white foam. $R_f$=0.20 (30% EthOAc/hexane). $[\alpha]_D^{23}$=+55.6 (c 0.67, $CDCl_3$), $^1$H NMR (300 MHz, $CDCl_3$) δ7.34–7.19 (m, 5H), 6.05 (d, 1H, J=3.1 Hz), 4.91–4.78 (m, 1H), 4.64–4.54 (m, 1H), 4.35 (m, 1H), 4.20 (dd, 1H, J=8.9, 2.5 Hz), 3.31 (dd, 1H, J=13.4, 3.3 Hz), 2.90–2.73 (m, 4H), 2.15–2.04 (m, 1H), 1.02 (d, 3H, J=6.8 Hz), 0.95 (d, 3H, J=6.6 Hz). $^{13}$C NMR (75.5 MHz, $CDCl_3$) δ166.69, 156.66, 153.49, 135.10, 129.47, 128.10, 127.39, 76.62, 66.81, 56.35, 50.7, 37.56, 31.41, 27.67, 18.29, 18.22. HR-EI: calculated for $C_{18}H_{23}N_2O_5Br$ 428.0771, found 428.0777.

(4R,5R)-3-N-Methyl-4-methylester-5-isopropyl-2-oxazolidinone 3.11

A solution of oxazolidinone carbamate 3.9 (481 mg, 1.12 mmol) in 3:1 THF:$H_2O$ (12 ml) was cooled to 0° C. and treated with LiOH (2.24 ml, 1 N LiOH). The reaction was stirred for 30 minutes and concentrated in vacuo to give a residue that was dissolved in $H_2O$ and wathed with EthOAc (3×50 ml), acidified to pH 2 with 2 N HCl, and extracted with DCM (3×75 ml). The organic layers were combined, dried over $Na_2SO_4$, filtered, and concentrated in vacuo to give 288 mgs (82% yield) of the acid 3.10, which was used crude in the next reaction.

A solution of 3.10 (236 mg, 0.88 mmol) in DMF (6 ml) at room temperature was treated with tert-butoxide (494 mg, 4.4 mmol) After stirring the reaction for 30 minutes, toluene was added, and the reaction was concentrated in vacuo to give a residue that was dissolved in $H_2O$ (50 ml), washed with EthOAc, acidified to pH 2 with 2 N HCl, and extracted with EthOAc (6×50 ml). The organic layers were combined, dried over $Na_2SO_4$, filtered, and concentrated in vacuo. The residue was dissolved in 3:1 THF/MeOH (8.8 ml) and treated with TMS-diazomethane (0.88 ml, 2 M in hexane). The reaction was stirred for 1 hour and concentrated in vacuo to a residue which was purified by flash chromatography (30–40% EthOAc/hexane) to give 128 mgs (72% over two steps) of 3.11 as a clear, fluid-like oil. $R_f$=0.25 (40% EthOAc/hexane). $[\alpha]_D^{23}$=-2.7 (c 0.38, $CDCl_3$), $^1$H NMR (300 MHz, $CDCl_3$) δ4.26 (d, 1H, J=7.6 Hz), 4.19 (dd, 1H, J=9.1, 7.6 Hz), 3.82 (s, 3H), 2.85 (s, 3H), 1.86–1.71 (m, 1H), 1.07 (d, 3H, J=6.5 Hz), 0.98 (d, 3H, J=6.6 Hz). $^{13}$C NMR (75.5 MHz, $CDCl_3$) δ168.89, 81.04, 63.81, 52.49, 42.08, 30.25, 29.3, 18.99, 18.44. HR-EI: calculated for $C_9H_{15}NO_4$ 201.1001, found 201.0992.

(2S,3R)-MeLeu(3-OH) 3.6

The oxazolidinone methyl ester 3.11 (400 mg, 2.0 mmol) was dissolved in ethanol (2.27 ml) and treated with KOH (2.27 ml, 1.03 N KOH). The reaction was refluxed for 1 hour, cooled to room temperature, and concentrated in vacuo to give trade 3.12. The resulting white slurry was directly treated with KOH (aq) (4.4 ml, 1.59 M), stirred at 80° C. overnight, and concentrated in vacuo. After acidifying the mixture to pH 6 with 1 N HCl, it was purified by ion-exchange chromatography ("DOWEX" 50×, 4% $NH_4OH$) to give 242 mgs (75% yield) of 3.6 as a white solid. $^1$H NMR (300 MHz, $D_2O$) δ4.8 (s, 3H), 3.69 (dd, 1H, J=7.15, 5.0 Hz), 3.56 (d, 1H, J=7.15 Hz), 2.73 (s, 3H), 1.82 (m, 1H), 0.97 (d, 3H, J=3.8 Hz), 0.95 (d, 1H, J=3.66 Hz). $^{13}$C NMR (75.5 MHz, $CDCl_3$) δ167.98, 80.28, 63.02, 51.72, 29.47, 28.52, 18.21, 17.63.

(2S,3R) MeLeu(3-OH) Synthesis Route 2

(2E)-4-Methyl-2-penten-1-ol 3.14

A solution of 3.13 (13 g, 112.5 mmol) in THF (300 ml) at −78° C. was treated dropwise with DIBAL (248 ml of a 1 M solution in THF). The reaction was stirred for 2 hours at −78° C., quenched carefully with MeOH, and diluted with ether (200 ml). The mixture was washed with 3 N HCl, phases were separated, and the aqueous phase was extracted with ether (3×100 ml). The combined organic layers were washed with brine, dried over $Na_2SO_4$, filtered, and concentrated in vacuo. The residue was distilled under reduced pressure to give 9.6 g (85% yield) of the alcohol 3.14. $R_f$=0.55 (30% EthOAc/hexanes). $^1$H NMR (300 MHz, $CDCl_3$) δ5.73–5.5 (m, 1H), 4.12–4.03 (m, 1H), 2.39–2.2 (m, 1H), 1.55 (bs, 1H), 1.0 (d, 6H, J=6.6 Hz).

(2S,3R)-4-Methyl-2,3-epoxy-1-ol 3.15

A flame-dried flask was charged with 4-angstrom powdered molecular sieves (2.34 g) and DCM (275 ml) and then cooled to −20° C. in MeOH/ice bath. D-(−)-diethyl tartarate (0.99 ml, 4.7 mmol) and Ti(Oi—Pr)$_4$ (1.16 ml, 3.9 mmol) were added sequentially, followed by cumene hydroperoxide (80% solution, stored over 4-angstrom molecular sieves, 28.9 ml, 156 mmol) at a moderate rate. The resulting reaction mixture was transferred to the refrigeration apparatus set at −20° C., stirred for 30 minutes, and then treated with allylic alcohol 3.14 (7.8 g, 78 mmol) dropwise over 10 minutes, and the resulting mixture was stirred overnight at −20° C.

A freshly prepared solution of ferrous sulfate heptahydrate (25.8 g) and tartaric acid (7.8 g) in deionized $H_2O$ (78 ml) was cooled to 0° C. The epoxidation reaction was allowed to warm to 0° C. and was then poured into a beaker containing the precooled ferrous sulfate solution. The two-phase mixture was stirred for 5–10 minutes and then transferred to a separatory funnel. After the phases were separated, the aqueous phase was extracted with ether (2×100 ml) and the combined organic layers were treated with a precooled solution of 30% NaOH (w/v) (7.8 ml) in saturated brine and stirred vigorously for 1 hour at 0° C. The reaction mixture was diluted with $H_2O$, the phases were sepated, and the aqueous layer was extracted with ether (3×100 ml). The combined organic phases were dried over $Na_2SO_4$, filtered, and concentrated in vacuo to give a residue which was purified by flash chromatography (2:1 hexane/EthOAc) to give 6.5 g (72% yield) of the epoxide 3.15 as a colorless oil. $R_f$=0.35 (33% EthOAc/hexanes). $^1$H NMR (300 MHz, $CDCl_3$) δ3.92 (d, 1H, J=11.7 Hz), 3.72–3.53 (m, 1H), 3.02–2.95 (m, 1H), 2.76 (dd, 1H, J=6.8, 2.4 Hz), 2.30 (m, 1H), 1.66–1.50 (m, 1H), 1.03 (d, 3H, J=6.7 Hz), 0.97 (d, 3H, J=6.9 Hz). $^{13}$C NMR (75.5 MHz, $CDCl_3$) δ61.94, 61.22, 57.59, 30.03, 18.96, 18.31.

(2S,3R)-4-Methyl-2,3-epoxy-1-O-methylcarbamate 3.17

A solution of the epoxy alcohol 3.15 (1.014 g, 8.75 mmol) in DCM (130 ml) was treated sequentially with TEA (3.05 ml, 21.88 mmol) and methylisocyanate (1.032 ml, 17.5 mmol). The mixture was stirred under argon for 20 hours, quenched with satd. NH$_4$Cl, and transferred to a separatory funnel. The phases were separated and the aqueous phase was extracted with DCM (3×100 ml). The combined organic phases were dried over Na$_2$SO$_4$, filtered, and concentrated in vacuo to give a residue which was purified by flash chromatography (30% EthOAc/hexane) to give 1.32 g (87% yield) of the carbamate 3.17 as a colorless oil. R$_f$=0.55 (30% EthOAc/hexanes). $^1$H NMR (300 MHz, CDCl$_3$) δ4.75 (bs, 1H), 4.40 (dd, 1H, J=12.21, 2.85 Hz), 3.89 (dd, 1H, J=12.13, 6.4 Hz), 3.01 (m, 1H), 2.81 (d, 3H, J=4.94 Hz), 2.65 (dd, 1H, J=6.72, 2.67 Hz), 1.65–1.50 (m, 1H), 1.01 (d, 3H, J=6.72 Hz), 0.96 (d, 3H, J=6.87 Hz). $^{13}$C NMR (75.5 MHz, CDCl$_3$) δ65.63, 61.92, 54.79, 30.07, 27.50, 18.87, 18.25. FABMS: found 174.1 [M+H$^+$].

(4R,5R)-3-N-Methyl-4-hydroxymethyl-5-isopropyl-2-oxazolidinone 3.16

A solution of KH (224 mg, 5.6 mmol) in THF (50 ml) at 0° C. was treated dropwise with a solution of the carbamate 3.17 (647 mg, 3.74 mmol) in THF (5 ml). The reaction was stirred at 0° C. for 2 hours and then at room temperature for 1 hour. After quenching the reaction at 0° C. with 1 N KHSO$_4$ to pH 5, it was extracted with CHCl$_3$ (9×50 ml) and the combined organic layers were dried over Na$_2$SO$_4$, filtered, and concentrated in vacuo. The residue was purified by flash chromatography (30–40% acetone/hexane) to give 415 mgs (65% yield) of the desired oxazolidinone 3.16 as a white solid, and 104 mgs (16% yield) of the other isomer 3.18. Data for 3.16; R$_f$=0.38 (50% acetone/hexanes). $^1$H NMR (300 MHz, CDCl$_3$) δ4.05 (dd, 1H, J=10.38, 7.04 Hz), 3.86 (m, 1H), 3.61 (m, 1H), 2.94 (s, 3H), 2.86 (m, 1H), 2.15 (m, 1H), 1.09 (d, 3H, J=6.45 Hz), 0.956 (d, 3H, J=6.6 Hz). $^{13}$C NMR (75.5 MHz, CDCl$_3$) δ159.38, 82.66, 61.08, 52.28, 29.80, 27.49, 19.68, 18.94. HR-EI: calculated for C$_8$H$_{15}$NO$_3$ 173.1052, found 173.1057. Data for 3.18; R$_f$=0.45 (50% acetone/hexanes). $^1$H NMR (300 MHz, CDCl$_3$) δ4.32 (dd, 1H, J=8.5, 6.9 Hz), 4.18 (dd, 1H, J=8.5, 8.5 Hz), 3.75 (m, 1H), 3.47 (d, 1H, J=8.17 Hz), 3.01 (d, 1H, J=3.8 Hz), 2.78 (s, 3H), 1.55 (m, 1H), 0.98 (d, 3H, J=6.61 Hz), 0.83 (d, 3H, J=6.79 Hz). $^{13}$C NMR (75.5 MHz, CDCl$_3$) δ159.38, 72.33, 61.92, 59.85, 30.47, 29.08, 19.40, 18.95. FABMS found 174.1 [M+H$^+$].

(4R,5R)-3-N-Methyl-4-methylester-5-isopropyl-2-oxazolidinone 3.11

A solution of the oxazolidinone alcohol 3.16 (600 mg, 3.47 mmol) in acetone (16 ml) at 0° C. was treated with Jones reagent (1.55 ml, prepared by adding 5.34 g of CrO$_3$ dropwise to 4.6 ml conc. H$_2$SO$_4$ and diluting with water to 20 ml) and stirred for 1 hour at room temperature. An additional 0.400 ml of Jones reagent was added and the reaction was stirred for another hour. After decomposing the remaining Jones reagent with isopropanol, the reaction mixture was decanted into another flask and the remaining solids were dissolved in satd. NaCl and extracted with CHCl$_3$ (3×50 ml). The organic layers were combined, dried over Na$_2$SO$_4$, filtered and concentrated in vacuo to give 3.10 which was used directly in the next reaction.

Acid 3.10 was dissolved in 3:1 benzene/MeOH (36 ml) and treated with TMS-diazomethane (3.47 ml, 2 M in hexanes). The reaction mixture was stirred for 1 hour at room temperature and concentrated in vacuo. The residue was purified by flash chromatography (40% EthOAc/hexane) to give 490 mgs (70% over two steps) of the methyl ester 3.11 as a colorless oil. R$_f$=0.25 (40% EthOAc/hexane). [α]$_D^{23}$=−2.7 (c 0.38, CDCl$_3$), $^1$H NMR (300 MHz, CDCl3$_3$) δ4.26 (d, 1H, J=7.6 Hz), 4.19 (dd, 1H, J=9.1, 7.6 Hz), 3.82 (s, 3H), 2.85 (s, 3H), 1.86–1.71 (m, 1H), 1.07 (d, 3H, J=6.5 Hz), 0.98 (d, 3H, J=6.6 Hz). $^{13}$C NMR (75.5 MHz, CDCl$_3$) δ168.89, 81.04, 63.81, 52.49, 42.08, 30.25, 29.3, 18.99, 18.44. HR-EI: calculated for C$_9$H$_{15}$NO$_4$ 201.1001, found 201.0992.

Example 2

Synthesis of CsA Analogs

Boc-MeLeu-Lys(2Cl-Cbz)-OBn 4.1

Following general procedure A, the title compound was synthesized in 80% yield by coupling of the HCl salt of H-Lys(2Cl-Cbz)-OBn (8.56 g, 19.4 mmol) to Boc-MeLeu-OH (5.24 g, 21.3 mmol) in DCM (130 ml) with BOP-Cl (5.43 g, 21.3 mmol) and DIEA (10.5 ml, 60.1 mmol) to give 9.78 g of the dipeptide. R$_f$=0.29 (30% EthOAc/hexane), [α]$_D^{23}$=−53.01 (c 0.415, CHCl$_3$), FABMS (C$_{33}$H$_{46}$N$_3$O$_7$Cl) found 632.1.

Boc-Val-Melxu-Lys(2Cl-Cbz)-OBn 4.2

Following general procedure D, the Boc group in Boc-MeLeu-Lys(2Cl-Cbz)-OBn 4.1 (9.78 g, 15.5 mmol) was cleaved to form the HCl salt of MeLeu-Lys(2Cl-Cbz)-OBn, which was coupled to Boc-Val-OH (3.7 g, 17.0 mmol) in DCM (105 ml) with BOP-Cl (4.33 g, 17.0 mmol) and DIEA (8.35 ml, 48.0 mmol) via general procedure B to give 6.68 g (59% yield) of the title compound. R$_f$=0.30 (40% EthOAc/hexane), [α]$_D^{23}$=−59.30 (c 0.860, CHCl$_3$), FABMS (C$_{38}$H$_{55}$N$_4$O$_8$Cl) found 731.2.

Boc-MeLeu-Val-MeLcu-Lys(2Cl-Cbz)-OBn (SEQ. ID. NO: 2) 4.3

Following general procedure D, the Boc group in Boc-Val-MeLeu-Lys(2Cl-Cbz)-OBn 4.2 (6.68 g, 9.13 mmol) was cleaved to form the HCl salt of Val-MLeu-Lys(2Cl-Cbz)-OBn, which was coupled to Boc-MeLeu-OH (2.463 g, 10.04 mmol) in DCM (60 ml) with BOP-Cl (2.553 g, 10.04 mmol) and DIEA (4.93 ml, 28.3 mmol) via general procedure A to give 5.367 g (69% yield) of the title compound. R$_f$=0.37 (50% EthOAc/hexane), [α]$_D^{23}$=−94.33 (c 0.670, CHCl$_3$), FABMS (C$_{45}$H$_{68}$N$_5$O$_9$Cl) found 858.3.

Boc-(D)MeSer(OBn)-MeLeu-Val-MeLeu-Lys(2 Cl-Cbz)-OBn (SEQ. ID. NO: 3) 4.4

Following general procedure E, the Boc group in Boc-MeLeu-Val-MeLeu-Lys(2Cl-Cbz)-OBn 4.3 (773 mg, 0.886 mmol) was cleaved to form H-Meleu-Val-MeLeu-Lys(2Cl-Cbz)-OBn, which was coupled to Boc-(D)MeSer(OBn)-OH-DCHA salt (464 mg, 0.946 mmol) in DCM (6 ml) with BOP-Cl (241 mg, 0.946 mmol) and DIEA (0.165 ml, 0.946 mmol) via general procedure A to give 638 mg (71% yield) of the title compound. R$_f$=0.33 (50% EthOAc/hexane), [α]$_D^{23}$=−48.09 (c 0.47, CHCl$_3$), FABMS (C$_{56}$H$_{81}$,N$_6$O$_{11}$, Cl) found 1049.3.

Boc-Abu-(D)MeSer(OBn)-MeLeu-Val-MeLeu-Lys (2Cl-Cbz)-OBn (SEQ. ID. NO: 4) 4.5

Following general procedure E, the Boc group in Boc-(D)MeSer(OBn)-MeLeu-Val-MeLeu-Lys(2Cl-Cbz)-OBn 4.4 (618 mg, 0.589 mmol) was cleaved to form H-(D)MeSer(OBn)-Val-MeLeu-Lys(2Cl-Cbz)-OBn, which was coupled to Boc-Abu-OH (247 mg, 1.22 mmol) in DCM (5 ml) with BOP-Cl (311 mg, 1.82 mmol) and DIEA (0.313 ml, 1.82 mmol) via general procedure B to give 450 mg (68% yield) of the title compound. $R_f$=0.33 (50% EthOAc/hexane), $[\alpha]_D^{23}$=−66.10 (c 0.295, $CHCl_3$), FABMS ($C_{60}H_{88}N_7O_{12}Cl$) found 1134.4.

Acetonide-MeLeu(3-OH)-Abu-(D)MeSer(OBu)-MeLeu-Val-MeLeu-Lys(2Cl-Cbz)-OBn (SEQ. ID. NO: 5) 4.7

Following general procedure F, MeLeu(3-OH) 3.6 (50 mg, 0.31 mmol) in refluxing acetone (100 ml) was protected as the N,O-acetonide 4.6 and used in the coupling reaction below.

Following general procedure E, the Boc group in Boc-Abu-(D)MeSer(OBn)-MeLeu-Val-MeLeu-Lys(2Cl-Cbz)-OBn 4.5 (330 mg, 0.29 mmol) was cleaved to form H-Abu-(D)MeSer(OBn)-MeLeu-Val-MeLeu-Lys(2Cl-Cbz)-OBn, which was coupled to the protected MeLeu(3-OH) in THF (4.5 ml) with DCC (64 mg, 0.31 mmol), HOBt (84 mg, 0.62 mmol) and NMM (0.034 ml, 0.31 mmol) via general procedure G to give 245 mg (70% yield) of the title compound. The compound was purified by flash chromatography with a 10–20–30% acetone/hexane gradient. $R_f$=0.38 (40% acetone/hexane), $[\alpha]_D^{23}$=−40.0 (c 0.295, $CHCl_3$), FABMS ($C_{65}H_{97}N_8O_{122}Cl$) found 1217.5.

H-MeLeu(3-OH)-Abu-(D)MeSer(OBn)-MeLeu-Val-MeLeu-Lys(2Cl-Cbz)-OBn(SEQ. ID. NO: 6) 4.8

Following general procedure H, the acetonide was cleaved from the protected heptapeptide 4.7 (235 mg, 0.193 mmol) with 1 N HCl (aq) (0.772 ml) in MeOH (3.92 ml) to give 173 mgs (76% yield) of the title compound. $R_f$=0.11 (5% MeOH/DCM), $[\alpha]_D^{23}$=−88.6 (c 0.175, $CHCl_3$), FABMS ($C_{62}H_{93}N_8O_{12}Cl$) found 1177.5.

Fmoc-(D)Ala-MeLeu-Meleu-MeVal-Meleu(3OH)-Abu-(D)MeSer(OBn)-MeLeu-Val-MeLeu-Lys(2Cl-Cbz)-OBn (SEQ ID. NO: 7) 4.9

Following general procedure I, H-MeLeu-Abu-(D)MeSer(OBn)-MeLeu-Val-MeLeu-Lys(2Cl-Cbz)OBn 4.8 (170 mg, 0.144 mmol) was coupled to Fmoc-(D)Ala-MeLeu-MeLeu-MeVal-OH (SEQ. ID. NO: 8) (147 mg, 0.216 mmol) in DCM (3 ml) with BOP (96 mg, 0.216 mmol) and NMM (0.040 ml, 0.36 mmol) to give 139 mg (53% yield) of the title compound. The compound was purified by flash chromatography with a 10–20–30–40% acetone/hexane gradient. $R_f$=0.55 (50% acetone/hexane), $[\alpha]_D^{23}$=−95.5 (c 0.20, $CHCl_3$), FABMS ($C_{100}H_{145}N_{12}O_{18}Cl$) found 1837.9.

(MeLeu(3-OH)$^1$, (D)MeSer(OBn)$^3$, Lys(2Cl-Cbz)$^7$)-CsA (SEQ. ID. NO: 9) 4.10

Following general procedure J, Fmoc-(D)Ala-MeLeu-MeLeu-MeVal-MeLeu(3-OH)-Abu(D)MeSer(OBn)-MeLeu-Val-MeLeu-Lys(2Cl-Cbz)-OBn 4.9 (133 mg, 0.0724 mmol) was treated with 0.2 N NaOH (0.8 ml) in ethanol (3.5 ml) to give the deprotected undecapeptide, which was cyclized by using propylphosponic anhydride (0.054 ml, 50% (v/v) in DCM) and DMAP (49 mg, 0.398 mmol) in DCM (345 ml). The compound was purified by flash chromatography (10–20–30% acetone/hexane) to give 72 mg (66% yield) of the CsA analog 4.10. $R_f$=0.46 (50% acetone/hexane), FABMS ($C_{78}H_{127}N_{12}O_{15}Cl$) found 1507.7.

Boc-(D)MeSer(OTBS)-OH 4.13

A solution of Boc-(D)MeSer-OH 4.12 (3.641 g, 16.47 mmol) in DMF (80 ml) was treated with TBS-Cl (12.413 g, 82.35 mmol) and imidazole (11.213 g, 164.7 mmol). The reaction was stirred overnight at room temperature, and then concentrated from toluene in vacuo on the high-vacuum. The residue was suspended in $H_2O$, acidified to pH 4 with 10% citric acid, and extracted with ether (3×). The combined organic layers were dried over $Na_2SO_4$, filtered, and concentrated in vacuo. The residue was purified by flash chromatography (100% DCM, then 7–10% MeOH/DCM) to give 3.404 g (62% yield) of the title compound. $R_f$=0.68 (95:4:1 DCM/MeOH/HOAc), $[\alpha]_D^{23}$=+4.4 (c 0.635, $CHCl_3$), $^1H$ NMR (30 Q MHz, $CDCl_3$) (mixture of cis-trans isomers) δ4.68–4.28 (m, 1H), 4.06–3.85 (m, 2H), 2.95–2.81 (m, 3H), 1.46–1.36 (m, 9H), 0.90–0.78 (m, 9H), 0.10-(−) 0.03 (m, 6H).

Boc-(D)MeSer(OTBS)-MeLeu-Val-MeLeu-Lys(2Cl-Cbz)-OBn (SEQ. ID. NO: 10) 4.15

Following general procedure E, the Boc group in Boc-MeLeu-Val-MeLeu-Lys(2Cl-Cbz)-OBn 4.3 (7.966 g, 9.279 mmol) was cleaved to form H-MeLeu-Val-MeLeu-Lys(2Cl-Cbz)-OBn, which was coupled to Boc-(D)MeSer(OTBS)-OH 4.13 (3.405 g, 10.21 mmol) in DCM (62 ml) with BOP-Cl (2.596 g, 10.21 mmol) and DIEA (3.395 ml, 19.49 mmol) via general procedure A to give 5.38 g (58% yield) of the title compound. $R_f$=0.60 (60% EthOAc/hexane), $[\alpha]_D^{23}$=−48.24 (c 0.425, $CHCl_3$), FABMS ($C_{55}H_{88}N_6O_{11}ClSi$) found 1073.6.

Boc-(D)MeSer-MeLeu-Val-MeLeu-Lys(2Cl-Cbz)-OBn (SEQ. ID. NO: 11) 4.14

A solution of Boc-(D)MeSer(OTBS)-MeLeu-Lys(2Cl-Cbz)-OBn 4.15 (5.23 g, 4.87 mmol) in THF (88 ml) was treated with HF/pyridine stock solution (74 ml of a stock solution prepared from 18.75 g HF/pyridine, 18.8 ml pyridine, and 75 ml THF) and the reaction was stirred at room temperature for 5 hours. The reaction mixture was combined with 75 ml of 1 N $NaHCO_3$, and extracted with DCM (3×250 ml). The organic layers were combined, dried over $Na_2SO_4$, filtered, and concentrated in vacuo. The residue was purified by flash chromatography (60% EthOAc/hexane) to give 4.15 g (89% yield) of the title compound. $R_f$=0.10 (60% EthOAc/hexane), $[\alpha]_D^{23}$=−45.0 (c 0.5, $CHCl_3$), FABMS ($C_{49}H_{75}N_6O_{11}Cl$) found 959.5.

Boc-Abu-(D)MeSer-MeLeu-Val-MeLeu-Lys(2Cl-Cbz)-OBn (SEQ. ID. NO: 12) 4.16

Following general procedure E, the Boc group in Boc-(D)MeSer-MeLeu-Val-MeLeu-Lys(2Cl-Cbz)-OBn 4.14 (934 mg, 0.975 mmol) was cleaved to form H-(D)MeSer-Val-MeLeu-Lys(2Cl-Cbz)-OBn, which was coupled to Boc-Abu-OH (217 mg, 1.07 mmol) in DCM (6.5 ml) with BOP-Ci (272 mg, 1.07 mmol) and DIEA (0.357 ml, 2.05 mmol) via general procedure B to give 693 mg (68% yield) of the title compound. $R_f$=0.36 (80% EthOAc/hexane), $[\alpha]_D^{23}$=−48.4 (c 0.57 $CHCl_3$), FABMS ($C_{53}H_{82}N_7O_{12}Cl$) m/z 1044.5.

Acetonide-MeLeu(3-OH)-Abu-(D)MeSer-MeLeu-Val-MeLeu-Lys(2Cl-Cbz)-OBn (SEQ. ID. NO; 13) 4.17

Following general procedure F, MeLeu(3-OH) 3.16 (509 mg, 3.16 mmol) in refluxing acetone (1400 ml) was protected as the N,O-acetonide 4.6 and used in the coupling reaction below.

Following general procedure E, the Boc group in Boc-Abu-(D)MeSer-MeLeu-Val-MeLeu-Lys(2Cl-Cbz)-OBn 4.16 (3 g, 2.87 mmol) was cleaved to form H-Abu-(D)MeSer(OBn)-MeLeu-Val-MeLeu-Lys(2Cl-Cbz)-OBn, which was coupled to the protected MeLeu(3-OH) 4.6 in THF (49 ml) with DCC (652 mg, 3.16 mmol), HOBt (852 mg, 3.16 mmol) and NMM (0.347 ml, 3.16 mmol) via general procedure G to give 2.58 mg (80% yield) of the title compound. The compound was purified by flash chromatography with a 20–30–40–50% acetone/hexane gradient. $R_f$=0.6 (50% acetone/hexane), $[\alpha]_D^{23}$=−44.1 (c 0.365, CHCl$_3$), FABMS ($C_{58}H_{91}N_8O_{12}Cl$) found 1127.5.

H-MeLeu(3-OH)-Abu-(D)MeSer-MeLeu-Val-MeLeu-Lys(2Cl-Cbz)-OBn (SEQ. ID. NO: 14) 4.18

Following general procedure H, the acetonide was cleaved from the protected heptapeptide 4.17 (2.55 g, 2.26 mmol) with 1 N HCl (aq) (9.04 ml) in MeOH (45 ml) to give 1.65 g (67% yield) of the title compound. $R_f$=0.25 (10% MeOH/DCM), $[\alpha]_D^{23}$=−41.5 (c 0.585, CHCl$_3$), FABMS ($C_{55}H_{87}N_8O_{12}Cl$) m/z 1087.5.

Fmoc-(D)Ala-MeLeu-MeLeu-MeVal-MeLeu(3-OH)-Abu-(D)MeSer-MeLeu-Val-MeLeu-Lys(2Cl-Cbz)-OBn (SEQ. ID. NO: 15) 4.19

Following general procedure I, H-MeLeu-Abu-(D)MeSer(OBn)-MeLeu-Val-MeLeu-Lys(2Cl-Cbz)-OBn 4M (1.63 g, 1.48 mmol) was coupled to Fmoc-(D)Ala-MeLeu-MeLeu-MeVal-OH (1.13 g, 1.92 mmol) in DCM (30 ml) with BOP (851 mg, 2.22 mmol) and NMM (0.325 ml, 2.96 mmol) to give 1.3 g (50% yield) of the title compound. The compound was purified by flash chromatography with a 20–30–40% acetone/hexane gradient. $R_f$=0.46 (50% acetone/hexane), $[\alpha]_D^{23}$=−107.8 (c 0.45, CHCl$_3$), FABMS ($C_{93}H_{139}N_{12}O_{18}Cl$) found 1749.0.

(MeLeu(3-OH)$^1$, (D)MeSer(OBn)$^3$, Lys(2Cl-Cbz)$^7$)-CsA (SEQ. ID. NO: 16) 4.20

Following general procedure I, Fmoc-(D)Ala-MeLeu-MeLeu-MeVal-MeLeu(3-OH)-Abu-(D)MeSer-MeLeu-Val-MeLeu-Lys(2Cl-Cbz)-OBn (1.25 g, 0.715 mmol) 4.19 was treated with 0.2 N NaOH (7.85 ml+3.9 ml) in ethanol (36 ml) to give the deprotected undecapeptide, which was cyclized by using propylphosponic anhydride (0.526 ml, 50% (v/v) in DCM) and DMAP (480 mg, 3.93 mmol) in DCM (345 ml). The compound was purified with flash chromatography (10–20–30% acetone/hexane) to give 531 mg (53% yield) of the title compound. $R_f$=0.42 (50% acetone/hexane), FABMS ($C_{71}H_{121}N_{12}O_{15}Cl$) found 1417.8.

Boc-MeAla-Lys(2Cl-Cbz)-OBn 11.1

Following general procedure A, the title compound was synthesized in 80% yield by coupling of the HCl salt of H-Lys(2Cl-Cbz)-OBn (8.81 g, 20.8 mmol) to Boc-MeAla-OH (4.65 g, 22.9 mmol) in DCM (140 ml) with BOP-Cl (5.83 g, 21.3 mmol) and DIEA (11.24 ml, 65.5 mmol) to give 9.82 g of the dipeptide. $R_f$=0.50 (50% EthOAc/hexane), $[\alpha]_D^{23}$=−38.6 (c 0.515, CHCl$_3$), FABMS ($C_{30}H_{40}N_3O_7Cl$) found 590.3.

Boc-Val-MeAla-Lys(2Cl-Cbz)-OBn 11.2

Following general procedure D, the Boc group in Boc-MeLeu-Lys(2Cl-Cbz)-OBn 11.1 (9.753 g, 16.5 mmol) was cleaved to form the HCl salt of MeLeu-Lys(2Cl-Cbz)-OBn, which was coupled to Boc-Val-OH (3.957 g, 18.2 mmol) in DCM (110 ml) with BOP-Cl (4.63 g, 18.2 mmol) and DIEA (8.935 ml, 51.3 mmol) via general procedure B to give 7.23 g (63% yield) of the title compound. $R_f$=0.30 (60% EthOAc/hexane), $[\alpha]_D^{23}$=−92.6 (c 0.685, CHCl$_3$), FABMS ($C_{35}H_{49}N_4O_8Cl$) found 689.4.

Boc-MeAla-Val-MeAla-Lys(2Cl-Cbz)-OBn (SEQ. ID. NO: 8) 11.3

Following general procedure D, the Boc group in Boc-Val-MeAla-Lys(2Cl-Cbz-OBn 11.2 (7.27 g, 10.5 mmol) was cleaved to form the HCl salt of Val-MeLeu-Lys(2Cl-Cbz)-OBn, which was coupled to Boc-MeAla-OH (2.35 g, 11.6 mmol) in DCM (70 ml) with BOP-Cl (2.94 g, 11.6 mmol) and DIEA (5.7 ml, 32.6 mmol) via general procedure A to give 3.50 g (43% yield) of the title compound. $R_f$=0.30 (80% EthOAc/hexane), $[\alpha]_D^{23}$=−90.6 (c 0.545, CHCl$_3$), FABMS ($C_{39}H_{56}N_5O_9Cl$) found 774.4.

Boc-Abu-Sar-MeAla-Val-MeAla-Lys(2Cl-Cbz)-OBn (SEQ. ID. NO: 17) 11.4

Following general procedure E, the Boc group in Boc-MeAla-Val-MeAla-Lys(2Cl-Cbz)-OBn 11.3 (665 mg, 0.86 mmol) was cleaved to form H-MeAla-Val-MeAla-Lys(2Cl-Cbz)-OBn, which was coupled to Boc-Abu-Sar-OH (260 mg, 0.946 mmol) in DCM (9 ml) with BOP-Cl (240 mg, 0.946 mmol) and DIEA (0.314 ml, 1.81 mmol) via general procedure A to give 576 mg (72% yield) of the title compound. The compound was purified by flash chromatography (50% acetone/hexane). $R_f$=0.20 (50% acetone/hexane), $[\alpha]_D^{23}$=−92.7 (c 0.655, CHCl$_3$), FABMS ($C_{46}H_{68}N_7O_{11}Cl$) found 952.5 (M+Na$^+$).

Acetonide-MeLeu(3-OH)-Abu-Sar-MeAla-Val-MeAla-Lys(2Cl-Cbz)-OBn (SEQ. ID NO: 18) 11.5

Following general procedure F, MeLeu(3-OH) 3.6 (240 mg, 1.49 mmol) in refluxing acetone (240 ml) was protected as the N,O-acetonide 4.8 and used in the coupling reaction below.

Following general procedure E, the Boc group in Boc-Abu-Sar-MeAla-Val-MeAla-Lys(2Cl-Cbz)-OBn 11.4 (1.26 g, 1.36 mmol) was cleaved to form H-Abu-Sar-MeAla-Val-MeAla-Lys(2Cl-Cbz)-oBn, which was coupled to the protected MeLeu(3-OH) in THF (20.5 ml) with DCC (308 mg, 1.49 mmol), HOBt (403 mg, 2.98 mmol) and NMM (0.164 ml, 1.49 mmol) via general procedure G to give 920 mg (67% yield) of the title compound. The compound was purified by flash chromatography with a 30–40–50% acetone/hexane gradient. $R_f$=0.26 (50% acetone/hexane), $[\alpha]_D^{23}$=−94.8 (c 0.81, CHCl$_3$), FABMS ($C_{51}H_{77}N_8O_{11}Cl$) m/z 1013.7.

H-MeLeu(3-OH)-Abu-Sar-MeAla-Val-MeAla-Lys(2Cl-Cbz)-OBn (SEQ. ID. NO: 19) 11.6

Following general procedure H, the acetonide was cleaved from the protected heptapeptide 11.5 (862 mg, 0.85 mmol) with 1 N HCl (aq) (3.4 ml) in MeOH (17 ml) to give 700 mgs (84% yield) of the title compound. The compound was purified by flash chromatography with a 4–5% MeOH/DCM gradient. $R_f$=0.33 (10% MeOH/DCM), $[\alpha]_D^{23}$=−95.6 (c 0.455, CHCl$_3$), FABMS ($C_{48}H_{73}N_8O_{11}Cl$) found 973.5.

Fmoc-(D)Ala-MeLeu-MeLeu-MeVal-MeLeu(3-OH)-Abu-(D)MeSer(OBn)-MeLeu-Val-MeLeu-Lys(2Cl-Cbz)-OBn (SEQ. ID. NO: 20) 11.7

Following general procedure I, the H-MeLeu-Abu-Sar-MeAla-Val-MeAla-Lys(2Cl-Cbz)-OBn 11.6 (670 mg, 0.69 mmol) was coupled to Fmoc-(D)Ala-MeLeu-MeLeu-MeVal-OH (640 mg, 0.943 mmol) in DCM (14 ml) with BOP (457 mg, 1.03 mmol) and NMM (0.189 ml, 1.72 mmol) to give 658 mg (59% yield) of the title compound. The compound was purified by flash chromatography with a 20–30–40–50% acetone/hexane gradient. $R_f$=0.39 (50% acetone/hexane), $[\alpha]_D^{23}$=−133.0 (c 0.43, CHCl$_3$), FABMS ($C_{86}H_{125}N_{12}O_{17}Cl$) found 1634.4.

(MeLeu(3-OH))$^1$, MeAla$^{4,6}$, Lys(2Cl-Cbz)$^7$)-CsA (SEQ. ID. NO: 21) 11.8

Following general procedure I, Fmoc-(D)Ala-MeLeu-MeLeu-MeVal-MeLeu(3-OH)-Abu-Sar-MeAla-Val-MeAla-Lys(2Cl-Cbz)-OBn 11.7 (640 mg, 0.391 mmol) was treated with 0.2 N NaOH (4.3 ml+2.1 ml) in ethanol (20 ml) to give the deprotected undecapeptide, which was cyclized by using propylphosponic anhydride (0.288 ml, 50% (v/v) in DCM) and DMAP (263 mg, 2.15 mmol) in DCM (1.86 L). The compound was purified with flash chromatography (10–20–30–40–50% acetone/hexane) to give 380 mg (75% yield) of the title compound. $R_f$=0.32 (50% acetone/hexane), FABMS ($C_{64}H_{106}N_{12}O_{14}Cl$) found 1303.8.

Acetylcyclosporin A 4.21

A solution of CsA (200 mg, 0.168 mmol) in acetic anhydride (3.5 ml) was treated with DMAP (41 mg, 0.337 mmol) and the reaction was stirred for 48 hours at room temperature. The reaction was poured into H$_2$O (25 ml) and ether (25 280 ml), phases were separated, and the aqueous phase was extracted with ether (2×25 ml). The organic phases were combined, dried over Na$_2$SO$_4$, filtered, and concentrated in vacuo. The residue was purified by flash chromatography (20–30–40% acetone/hexane) to give 136 mgs of the title compound (65% yield). FABMS calculated for $C_{64}H_{113}N_{11}O_{13}$ 1244.6, found 1244.8.

η-Acetoxyacetylcyclosporin A 4.23

A solution of acetylcyclosporin A in CCl$_4$ was treated with azobisisobutyronitrile (AIBN) and N-bromosuccinimide (NBS). The reaction was refluxed for 2.5 hours and then concentrated in vacuo. The residue was brought up in ether and filtered through celite. The filtrate was washed with H$_2$O, dried over Na$_2$SO$_4$, filtered, and concentrated in vacuo to give crude 4.22. The residue was dissolved in methyl ethyl ketone, and tetraethylammonium acetate hydrate and NaI (cat.) were added to the solution. The reaction was stirred at 60–80° C. for 3 hours and then room temperature for 2 days, diluted with methyl tert-butyl ether and washed with H$_2$O, and brine. The organic layer was dried over Na$_2$SO$_4$, filtered, and concentrated in vacuo. The residue was purified by flash chromatography (20–30–40–50% acetone/hexane) to give 42 mgs (47% yield) of the title compound. FABMS calculated for $C_{66}H_{115}N_{11}O_{15}$ 1301.9, found 1302.

η-Hydroxycyclosporin A (OL-17) 2.11

A solution of the diacetate 4.23 in MeOH was treated with NaOMe (4 eq.) and the reaction was stirred for 2.5 hours at room temperature. The mixture was concentrated in vacuo, the residue was dissolved in methyl tert-butyl ether, washed with H$_2$O, brine, and 1 N NaHCO$_3$, dried over Na$_2$SO$_4$ filtered, and concentrated in vacuo. The residue was purified by flash chromatography (40% acetone/hexane) to give 32 mgs (50% yield) of the title compound. FABMS calculated for $C_{62}N_{111}N_{11}O_{13}$1217.9, found 1218.9.

OL17 p-Nitrophenol carbonate

A solution of η-hydroxycyclosporin A (28 mg, 0.0227 mmol) and p-nitrophenol chloroformate (0.025 mmol) in DCM (0.5 ml) was treated with DIEA (0.004 ml, 0.025 mmol) and the reaction was stirred overnight at room temperature. The reaction was concentrated in vacuo and the residue was purified by flash chromatography (2–3% MeOH/DCM) to give 23 mgs (74% yield) of the carbonate. FABMS found 1383.7.

Example 3

Synthesis of CS-131 Analog and CS-131 Conjugate

Boc-Ile-Phe-Oallyl

According to general procedure C, Boc-Ile-OH (3.07 g, 13.3 mmol) was coupled to the HCl salt of Phe-Oallyl (14.6 mmol) in CH$_2$Cl$_2$ (60 ml) and DMF (6 ml) by using TEA (1.94 ml, 13.9 mmol), HOBt (3.047 g, 19.9 mmol), and EDCI (2.79 g. 14.6 mmol). The product was purified by flash chromatography using 30% EthOAc/Hexane as the eluant to give 78% yield the title compounds an oil. $R_f$=0.38 (40% EthOAc/hexane). $[\alpha]_D^{23}$=+15.6 (c 0.455, CHCl). FABMS ($C_{23}H_{34}N_2O_5$) found 419.2 (M+H$^+$).

Boc-Pro-Ile-Phe-Oallyl 5.6

After cleavage of the Boc group from Boc-Ile-Phe-Oallyl according to general procedure D, the HCl salt of Ile-Phe-Oallyl was coupled to Boc-Pro in DMF (60 ml) via general procedure C, by using TEA (1.94 ml, 13.9 mmol), HOBt (3.047 g, 19.9 mmol), and EDCl (2.79 g. 14.6 mmol). After workup, the product was crystallized from cold EthOAc to give the title compound in 73% yield as a white solid. $R_f$=0.30 (50% EthOAc/hexane). $[\alpha]_D^{23}$=−60.5 (c 0.585, CHC$_3$). FABMS ($C_{28}H_{41}N_3O_6$) found 516.3 (M+H$^+$).

N-tert-Butoxycarbonyl-phenylalanine-N-methoxy-N-methylamide 5.2

To a solution of Boc-Phe-OH 5.1 (2.0 g, 7.53 mmol) and N,O dimethylhydroxylamine (808 mg, 8.29 mmol) in DCM (38 ml) was added TEA (2.2 ml, 15.8 mmol) and HOBT (1.27 g, 8.29 mmol). After cooling to 0° C., EDCI (1.59 g, 8.29 mmol) was added in one portion, and the reaction was stirred overnight, warming to room temperature. The reaction was concentrated in vacuo, diluted with EthOAc (150 ml), and washed with H$_2$O, 1 N KHSO$_4$, 1 N NaHCO$_3$ and brine. After drying over Na$_2$SO$_4$, filtering, and concentrating in vacuo, the residue was purified by flash chromatography to give the title compound as an oil in 88% yield. $R_f$=0.35 (50% EthOAc/hexane). $^1$H NMR (300 MHz, CDCl$_3$) δ7.28 (d, 2H, J=7.4 Hz), 7.24 (t, 1H, J=6.8 Hz), 7.17 (d, 2H, 7.1 Hz), 5.18 (d, 1H, J=7.4 Hz), 4.9 (dd, 1H, J=7.0, 11.9 Hz), 3.66 (s, 3H), 3.16 (s, 3H), 3.05 (dd, 1H, J=6.0, 13.6 Hz), 2.87 (dd, 1H, J=7.0, 13.6 Hz), 1.39 (s, 9H).

(S)-(3-(tert)-Butoxycarbonyl)amino)-4-phenyl-1-butene 5.4

A suspension of LAH (300 mg, 7.92 mmol) in THF (16 ml) at −40° C. was treated dropwise with a solution of Boc-Phe-NMe(OMe) 5.2 (2.05 g, 6.6 mmol) in THF (8 ml). The reaction was stirred at −25° C. for 1 hour and then cooled to −35° C. and quenched carefully by addition of 1 N KHSO$_4$(8 ml). The suspension was taken up in 20 ml KHSO$_4$ and extracted with Et$_2$O (3×50 ml). The organic phases were combined and washed with 10% citric acid (2×30 ml), water, 5% NaHCO$_3$ and brine, dried over Na$_2$SO$_4$, and concentrated in vacuo to give crude aldehyde 5.3. The residue was dried on the vacuum pump for 2 hours over P$_2$O$_5$ and taken directly on to the next reaction.

To a solution of TMSCH$_2$MgCl (29 ml, 1.0 M in Et$_2$O) at −78° C. was added a solution of the crude aldehyde 5.3 in THF (8 ml) via canula over 5 mm. After the grey, cloudy mixture was stirred overnight at room temperature, it was poured into a slurry of ice (25 g) and 10% citric acid (25 ml), and then extracted with Et$_2$O (3×50 ml). The organic phases were combined and washed with brine, dried over Na$_2$SO$_4$, filtered and concentrated in vacuo. After drying on the vacuum pump for 2 hours, the oil was taken up in DCM (16 ml) and cooled to 0° C. BF$_3$OEt$_2$ (3.6 ml, 29.3 mmol) was added dropwise over 5 min and the reaction mixture was stirred at room temperature for 5 days. The reaction was cooled to 0° C., quenched with 2.5 N NaOH (50 ml), and extracted with 3×DCM. The organic layers were combined, dried over Na$_2$SO$_4$, filtered, and concentrated in vacuo. The resulting brown oil was taken up in DCM (14 ml), treated with di-tert-butyl carbonate (1.18 g, 5.43 mmol) and TEA (0.076 ml, 0.543 mmol), and stirred overnight at room temperature. After washing the mixture with 10% citric acid, water, and 1 N NaHCO$_3$, it was dried over Na$_2$SO$_4$ and concentrated in vacuo. The residue was purified by flash chromatography using 4:1 hexanes/EthOAc as the eluant to give 900 mgs (57 % yield) of a white solid. R$_f$=0.20 (10% EthOAc/hexane). $^1$H NMR (300 MHz, CDCl$_3$) δ7.35–7.15 (m, SH), 5.8 (m, 1H), 5.12 (d, 1H, J=10 Hz), 5.07 (d, 1H, J=2.8 Hz), 4.40 (br s, 2H), 2.85 (d, 1H), 1.41 (s, 9H, J=5.8 Hz).

1-(R,S)-(1'(S)-(tert-Butoxycarbonylamino)-2-phenylethyl)oxirane 5.5 mCPBA (2.52 g, 14.6 mmol) was added to a solution of Boc-Phe-alkene 5.4 (900 mg, 3.64 mmol) in DCM (36 ml) and the mixture was refluxed for 20 hours. The reaction was diluted with ether and washed with sat. Na$_2$SO$_3$ (2×), 1 N NaHCO$_3$ (3×), H$_2$O, and brine, dried over Na$_2$SO$_4$, filtered, and concentrated in vacuo. The residue was purified by flash chromatography using 85:15:1 hexane/MTBE/isopropanol as the eluant to give 528 mgs (55% yield) of 5.5 as a white solid. R$_f$=0.18 (85:15:1 hexane/MTBE/isopropanol). $^1$H NMR (300 MHz, CDCl$_3$) δ7.37–7.18 (m, SH), 4.50 (br s, 1H), 4.13 (br s, 1H), 3.05–2.82 (m, 5H), 2.70 (t, 1H, J=4.2 Hz), 2.59 (br s, 1H), 1.39 (5, 9H).

Boc-Phe-(HEA)-Pro-Ile-Phe-Oallyl (SEQ. ID. NO: 22) 5.8

After cleavage of the Boc group according to general procedure D, the HCl salt of Pro-Ile-Phe-OAllyl (412 mg, 0.911 mmol) was added to a solution of Boc-Phe-epoxide 5.5 (200 mg, 0.759 mmol) and TEA (0.128 ml, 0.911 mmol) in MeOH (8 ml) and the mixture was refluxed overnight. The reaction was concentrated in vacuo and the residue was purified by flash chromatography using a 1–3% MeOH/DCM gradient as the eluant to give 396 mgs (80% yield) of 5.8 as a white solid. R$_f$=0.32 (60% EthOAc/hexane). [α]$_D^{23}$=−27.6 (c 0.66, CHCl$_3$). $^1$H NMR (300 MHz, CDCl$_3$) δ8.3–8.2 (m, 1H), 7.33–7.12 (m, 11H), 7.06–7.00 (m, 1H), 5.94–5.78 (m, 1H), 5.35–5.15 (m, 3H), 4.97–4.87 (m, 1H), 4.61 (d, 2H, J=5.8 Hz), 4.39–4.27 (m, 2H), 3.82–3.6 (m, 2H), 3.22–3.07 (m, 4H), 2.99–2.82 (m, 2H), 2.76–2.64 (m, 1H), 2.53–2.41 (m. 1H). 2.34–2.09 (m, 2H), 1.91–1.64 (m, 4H), 1.36 (s, 9H), 1.18–1.01 (m, 1H), 0.96–0.80 (m, 6H). FABMS (C$_{38}$H$_{54}$N$_4$O$_7$) found 679.4 (M+H$^+$).

Cbz-Asn(Trt)-OH 5.10

Concentrated H$_2$SO$_4$ (0.2 ml) was added to a solution of Cbz-Asn-OH (10 g, 37.6 mmol), trityl alcohol (20 g, 75.2 mmol), and acetic anhydride (7.1 ml, 75.2 mmol) in acetic acid (114 ml) and the reaction was stirred for 1 hour at 50° C. The solution was cooled and slowly added to 1.0 L of cold H$_2$O. The white precipitate was filtered, dissolved in EthOAc (250 ml), washed with H$_2$O, dried over Na$_2$SO$_4$ and filtered. The resulting white solid was crystallized from EthOAc/hexane to give 13 g (68%) of a white solid.

Cbz-Asn(Trt)-Phe-(HEA)-Pro-Ile-Phe-Oallyl (SEQ. ID. NO: 23) 5.11

After cleavage of the Boc group according to general procedure D, the Uses resulting HCl salt of Phe-(HEA)-Pro-Ile-Phe-Oallyl (188 mg, 0.306 mmol) was added to a solution of Cbz-Asn(Trt)-OH 5.10 (202 mg, 0.397 mmol), DIEA (0.069 ml, 0.397 mmol), and HOBt (70 mg, 0.52 mmol) in DMF (3 ml) and the reaction was cooled to 0° C. EDCI was added in one portion and the reaction was stirred overnight, diluted with EthOAc (50 ml), and washed with H$_2$O, KHSO$_4$, NaHCO$_3$, and brine. The organic phase was dried over Na$_2$SO$_4$, filtered and concentrated in vacuo. The residue was purified by flash chromatography using a 1–4% MeOH/DCM gradient as the eluant to give 225 mgs (68% yield) of 5.11 as a white solid. R$_f$=0.60 (90:10 DCM:MeOH). [α]$_D^{23}$=−26.3 (c 0.40, CHCl$_3$). $^1$H NMR (300 MHz, CDCl$_3$) δ8.09–8.01 (m, 1H), 7.35–7.08 (m, 30H), 6.93–6.88 (m, 1H), 6.62–6.49 (m, 1H), 6.31–6.2 (m, 1H), 5.92–5.73 (m, 1H), 5.31–5.18 (m, 2H), 5.14–4.98 (m, 2H), 4.94–4.85 (m, 1H), 4.6–4.56 (m, 2H), 4.48–4.36 (m, 1H), 4.28–4.17 (m, 1H), 4.06–3.94 (m. 1H). 3.73–3.61 (m, 1H), 3.19–3.03 (m, 4H), 2.97–2.79 (m, 2H), 2.76–2.42 (m, 4H), 2.35–2.21 (m, 1H), 2.18–1.98 (m, 2H), 1.89–1.56 (m, 4H), 1.45–1.31 (m, 1H), 1.04–0.97 (m, 1H), 0.93–0.80 (m, 6H). FABMS (CHNO) found 1069.5 (M+H$^+$).

CS-131-(MeLeu(3-OH))$^1$, (D)MeSer$^3$, Lys$^7$)CsA Conjugate 2.8

A solution of Cbz-Asn(Trt)-Phe-(HEA)-Pro-Ile-Phe-Oallyl 5.11 in THF/MeOH (1:1) was treated with LIOH (aq) and the reaction was stirred for 3 hours at room temperature. After the reaction was concentrated in vacuo. the residue was dissolved in H$_2$O, acidified with 1 N HCl, and extracted with DCM. The combined organic layers were dried over Na$_2$SO$_4$, filtered, and concentrated in vacuo to give crude acid 5.12.

A solution of the trityl-protected acid 5.12 in DCM (2 ml) was treated with TFA (0.5 ml) and the reaction was stirred 1 hour at room temperature and then concentrated in vacuo. The residue was concentrated several times from ether, suspended in ether, and filtered to remove the tritylmethane and trityl alcohol. Concentration of the filtrate gave the fully deprotected inhibitor 5.13 which was used in the next reaction without any further purification.

A solution of the fully deprotected inhibitor 5.13 (42 mg, 0.047 mmol) and the free amine CsA analog 4.11 (58 mg, 0.047 mmol, produced from 4.20 via general procedure K) in DMF/acetonitrile (1:1, 1 ml) was treated with PyAOP (27 mg, 0.052 mmol) and DIEA (0.017 ml, 0.099 mmol), stirred overnight at room temperature, and concentrated in vacuo. The residue was diluted with EthOAc, washed with brine (with a few drops of 1 N NaHCO$_3$ added), dried over Na$_2$SO$_4$, and concentrated in vacuo, to an oil which was purified by flash chromatography (2–4–6% MeOH/DCM) to give 45 mg (47% yield) of conjugate 2~. $R_f$=0.45 (9:1 DCM/MeOH). FABMS found 2019.1 [M+H$^+$].

Example 4

Synthesis of Pyrone Inhibitors and Pyrone Conjugates 1-(TBS)-3-(tert)-Butyl-hydroquinone 6.2

To a solution of t-butyl hydroquinone (3.0 g, 18 mmol) in DCM (60 ml) was added TBS-Cl (2.71 g, 18 mmol) and imidazole (1.22 g, 18 mmol). The reaction was stirred for 2 hours at room temperature, washed with KHSO$_4$ and brine, dried over Na$_2$SO$_4$, filtered, and concentrated in vacuo. The residue was purified by flash chromatography (10% Et$_2$O/hexane) to give 4.9 g (97% yield) of an off-white solid. $R_f$ 0.34 (20% Et$_2$O/hexane). $^1$H NMR (300 MHz, CDCl$_3$) δ6.59 (d, 1H, J=2.3 Hz), 6.37–6.33 (m, 2H), 4.33 (s, 1H), 1.21 (s, 9H), 0.81 (s, 9H), 0.00 (s, 6H). $^{13}$C NMR (75.5 MHz, CDCl$_3$) δ149.0, 148.4, 137.1, 118.9, 117.4, 116.9, 34.5, 29.5, 25.8, 18.2, −4.5. HR-EI: calculated for C$_{16}$H$_{28}$O$_2$Si 280.1858, found 280.1860.

1-(TBS)-3-(tert)-butyl-4-N,N-(dimethyl) thiocarbamoylhydroquinone 6.3

A solution of 1-(TBS)-3-tert-butyl-hydroquinone 6.2(2.93 g, 10.4 mmol) in THF (75 ml) was treated with NaH (479 mgs, 12.5 mmol of a 60% dispersion in mineral oil) and the mixture stirred for 1 hour at room temperature. N,N dimethylthiocarbamoyl chloride (1.55 g, 12.5 mmol) was then added in one portion to the solution and the resulting mixture was stirred overnight at room temperature. After quenching the reaction with 1 N KHSO$_4$, it was diluted with EthOAc (150 ml), washed with brine, KHSO$_4$, NaHCO$_3$, brine, dried over Na$_2$SO$_4$, filtered and concentrated in vacuo. The residue was purified by flash chromatography (10% Et$_2$O/hexane) to give 2.03 g (52% yield) of an off-white solid. $R_f$ 0.32 (20% Et$_2$O/hexane). $^1$H NMR (300 MHz, CDCl$_3$) δ6.84 (d, 1H, J=8.7 Hz), 6.82 (d, 1H, J=2.8 Hz), 6.65 (dd, 1H, J=2.9, 8.7 Hz), 3.49 (s, 1H), 3.36 (s, 1H), 1.32 (s, 9H), 0.97 (s, 9H), 0.20 (s, 6H). $^{13}$C NMR (75.5 MHz, CDCl$_3$) δ188.3, 152.9, 146.5, 142.1, 125.9, 118.3, 117.2,43.4, 38.8, 34.5, 30.6, 25.7, 18.2, −4.4. HR-EI: calculated for C$_{19}$H$_{33}$NO$_2$SiS 367.2001, found 367.2008.

1-(TBS)-3-ter-Butyl-4N,N-dimethycarbamoylthiohydroquinone 6.4

A sand bath was heated to 275–300° C. and a 2.5 ml flask containing neat 1-(TBS)-3-tert-butyl-4N,N-dimethylthiocarbamoylhydroquinone 6.3 (1.98 g, 5.39 mmol) and fitted with a vigereaux column was immersed in the sand for 20 minutes. After allowing the brown/black solution to cool to room temperature, it was purified. by flash chromatography (10–20% Et$_2$O/hexane gradient of 5%) to yield 1.36 g (69% yield) of 6.4 as a yellow oil. $R_f$ 0.22 (20% Et$_2$O/hexane). $^1$H NMR (300 MHz, CDCl$_3$) δ7.36–7.25 (m, 1H), 6.92 (d, 1H J=2.6 Hz), 6.68 (dd, 1H J=2.6, 8.4 Hz), 3.07 (bs, 6H), 1.43 (m, due to multiple conformers, 9H), 0.98 (m, due to multiple conformers, 9H), 0.21 (m, due to multiple conformers, 6H). $^{13}$C NMR (75.5 MHz, CDCl$_3$) δ167.8, 156.7, 154.6, 142.6, 118.9, 118.7, 117.7, 37.0, 36.3, 30.8, 25.7, 18.2, −4.3. HR-EI: calculated for C$_{19}$H$_{33}$NO$_2$SiS 367.2001, found 367.2009.

3-tert-Butyl-4-N,N-dimethycarbamoylthiohydroquinone 6.9

A solution of 1-(TBS)-3-tert-butyl-4-N,N-dimethylcarbamoylthiohydroquinone (1.36 g, 3.71 mmol) 6.4 in THF (24 ml) was treated with TBAF (4.44 ml, 1 N THF) and the reaction was stirred for 0.5 hours. After diluting the solution with EthOAc (50 ml), it was washed with KHSO$_4$ and brine, dried over Na$_2$SO$_4$, filtered, and concentrated in vacuo. The residue was purified by flash chromatography (30–50% EthOAc/hexane, 10% increments) to give 861 mgs (92% yield) of an off-white solid. $R_f$ 0.13 (20% Acetone/hexane). $^1$H NMR (300 MHz, CDCl$_3$) δ7.48 (bs, 1H), 7.15–7.08 (m, 1H), 6.81 (d, 1H, J=2.7 Hz), 6.29 (dd, 1H, J=2.7, 8.3 Hz), 3.25–2.95 (m, 6H), 1.41 (s, 9H). $^{13}$C NMR (75.5 MHz, CDCl$_3$) δ170.1, 158.0, 154.5, 142.3, 115.6, 115.3, 114.5, 37.2, 36.3, 30.8. HR-EI: calculated for C$_{13}$H$_{19}$NO$_2$S 253.1136, found 253.1132.

1-Allyl-3-tert-butyl-4-N,N-dimethycarbamoylthiohydroquinone 6.13

Method 1: 3-(Tert)-butyl-4-N,N-diinethylcarbainoylthiohydroquinone 6.9(861 mg, 3.41 mmol) was dissolved in THF (34 ml) and the solution was cooled to 0° C. NaH was added in portions (196 mgs, 5.11 mmol, 60% dispersion in mineral oil) and the resulting slurry was stirred for 10 min at room temperature. The solution was treated with allyl iodide (0.624 ml, 6.82 mmol), stirred 48 hours, diluted with EthOAc (75 ml) and washed with brine, KHSO$_4$, dried over Na$_2$SO$_4$, and concentrated in vacuo. The residue was purified by flash chromatography (20% EthOAc/hexane) to give 843 mgs (85% yield) of an oil.

Method 2: 3-tert-butyl-4-N,N-dimethycarbamoylthiohydroquinone 6.9 (370 mg, 1.47 mmol), K$_2$CO$_3$ (812 mg, 5.87 mmol), and allyl bromide (0.133 ml, 1.62 mmol) were dissolved in acetone (7.5 ml) and refluxed for 10 hours. After cooling the reaction to room temperature, it was diluted with EthOAc (25 ml), washed with brine, dried over Na$_2$SO$_4$, and concentrated in vacuo. The residue was purified by flash chromatography (20% EthOAc/hexane) to give 352 mgs (82% yield) of an oil. $R_f$ 0.19 (20% EtOAc/hexane). $^1$H NMR (300 MHz, CDCl$_3$) δ7.36 (d, 1H, J=8.5 Hz), 7.05 (d, 1H, J=2.8 Hz), 6.78 (dd, 1H, J=2.8, 8.5 Hz), 6.14–5.98 (m, 1H), 5.47–5.37 (m, 1H), 5.34–5.25 (m, 1H), 4.58–4.51 (m, 2H), 3.07 (bs, 6H), 1.45 (s, 9H). $^{13}$C NMR C75.5 MHz, CDCl$_3$) δ167.9, 159.5, 154.7, 142.7, 133.2, 118.4, 117.9, 115.0, 111.4,68.8, 37.0, 36.5, 30.8. HR-EI: calculated for C$_{16}$H$_{23}$NO$_2$S 293.1449, found 293.1440.

1-(Thiotoluenesufonate)-2-tert-butyl-4(hydroxy(3-propene))-benzene 6,14

A solution of 1-allyl-3-tert-butyl-4N,N- dimethylcarbamoylthiohydroquinone (843 mgs, 2.88 mmol) 6.13 in THF (20 ml) was cooled to 0° C. and treated with LiAlH$_4$ (6.06 ml, 1.0 N THF) dropwise. The reaction mixture was allowed to warm room temperature over 5 hours, cooled back to 0° C., and quenched with KHSO$_4$ (50 ml) very carefully. The mixture was extracted with Et$_2$O, the phases were separated, and the organic layer was washed with brine, dried over Na$_2$SO$_4$, filtered, and concentrated in vacuo to give a free thiol which was used crude in the next reaction.

To a solution of toluenesufonyl bromide (813 mgs, 3.46 mmol) and TEA CO.480 ml, 3.46 mmol) in CCl$_4$ (22 ml) cooled to 0° C., was added dropwise a solution of the crude thiol in CCl$_4$ (7.2 ml). After stirring for 5 min, the reaction was diluted with DCM (60 ml), washed with KHSO$_4$, NaHCO$_3$ brine, dried over Na$_2$SO$_4$, filtered and concentrated in vacuo. The residue was purified by flash chromatography (10% Et$_2$O/hexane) to give 940 mgs (87% yield) of the thiosulfonate 6.14. $R_f$ 0.32 (15% EtOAc/hexane). $^1$H NMR (300 MHz, CDCl$_3$) δ7.56 (d, 1H, J=8.6 Hz), 7.46 (d, 2H, J=8.4 Hz), 7.21 (d, 2H, J=8.0 Hz), 6.99 (d, 1H, J=2.8 Hz), 6.45 (dd, 1H, J=2.8, 8.6 Hz), 6.15–6.09 (m, 1H), 5.45 (dd, 1H, J=17.3, 1.5 Hz), 5.33 (dd, 1H, J=10.48, 1.5 Hz), 4.60–4.53 (m, 2H), 2.41 (s, 3H), 1.18 (s, 9H). $^{13}$C NMR (75.5 MHz, CDCl$_3$) δ166.7, 160.6, 155.3, 144.6, 141.4, 140.8, 132.7, 129.5, 127.7, 118.3, 117.8, 115.6, 111.2, 68.9, 36.7, 31.0, 21.6. HR-EI: calculated for $C_{20}H_{24}O_3S_2$ 376.1167, found 376.1157.

4-Hydroxy-pyran-2-one 6.6

A solution of phenyltrimethylsilylenol ether (5 ml, 26 mmol) in Et$_2$O (16 ml) at −20° C. was treated with a solution of malonyl dichloride (0.842 ml, 8.66 mmol) in Et$_2$O (4 ml) via canula. After allowing the reaction to warm to room temperature overnight, it was diluted with Et$_2$O (50 ml) and extracted with Na$_2$CO$_3$ (3×50 ml). The combined aqueous phases were then washed with Et$_2$O (3×50 ml), acidified with conc. HCl, and extracted with Et$_2$O to give 1.06 g (66% yield) of an orange solid. HR-EI calculated for $C_{11}H_8O_3$ 188.0473, found 188.0477.

Allyl-protected Pyrone HIV Protease Inhibitor 6.15

A solution of the pyrone 6.6 (600 mgs, 3.19 mmol) and NaOH (3.2 ml, 1 N aqueous) in ethanol (18 ml) was heated in a flask fitted with a water condensor until the pyrone was completely dissolved. To the warm reaction mixture was added dropwise a solution of the thiosulfonate 6.14 (940 mgs, 2.5 mmol) in ethanol (7 ml). After refluxing the reaction mixture overnight, it was cooled to room temperature and concentrated in vacuo. The residue was acidified with 3N HCl and extracted with DCM (3×50 ml). The organic layers were combined, dried over Na$_2$SO$_4$ filtered, concentrated in vacuo, and purified by flash chromatography (80:20 hexane/EthOAc, then 30:65:15 hexane/EthOAc/DCM, and 50:45:15 hexane/EthOAc/DCM) to give 455 mgs (45% yield) of 6.15 as a yellow foam. $R_f$=0.53 C65:30:5 DCM/EthOAc/Hexane) $^1$H NMR (300 MHz, CDCl$_3$) δ7.91–7.68 (m, 3H), 7.55–7.42 (m, 3H), 7.01 (d, 1H, J=2.8 Hz), 6.95 (d, 1H, J=8.7 Hz), 6.71 (s, 1H), 6.61 (dd, 1H, J=8.7, 2.8), 6.02 (m, 1H), 5.38 (dd, 1H, J=17.3, 1.5 Hz), 5.27 (dd, 1H, J=10.5, 1.35 Hz), 4.48 (dt, 2H, J=13.5, 5.4 Hz), 1.60 (s, 9H). HR-EI: calculated for $C_{24}H_{24}O_4S$ 408.1395, found 408.1429.

Tert-Butyl Acetoxy Pyrone HIV Protease Inhibitor 2.4

A solution of the allyl-protected pyrone HIV protease inhibitor 6.15 (132 mgs, 0.324 mmol), acetic acid (0.021 ml, 0.357 mmol), and Pd(PP$_3$)$_4$ (37 mgs, 0.0032 mmol) in DCM (1.9 ml) was treated with SnBu$_3$H (0.96 ml, 0.357 mmol) quickly in one portion. The reaction was stirred for 15 minutes, changing from yellow to green to green-black, at which point TLC showed consumption of starting material. The reaction mixture was diluted with DCM (10 ml) and extracted with 10% Na$_2$CO$_3$ (3×20 ml). The aqueous layers were combined, washed with Et$_2$O (2×), acidified to pH 2 with conc. HCl, and extracted with DCM (3×). The organic layers were combined, dried over Na$_2$SO$_4$, and concentrated in vacuo to give 92 mgs (77% yield) of 6.16 as a yellow solid 95% clean by TLC, which was taken directly on to the next reaction.

To a solution of pyrone hydroxyl 6.16 (50 mg, 0.136 mmol) in THF (1 ml) cooled to 0° C. was added tBuOK (32 mg, 0.285 mmol). After stirring for 5 minutes, t-butylchloroacetate (0.041 ml, 0.285 mmol) and tetrabutylammonium iodide (cat.) were added and the reaction was stirred for 5 hours warming to room temperature. The reaction was concentrated in vacuo, brought up in H$_2$O (5 ml), acidified to pH 3 with 1 N KHSO$_4$, and extracted with DCM (5×15 ml). The organic layers were combined, dried over Na$_2$SO$_4$, filtered, concentrated in vacuo, and purified by flash chromatography (40:55:5 EthOAC/hexane/DCM) to give 30 mgs (45% yield) of 2.4 as a yellow foam. $R_f$=0.34 (65:30:5 DCM/EthOAc/hexane). $^1$H NMR (300 MHz, CDCl$_3$) δ7.92–7.68 (m, 3H), 7.54–7.43 (m, 3H), 7.03 (d, 1H, J=2.8 Hz), 6.95 (d, 1H, J=8.7 Hz), 6.72 (s, 1H), 6.56 (dd, 1H, J=8.7, 2.8 Hz), 4.45 (s, 2H), 1.59 (s, 9H), 1.48 (s, 9H). FABMS: found 482.2 (M+H$^+$).

Acetoxy Acid HIV Protease Inhibitor 6.23

A THF (1 ml) solution of the tert-butyl acetoxy pyrone inhibitor 2.4 (26 mg, 0.0539 mmol) was treated with LiOH (0.162 ml, 1 N LiOH) and stirred over night at room temperature. An additional equivalent of LiOH was added and the solution was stirred another hour. The reaction was concentrated in vacuo, diluted with water, acidified with 1 N KHSO$_4$, and extracted with DCM and EthOAc. The combined organic layers were dried over Na$_2$SO$_4$, filtered, and concentrated in vacuo to give 22 mg (99% yield) of the acid 6.23 $R_f$=0.29 C95:4:1 DCM/MeOH/HOAc). $^1$H NMR (300 MHz, CDCl$_3$) δ7.82–7.70 (m, 2H), 7.48–7.35 (m, 3H), 6.95 (d, 1H, J=2.8 Hz), 6.90 (d, 1H, J=8.7 Hz), 6.63 (s, 1H), 6.49 (dd, 1H, J=8.7, 2.8 Hz), 4.45 (s, 2H), 3.85 (bs, 1H), 1.50 (s, 9H).

Boc-aminohexyl Acetoxy Amide Pyrone 6.24

The pyrone acid 6.23 (10 mg, 0.0234 mmol) and tert-butyl N-(aminohexyl)-carbamate hydrochloride (6.5 mg, 0.0258 mmol) in THF (0.5 ml) were treated sequentially with BOP (11 mg, 0.0258 mmol), NMM (0.011 ml, 0.0725 mmol). and then stirred overnight at room temperature. The reaction was diluted with EthOAc, washed with 10% KHSO$_4$ and brine, dried over Na$_2$SO$_4$, filtered, and concentrated in vacuo. The residue was purified by flash chromatography (1% MeOH/DCM) to give 10 mg (68% yield) of the tide compound. $R_f$=0.48 (95:5 DCM/MeOH). $^1$H NMR (300 MHz, CDCl$_3$) δ7.85–7.74 (m, 2H), 7.48–7.32 (m, 3H), 6.96 (d, 1H, J=2.8 Hz), 6.89 (d, 1H, J=8.7 Hz), 6.67 (s, 1H), 6.52 (dd, 1H, J=8.7,2.8 Hz), 4.35 (s, 2H), 3.26 (t, 1H, J=6.6 Hz), 3.24 (t, 1H, J=6.6 Hz), 3.08–2.97 (m, 2H), 1.6–1.15 (m, 8H), 1.53 (s, 9H), 1.37 (s, 9H).

Pyrone HIV Protease Inhibitor-(MeLeu(3-OH)[1], DMeSer[3], Lys[7])-CsA Conjugate 2.9

A solution of the pyrone acid 6.23 (20 mg, 0.0469 mmol) and the CsA analog free amine 4.11 (53 mg, 0.0427 mmol, produced from 4.20 via general procedure K) in THF (1 ml) were treated sequentially with PyAOP (24 mg, 0.0469 mmol), NMM (0.16 ml, 0.09 mmol), and then stirred overnight at room temperature. The reaction was diluted with EthOAc, washed with 10% KHSO$_4$, brine, dried over Na$_2$SO$_4$, filtered, and concentrated in vacuo. The residue was purified by flash chromatography (2–4–6% MeOH/DCM) to give 40 mg (56% yield) of conjugate 2.9. $R_f$=0.48 (90:10 DCM/MeOH). FABMS found 1657.7 (M+H$^+$).

Aminohexyl acetoxy amide pyrone-OL-17 semi-synthetic conjugate 2.12

A solution of aminohexyl acetoxy amide pyrone HCl salt (produced from 6.24 by general procedure D) (15 mg, 0.024 mmol), TEA (0.004 ml, 0.0288 mmol) and OL-17 p-nitrophenol carbonate 8.3 (15 mg, 0.0108 mmol, see CsA analog synthetic procedures) in DMF (0.5 ml) were stirred overnight at room temperature. The reaction was concentrated in vacuo and purified by flash chromatography (2–3–5% MeOH/DCM) to give 5 mg (28% yield) of conjugate 2.12. $R_f$=0.55 (90:10 DCM/MeOH). FABMS found 1768.8 (M+H$^+$).

Example 5

Synthesis of VX-478 Analogs and Conjugates (3S,4S)-N-Boc-4-amino-3-hydroxy-5-(4-benzyloxyphenyl)-1-pentene 7.15

A solution of Boc-Tyr(OBn)-OH 7.13 (5g, 13.5 mmol) in DMF (27 ml) was treated with $Cs_2CO_3$ (8.8 g, 27 mmol) and iodomethane (0.840 ml, 13.5 mmol) and the mixture was overnight at room temperature. The reaction was then diluted with EthOAc (100 ml), and washed with $H_2O$, 1 N $NaHCO_3$, and brine. The organic phase was dried over $Na_2SO_4$, filtered, concentrated in vacuo to give methyl ester 7.14, which was dried over $P_2O_5$ on high-vacuum overnight.

Methyl ester 7.14 was dissolved in toluene (dried over sieves) and cooled to −78° C. and DIBAL (18.5 ml, 1 M in toluene) was added dropwise over 40 minutes. After stirring for 5 minutes at −78° C., vinylmagnesiumn bromide (71.2 ml, 1 M in THF) was added and the reaction mixture was stirred at 0° C. overnight. The reaction was cautiously quenched with methanol, then treated with aqueous Rochelle salts, stirred for a few minutes, and filtered. The filtrate was washed with brine, dried over $Na_2SO_4$, and concentrated in vacuo. The residue was purified by flash chromatography (10–15–20–30% EthOAc/hexane) to give 2.36 g (47% yield) of the (3S,4S) allylic alcohol 7.15 and 664 mg (13% yield) of the (3R,4S) allylic alcohol 7.16.

Data for (3S,4S) diastereomer 7.15: $R_f$=0.35 (40% EtOAc/hexane). $[\alpha]_D^{23}$=−43.8 (c 0.455, CHCl$_3$). $^1$H NMR (300 MHz, CDCl$_3$) δ7.48–7.27 (m, SH), 7.15 (d, 2H, J=8.6 Hz), 6.93 (d, 2H, J=8.6 Hz), 5.88 (m, 1H), 5.28 (m, 1H), 5.18 (m, 1H), 5.03 (s, 2H), 4.78 (m, 1H), 4.11 (bs, 1H), 3.76 (m, 1H), 2.94–2.75 (m, 2H), 2.28 (bs, 1H), 1.39 (s, 9H). $^{13}$C NMR: CDCl$_3$) δ157.5, 138.4, 137.1, 130.6, 130.3, 128.6, 127.9, 127.5, 116.1, 114.9, 79.5, 72.7, 70.0, 37.1, 28.3. FABMS ($C_{23}H_{29}NO_4$) found 384.2 (M+H~). Data for (3R, 4S) diastereomer 7.16: $R_f$ 0.32 (40% EtOAc/hexane). $[\alpha]_D^{23}$=−17.09 (c 0.515, CHCl$_3$). $^1$H NMR (300 MHz, CDCl$_3$) δ7.46–7.28 (m, 5H), 7.10 (d, 2H, J=8.7 Hz), 6.91 (d, 2H, J=8.7 Hz), 5.93 (m, 1H), 5.36 (m, 1H), 5.27 (m, 1H), 5.04 (s, 2H), 4.56 (m, 1H), 4.21 (bs,. 1H), 3.93 (bs, 1H), 3.03 (bs, 1H), 2.83–2.60 (m, 2H), 1.37 (s, 9H) $^{13}$C NMR: CDCl$_3$) δ157.5, 137.1, 136.9, 130.2, 128.6, 127.9, 127.5, 117.0, 114.9, 79.8, 74.7, 70.0, 56.6, 35.2, 28.3. FABMS $C_{23}H_{29}NO_4$) found 384.2 (M+H$^+$).

(2S,3S)-N-Boc-3-amino-1,2-epoxy-4-(4-hydroxypbenyl)butane 7.19

A solution of 7.15 (3.05 g, 8.07 mmol) and TEA (4.5 ml, 31.8 mmol) in DCM (66 ml) was cooled in an acetone/ice bath under argon and treated dropwise with methanesulfonyl chloride (1.24 ml, 16 mmol). The reaction was stirred 15 minutes, quenched with 10% citric acid (75 ml), and extracted with ether (2×100 ml). The organic layers were combined, washed with $H_2O$ and brine, dried over $Na_2SO_4$, and concentrated in vacuo to give an 3.55 g of 7.17 as an off-white solid which was used crude in the next reaction. $R_f$ 0.10 (40% EtOAc/hexane). $[\alpha]_D^{23}$=−41.4 (c 0.500, CHCl$_3$). 1H NMR (300 MHz, CDCl$_3$) δ7.45–7.28 (m, SH), 7.16 (d, 2H, J=7.7 Hz), 6.92 (d, 2H, J=8.6 Hz), 5.93 (m, 1H), 5.46 (d, 1H, J=12.9 Hz), 5.40 (d, 1H, J=7.8 Hz), 5.04 (s, 2H), 4.68 (d, 1H, J=9.3 Hz), 4.03 (bs, 1H), 3.05 (s, 3H), 2.88 (dd, 1H, J=13.8, 6.4 Hz), 2.75 (dd, 1H, J=13.8, 7.0 Hz), 1.38 (s, 9H).

A solution of the crude mesylate 7.17 (3.55 g) was dissolved in DCM:MeOH (60 ml:10 ml) and cooled to −78° C. Ozone was bubbled through the solution until a blue color persisted (ca. I hr). The reaction was purged with argon and $NaBH_4$ (1.02 g, 27 mmol) was added. After stirring the reaction at room temperature for 3 hr, it was quenched dropwise with I N HCl. The mixture was diluted with ether, washed with I N $NaHCO_3$, $H_2O$, and brine, dried over $Na_2SO_4$, filtered, and concentrated in vacuo to give alcohol 7.18 as a white solid (2.56 g, 70%) which was of sufficient purity to use in the next reaction after drying. $^1$H NMR (300 MHz, CDCl$_3$) δ7.47–7.28 (m, 5H), 7.15 (d, 2H, J=8.5 Hz), 6.92 (d, 2H, J=8.6 Hz), 5.03 (s, 2H), 4.73 (t, 1H, J=6.53 Hz), 4.66 (d, 1H, J=9.5 Hz), 4.21 (m, 1H), 3.82 (dd, 1H, J=12, 6.5 Hz), 3.65 (dd, 1H, J=12, 7 Hz), 3.37 (m, 1H), 3.09 (s, 3H), 2.94–2.73 (m, 2H), 1.38 (s, 9H).

The alcohol mesylate 7.18 (2.55 g, 5.46 mmol) was dissolved in THF (55 ml) and treated with NaH (0.209 mg, 5.46 mmol, 60% dispersion in mineral oil) in portions. The reaction was stirred at room temperature for 1 hr, refluxed for 1 hr, and then cooled to 0° C. and quenched carefully with $NH_4Cl$. After diluting the mixture with ether, it was washed with 1 N $NaHCO_3$ and brine, dried over $Na_2SO_4$, filtered, and concentrated in vacuo. The residue was purified by flash chromatography (20–30% EthOAc/hexane) to give 1.74 g (86% yield) of 7.19 as a white solid. $R_f$0.4 (40% EtOAc/hexane). $[\alpha]_D^{23}$ =+7.9 (c 0.57, CHCl$_3$). $^1$H NMR (300 MHz, CDCl$_3$) δ7.46–7.29 (m, 5H), 7.14 (d, 2H, J=8.6), 6.93 (d, 2H, J=8.6), 5.05 (s, 2H), 4.41 (bs, 1H), 3.63 (bs, 1H), 2.96–2.71 (m, 5H), 1.39 (s, 9H). $^{13}$C NMR: (CDCl$_3$) δ155.3, 130.5, 128.6, 128.0, 127.5, 114.9, 70.0, 53.2, 46.9, 36.7, 28.3. FABMS ($C_{22}H_{27}NO_4$) found 370.2 (M+H$^+$).

(2S,3S)-N-Boc-3-amino-2-hydroxy-4-(4-hydroxyphenyl)-1-isobutylaminobutane 7.20

A solution of the epoxide (800 mg, 2.15 mmol) and isobutylamine (4.27 ml, 43 mmol) in methanol (11 ml) were stirred at RT for 4 hours. After concentrating the residue from ether (4x) and DCM (4x) until TLC showed the complete disappearance of the isobutylamine, the white foam was dried on high vacuum for 2 hours and used directly in the next reaction without further purification.

The benzyl-protected hydroxyethylamine was dissolved in methanol (11 ml) and hydrogenated (1 atm) over Pd(OH)$_2$ (80 mg) for 2 hours, at which time TLC showed the disappearance of starting material. After filtering through celite and concentrating in vacuo. the residue was purified by flash chromatography (small plug of silica, 10% MeOH/DCM) to give 558 mgs (74% yield) of 7.20 as a white foam. Usually the crude product was of sufficient purity (by TLC and $^1$H NMR) to use in the next reaction without purification by flash chromatography. $[\alpha]_D^{23}$+9.300 (c 0.57, CHCl$_3$). $^1$H NMR (300 MHz, CDCl$_3$) δ7.03 (d, 2H, J=8.1 Hz), 6.70 (d, 2H, J=8.1 Hz), 4.77 (bs, 1H), 4.18 (bs, 1H), 3.78 (bs, 1H), 3.50 (bs, 1H), 2.82 (m, 2H), 2.71 (m, 2H), 2.45 (m, 2H), 1.79 (m, 1H), 1.39 (s, 9H), 0.92 (d, 6H, J=6.6 Hz). $^{13}$C NMR: (CDCl$_3$) δ156.3, 154.9, 130.5, 115.5, 70.4, 57.8, 35.6, 28.3, 28.0, 20.5. FABMS ($C_{19}H_{32}N_2O_4$) found 353.2.

(2S,3S)-N-Boc-3-amino-2-hydroxy-4-(4-t-butyldimethylsilyloxyphenyl)-1-N-(4carbobenzyloxyaminophenylsulfonyl)-(isobutyl) aminobutane 7.23

A solution of hydroxyethylamine 7.20 (208 mg, 0.59 mmol) and TBS-Cl (179 mg, 1.18 mmol) in THF (5.9 ml)

was treated with imidazole (80 mg, 1.18 mmol) and the mixture was stirred for 2 hours at room temperature. After diluting with EthOAc (25 ml), the solution was washed with brine (2x), dried over $Na_2SO_4$, filtered, and concentrated in vacuo. The residue was dissolved in THF (5.9 ml) and NMM (0.200 ml, 1.83 mmol) and 4-((carbobenzyloxy)-amino)-phenylsulfonyl chloride (211 mg, 0.648 mmol) was added to the reaction mixture. After stirring overnight at room temperature, the reaction was diluted with EthOAc (25 ml), washed with $KHSO_4$, $NaHCO_3$, $H_2O$ and brine, and the phases were separated the organic layer was dried over $Na_2SO_4$, filtered, and concentrated in vacuo, and the residue was purified by flash chromatography (30% EthOAc/hexane) to give 258 mgs (59% yield) of 7.23 as a white foam. $R_f0.47$ (40% EtOAc/hexane). $[\alpha]_D^{23}$=+26.7 (c 0.58, $CHCl_3$). $^1H$ NMR (300 MHz, $CDCl_3$) δ7.53 (d, 2H, J=8.8 Hz), 7.34 (d, 2H, J=8.8 Hz), 7.26–7.16 (m, 5H), 6.91 (d, 2H, J=8.4 Hz), 6.76 (s, 1H), 6.59 (d, 2H, J=8.4 Hz), 5.05 (s, 2H), 4.47–4.35 (m, 1H), 3.72 (bs, 1H), 3.65–3.45 (m, 2H), 2.95–2.85 (m, 2H), 2.82–2.58 (m, 4H), 1.65 (m, 1H), 1.18 (s, 9H), 0.80 (s, 9H), 0.71 (d, 3H, J=6.61 Hz), 0.68 (d, 3H, J=6.6 Hz), 0.00 (s, 6H). $^{13}C$ NMR:($CDCl_3$) δ130.4, 128.8, 128.7, 128.6, 128.4, 120.1, 118.1, 67.5, 28.3, 27.1, 25.7, 20.1, 19.9. FABMS ($C_{39}H_{57}N_3O_8SiS$) found 756 (M+H$^+$).

(2S, 3S)-N-Boc-3-amino-2-hydroxy-4-(4-ethylacetoxyphenyl)-1-N-(4-carbobenzyloxyaminophenylsulfonyl)-isobutylaminobutane 7.24

A solution of 7.23 (248 mg, 0.327 mmol) in THF (5.5 ml) was treated with HF/pyridine (4.5 ml of a stock solution prepared from 1 g HF/pyridine, 2 ml pyridine, and 8 ml THF). After stirring the reaction mixture at room temperature for 2.5 hours, at which time TLC indicated complete disappearance of starting material, the reaction was added dropwise to a solution of $NaHCO_3$ (50 ml). The mixture was extracted with DCM (3x25 ml), and the combined organic phases were washed with $KHSO_4$ and brine, dried over $Na_2SO_4$, filtered, and concentrated in vacuo. The residue was dissolved in dioxane (3.3 ml) and $Cs_3CO_3$ (425 mg, 1.31 mmol) and ethyl bromoacetate (0.218 ml, 1.96 mmol) was added to the reaction mixture. The reaction was stirred at 40–50° C. until TLC showed complete disappearance of starting material (ca. 3 hours), and then diluted with EthOAc. The mixture was washed with $KHSO_4$ and brine, dried over $Na_2SO_4$, filtered, and concentrated in vacuo. The residue was purified by flash chromatography (30–40–50% EthOAc/hexane) to give 170 mgs (71% yield) of a foam. $R_f0.25$ (40% EtOAc/hexane). $[\alpha]_D^{23}$=+11.960 Cc 0.46, $CHCl_3$). $^1H$ NMR (300 MHz, $CDCl_3$) δ7.64 (d, 2H, J=8.8 Hz), 7.54 (d, 2H, J=8.8 Hz), 7.43–7.34 (m, 5l-I), 7.21 (s, 1H), 7.17 (d, 2H, J=8.6 Hz), 6.84.(d, 2H, J=8.6 Hz), 5.28 (s, 2H), 4.67 (m, 1H), 4.59 (s, 2H), 4.25 (q, 2H, J=7.1 Hz), 3.89–3.65 (m, 3H), 3.10–2.83 (m, 5H), 2.76 (dd, 1H, J=13.6, 7.0 Hz), 1.84 (m, 1H), 1.37 (s, 9H), 1.27 (t, 3H, J=7.13 Hz), 0.90 (d, 3H, J=6.6 Hz), 0.85 (d, 3H J=6.6 Hz). FABMS $C_{37}H_{49}N_3O_{10}S$) found 727 (M+H$^+$).

N-{(S)-3-hydroxytetrahydrofuryloxycarbonyl}-(2S, 3S)-3-amino-2-hydroxy-4-(4-ethylacetoxyphenyl)-1-N-(4-carbobenzyloxyaminophenylsulfonyl)-isobutylaminobutane 7.25

The Boc group was cleaved from hydroxyethylamine 7.24 (150 mg, 0.206 mmol) in HCl/dioxane (3 ml, 4 N) via general procedure D to give the HCl salt. A solution of the HCl salt in 50:50 dioxane/$CH_3CN$ (3 ml) was treated with TEA (0.068 ml, 0.618 mmol) and 3(S)-tetrahydrofuryl p-nitrophenolcarbonate (57 mg, 0.226 mmol) and the reaction was stirred at room temperature for 1 hour and then at 50° C. for 2 hours. After diluting with EthOAc (25 ml), the solution was washed with $NaHCO_3$ (10x), $KHSO_4$ (2x), an brine (2x), dried over $Na_2SO_4$, filtered, and concentrated in vacuo. The residue was purified by flash chromatography (30–40–50% EthOAc/hexane) to give 90 mgs (59% yield) of 7.25 as a white foam. $R_f0.38$ (70% EtOAc/hexane). $[\alpha]_D^{23}$=+2.710 (c 1.07, $CHCl_3$). $^1H$ NMR (300 MHz, $CDCl_3$) δ7.64 (d, 2H, J=8.8 Hz), 7.55 (d, 2H, J=9.0 Hz), 7.44–7.34 (m, 5H), 7.28 (s, 1H), 7.14 (d, 2H, J=8.5 Hz), 6.83 (d, 2H, J=8.6 Hz), 5.22 (s, 2H), 5.14 (bs, 1H), 4.90 (m, 1H), 4.59 (s, 2H), 4.25 (q, 2H, J=7.1 Hz), 3.90–3.73 (m, 6H), 3.69 (d, 1H, J=11.5 Hz), 3.13–2.82 (m, 5H), 2.74 (dd, 1H, J=13.3, 6.4 Hz), 2.10 (m, 1H), 1.95 (m, 1H), 1.82 (m, 1H), 1.28 (t, 3H, J=7.1 Hz), 0.90 (d, 3H, J=6.5 Hz), 0.86 (d, 3H, J=6.6 Hz). FABMS $C_{37}H_{47}N_3O_{11}S$) found 742 (M+H$^+$).

Compound 2.6

A solution of 7.25 (19 mg, 0.0256 mmol) and $Pd(OH)_2$ (5 mg) in MeOH (1 ml) was evacuated three times and each time the vacuum was broken with hydrogen (1 atm). After the third time, the reaction was stirred under hydrogen for 1 hour, filtered over celite, and concentrated in vacuo to give 16 mgs (100% yield) of a white film which was pure by TLC. $R_f$=0.4 (10:90) MeOH/DCM. $^1H$ NMR (300 MHz, $CDCl_3$) δ7.42 (d, 2H, J=8.05 Hz), 7.08 (d, 2H, J=8.05 Hz), 6.77 (d, 2H, J=8.04 Hz), 6.60 (d, 2H, J=8.2 Hz), 5.06 (bs, 1H), 4.83 (m, 1H), 4.53 (s, 2H), 4.20 (q, 2H, J=7.1 Hz), 3.82–3.55 (m, 71-1), 3.00 (m, 1H), 2.92–2.60 (m, SH), 2.02 (m, 1H), 1.87 (m, 1H), 1.73 (m, 1H), 1.24 (t3H, J=7.1 Hz), 0.84 (d, 3H, J=6.28 Hz), 0.79 (d, 3H, J=6.43 Hz).

Compound 2.6-(MeLeu(3-OH)$^1$, (D)MeSer$^3$, Lys$^7$)-CsA conjugate 2.10

A solution of ester 7.25 (36 mg, 0.0485 mmol) in MeOH/THF (1:1 0.480 ml) was treated with LiOH (0.1 ml, 1 N LiOH (aq)) and the solution was stirred for 3 hours, at which time an additional equivalent of LiOH was added and the reaction was stirred for another hour. The reaction was concentrated in vacuo, dissolved in $H_2O$ (20 ml) which was washed with ether (15 ml), acidified with 1 N $KHSO_4$, and extracted with DCM (2x) and EtOAc (3x). The combined organic layers were dried over $Na_2SO_4$, filtered, concentrated in vacuo to give acid 7.26 which was used directly in the next coupling reaction.

The Cbz-protected carboxylic acid derivative 7.26 (25 mg, 0.035 mmol) and the free amine CsA analog 4.11 (44 mg, 0.035 mmol, produced from 4.20 via general procedure K) were dissolved in DCM (1 ml). PyAOP (20 mg, 0.0385 mmol) and DIEA (0.0128 ml, 0.0735 mmol) were added sequentially to the solution and the reaction was stirred overnight at room temperature. After diluting with EthOAc, the mixture was washed with $H_2O$ (2x), dried over $Na_2SO_4$, and concentrated in vacuo. The residue was purified by flash chromatography (2–3–4–5% MeOH/DCM) to give 34 mg (50% yield) of conjugate 8.2. $R_f$=0.62 (9:1 DCM:MeOH). Conjugate 8.2 (25 mg, 0.0128 mmol) was dissolved in MeOH (1 ml) and $Pd(OH)_2$ (5 mg) was added to the solution. The reaction vessel was evacuated and the vacuum was broken each time with hydrogen (1 atm). After repeating this evacuation sequence three times, the reaction was stirred overnight under an atmosphere of hydrogen, filtered through an acrodisk, and concentrated in vacuo to give 22 mg (100% yield) of fully deprotected conjugate 2.10 which was pure by TLC. $R_f=0.59$ (9:1 DCM/MeOH). FABMS $C_{90}H_{151}N_{15}O_{21}S$) found 1811.2.

Examples 6–10

Anti-HIV Activity of the CsA Conjugates

The conjugates 2.9 and 2.10, and the Cbz-protected CsA analog (MeLeu(3-OH)$^1$, (D)MeSer$^3$, Lys(2Cl-Cbz)$^7$)-CsA 4.20 were sent to the National Cancer Institute for testing according to the NCI's "In Vitro Anti-AIDS Drug Discovery Program." The compounds 2.6 and 1.13 (an analog of VX-478) were also sent for comparative evaluation. The procedure used in the National Cancer Institute's test for agents active against human immunodeficiency virus (HIV) is designed to detect agents acting at any stage of the virus reproductive cycle. The assay basically involves the killing of T4 lymphocytes by HIV. Small amounts of HIV are added to cells, and two cycles of virus reproduction are necessary to obtain the required cell killing. Agents that interact with virions, cells, or virus gene-products to interfere with viral activities will protect cells from cytolysis. The system is automated in several features to accommodate large numbers of candidate agents and is generally designed to detect anti-HIV activity. However, compounds that degenerate or are rapidly metabolized in the culture conditions may not show activity in this screen. All tests are compared with at least one positive (e.g., AZT-treated) control done at the same time under identical conditions.

The Procedure:

1. Candidate agent is dissolved in dimethyl sulfoxide (unless otherwise instructed) then diluted 1:100 in cell culture medium before preparing serial half-log$_{10}$ dilutions. T4 lymphocytes (CEM cell line) are added and after a brief interval HIV-1 is added, resulting in a 1:200 final dilution of the compound. Uninfected cells with the compound serve as a toxicity control, and infected and uninfected cells without the compound serve as basic controls.
2. Cultures are incubated at 37° in a 5% carbon dioxide atmosphere for 6 days.
3. The tretrazolium salt, XTT, is added to all wells, and cultures are incubated to allow formazan color development by viable cells.
4. Individual wells are analyzed spectrophotometrically to quantitate formazan production, and in addition are viewed microscopically for detection of viable cells and confirmation of protective activity.
5. Drug-treated virus-infected cells are compared with drug-treated noninfected cells and with other appropriate controls (untreated infected and untreated noninfected cells, drug-containing wells without cells, etc.) on the same plate.
6. Data are reviewed in comparison with other tests done at the same time and a determination about activity is made.

(See Weislow, O. W., Kiser, R., Fine, D., Bader, J., Showmaker, R. H., Boyd, M. R.: New soluble-formazan assay for HIV-1 cytopathic effects: application to high-flux screening of synthetic and natural products for AIDS-antiviral activity. *J. Natl. Cancer Inst.* (1989) 81:577–586)

Examples 6, 7, and 8

Compounds 2.8, 2.10, and 4.20 were submitted to the NCI for HIV testing using the above protocol. Each sample was tested in quadruplicate runs of the assay. Representative graphs of the results are presented in FIGS. 1, 3, and 4, respectively. In each of the graphs, the solid line represents the growth of an HIV-infected culture which has been treated with one of the test compounds. The dashed line represents the growth of control culture. The control comprises an uninfected culture which has also been treated with the test compound.

Figure 3:
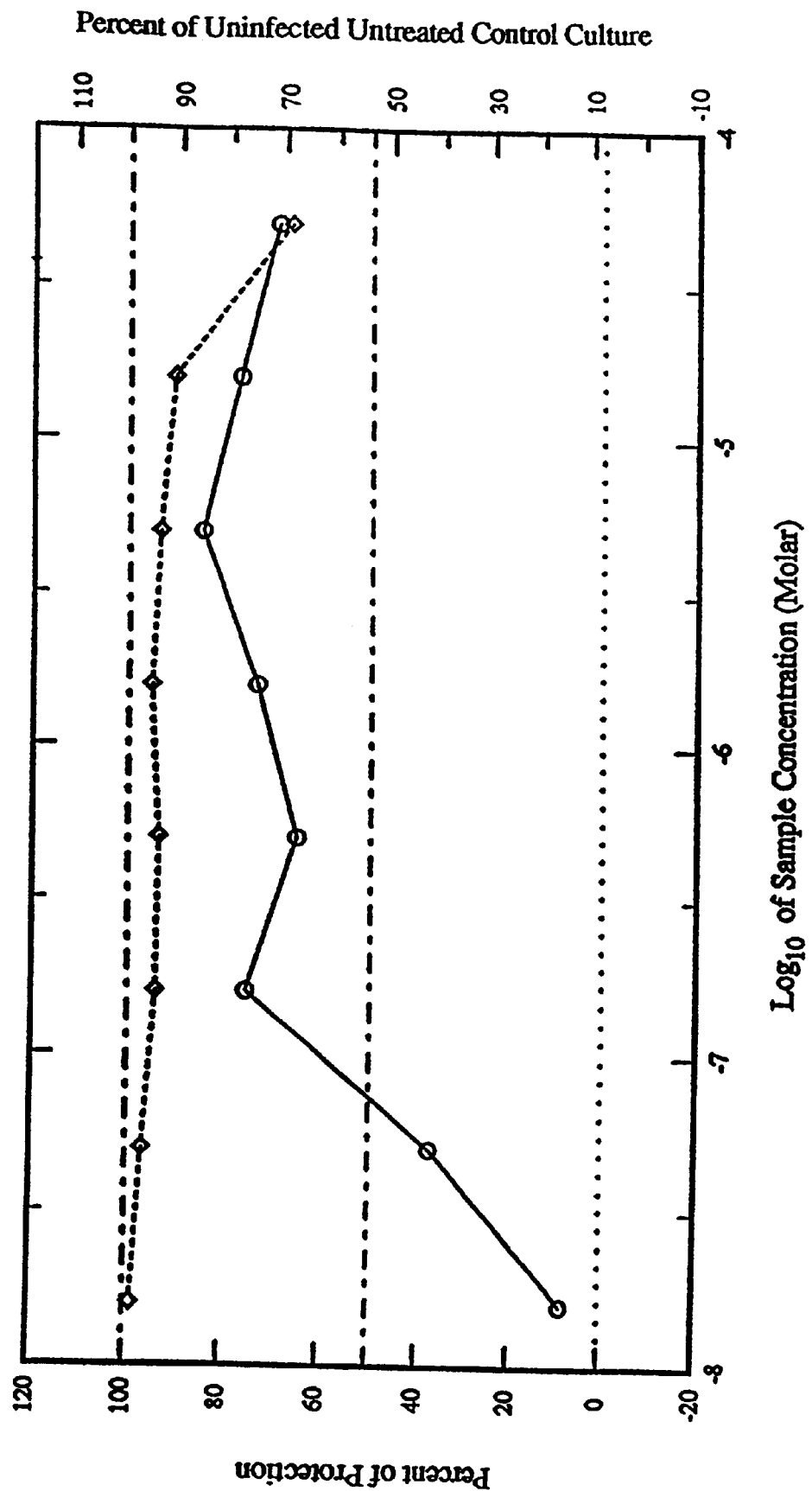
Figure 4:
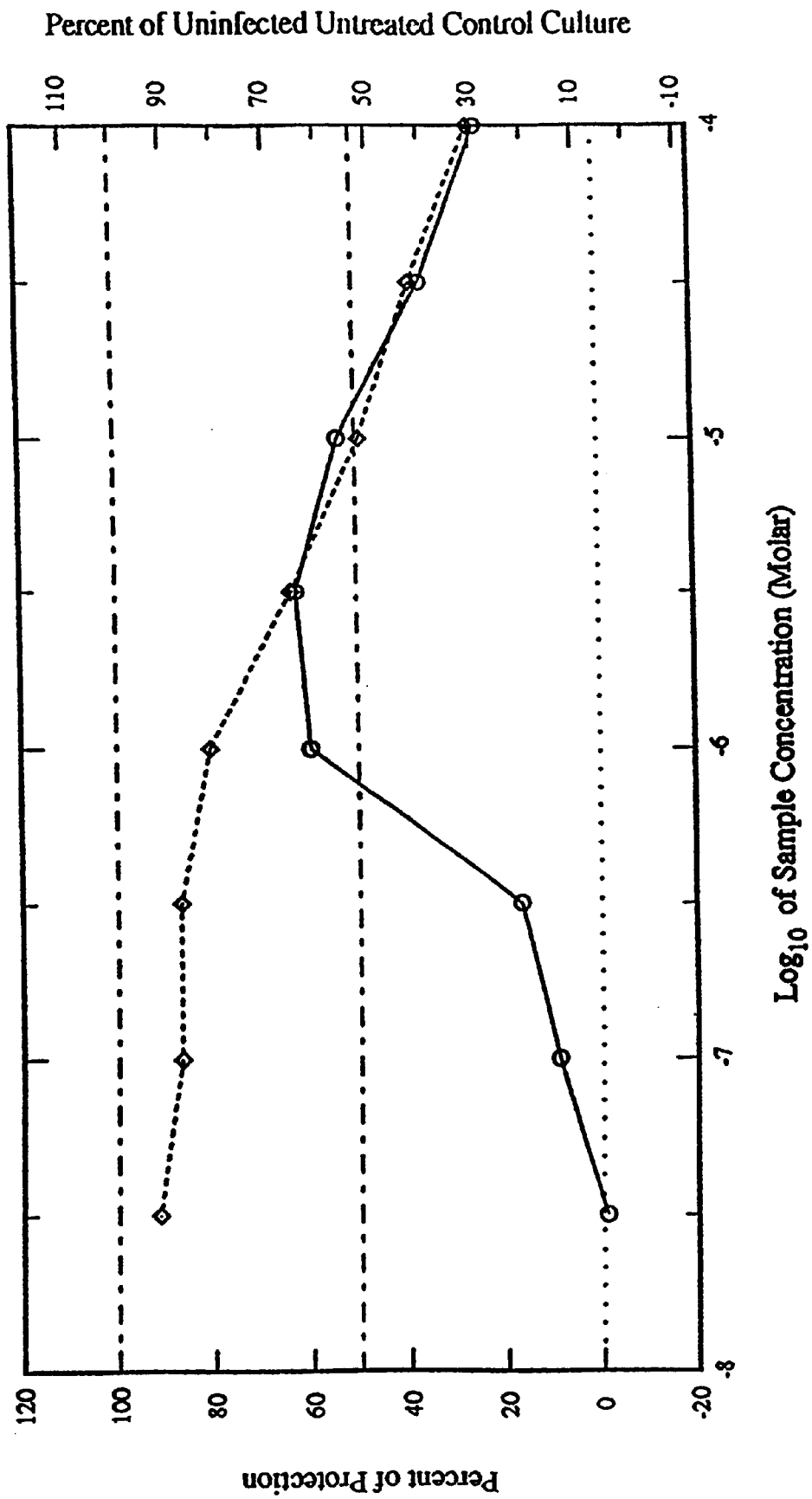

Conjugate 2.8, the results for which are depicted in FIG. 1, was "confirmed active" against HIV. Conjugate 2.10, the results for which are depicted in FIG. 3, was also "confirmed active" against HIV. CsA analog 4.20, the results for which are depicted in FIG. 4, was "confirmed moderate" against HIV.

These results clearly show that the subject compounds are active in the inhibition of HIV replication and thus are useful in the prevention and treatment of HIV-mediated disorders.

Example 9

Figure 2:
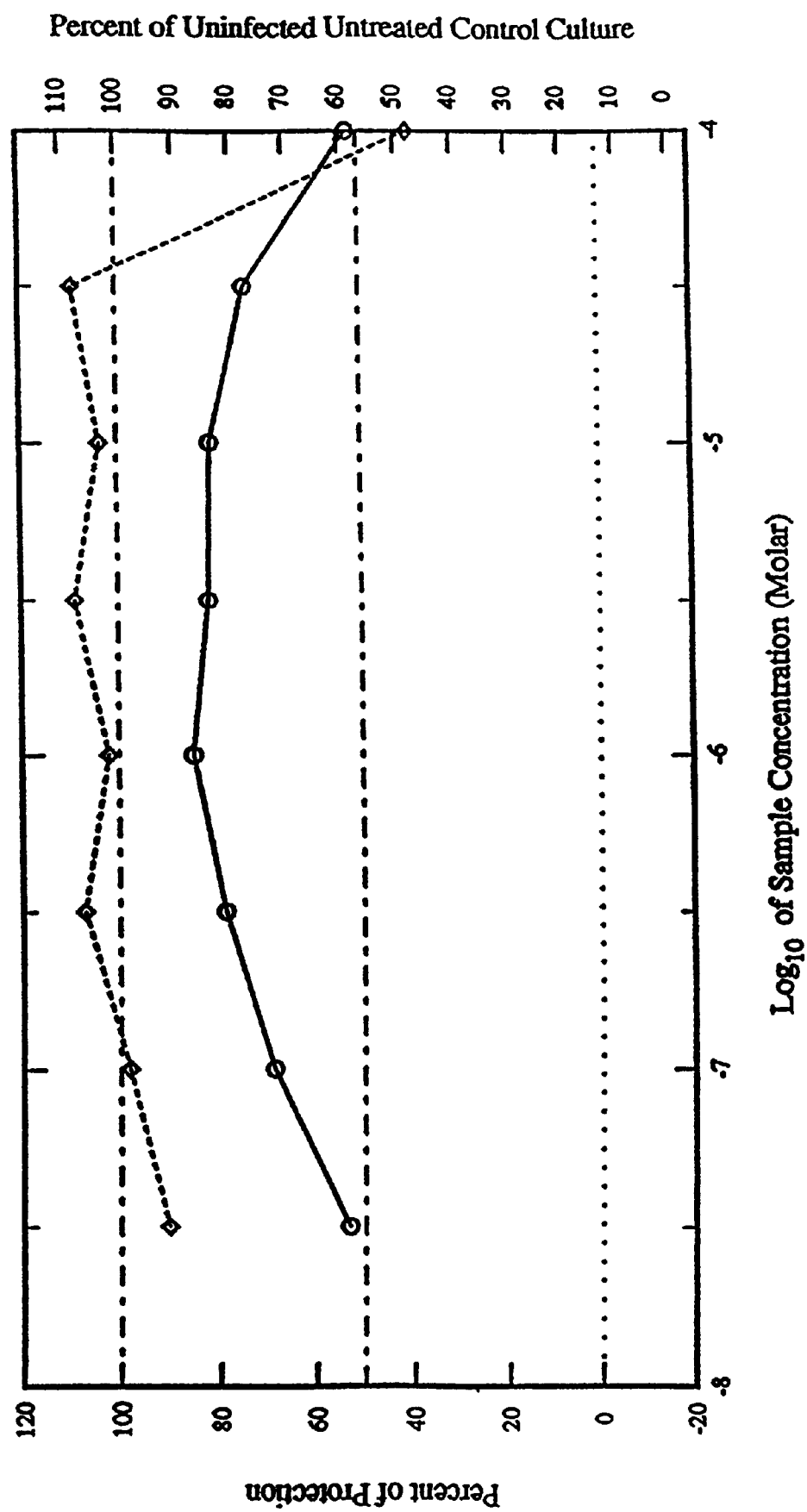

Compound 2.6 was subjected to the NCI anti-HIV assay described above. The results are presented in FIG. 2. Compound 2.6 was "confirmed moderate" in its activity against HIV.

These Examples show that the present invention provides a general approach for conjugating anti-HIV compounds to CsA in order to increase their bioavailability without having an adverse impact on their ability to inhibit HIV replication.

The invention is not confined to the particular reagents, reactions, compounds, and conjugates disclosed above, but embraces all forms and equivalents thereof as come within the scope of the following claims.

What is claimed is:

1. Non-immunosupressive cyclosporins comprising a cyclic undecapeptide of Formula I:

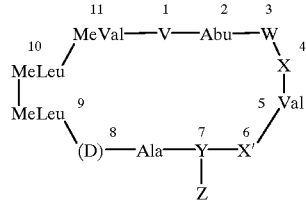

Formula (I)

wherein V is a MeLeu(3-OH), MeLeu, MeSer, MeSer-PG, MeThr, or MeThr-PG residue;

W is a (D)-N-methyl-amino acid or an N-methylglycyl residue;

X and X' are independently an N-methyl-leucinyl or an N-methylalanyl residue;

Y is a lysyl, homo-lysyl, ornithinyl, lysyl-PG, homo-lysyl-PG, or ornithinyl-PG residue;

wherein each PG is, independently, a side-chain protecting group; and

Z is absent or is an HIV protease inhibitor moiety conjugated to Y via a side-chain on Y and selected from the group consisting of

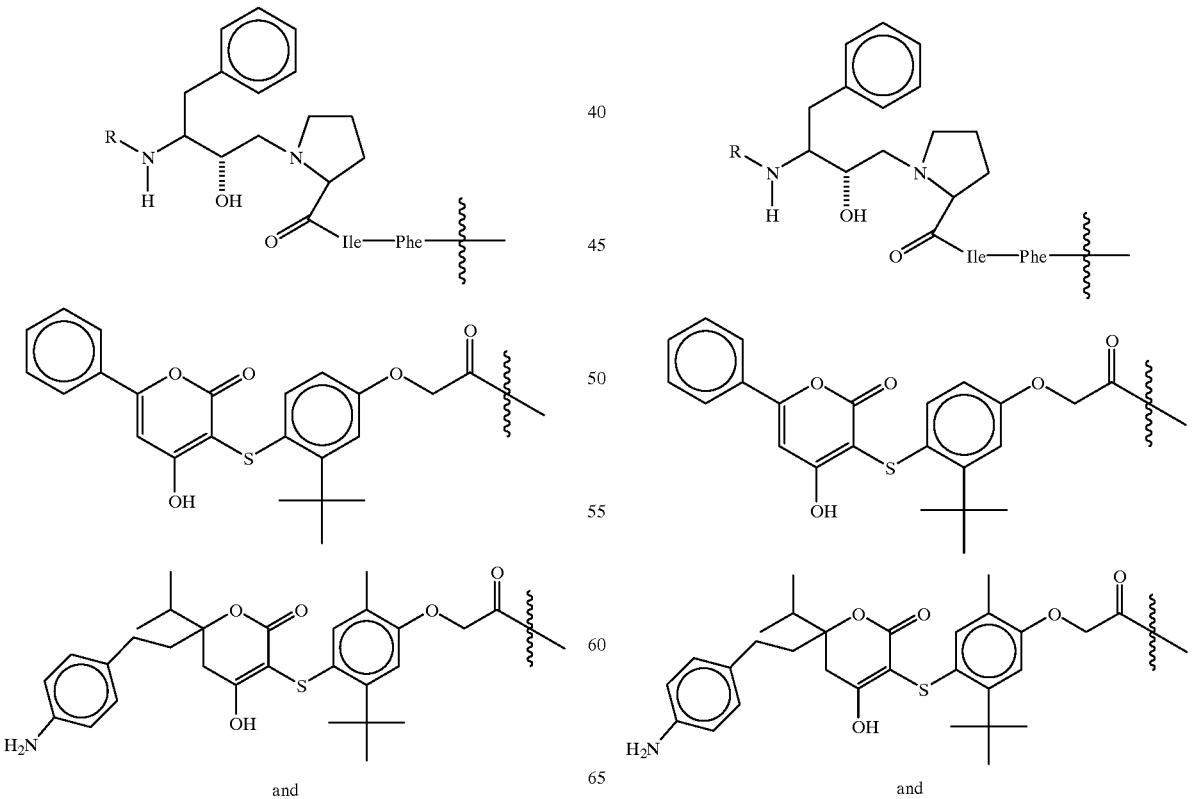

and

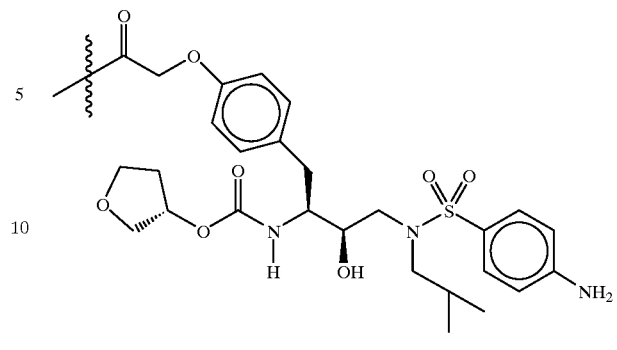

wherein R is Ac-Ser-Leu-Asn; and salts thereof.

2. The cyclosporins of claim 1, wherein Z is absent.

3. The cyclosporins of claim 1, wherein each PG is independently selected from the group consisting of allyl, benzyl, benzyloxy, 2-chloro-benzyloxy, and combinations thereof.

4. The cyclosporins of claim 1, wherein Y is a lysyl residue.

5. The cyclosporins of claim 4, wherein V is a 3-hydroxy-N-methyl-leucine residue, W is a N-methylglycyl, (D)-N-methylserinyl, or (D)-N-methylserinyl-PG residue, wherein PG is selected from the group consisting of allyl, benzyl, benzyloxy, and 2-chloro-benzyloxy.

6. The cyclosporins of claim 4, wherein X and X' are N-methylalanyl residues.

7. The cyclosporins of claim 4, wherein X and X' are N-methyl-leucine residues.

8. The cyclosporins of claim 4, wherein Z is selected from the group consisting of and

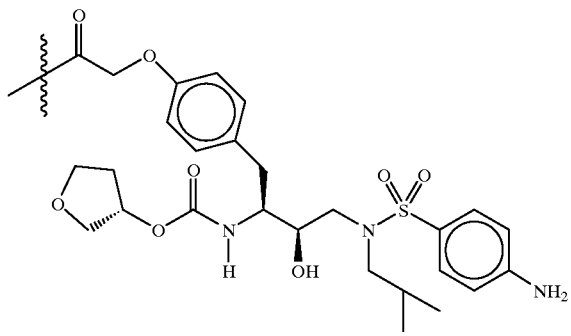

wherein R is Ac-Ser-Leu-Asn.

9. The cyclosporins of claim 8 wherein W is a (D)-N-methylserinyl or a (D)-N-methylserinyl-PG residue, wherein PG is selected from the group consisting of allyl, benzyl, benzyloxy, and 2-chloro-benzyloxy;

X and X' are N-methyl-leucine residues; and

Z is

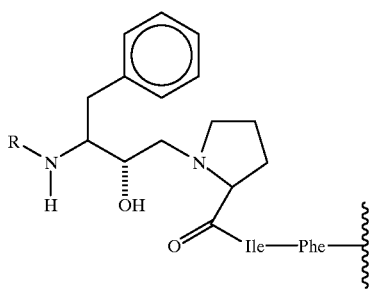

wherein R is Ac-Ser-Leu-Asn.

10. The cyclosporins of claim 8 wherein W is a (D)-N-methylserinyl or a (D)-N-methylserinyl-PG residue, wherein PG is selected from the group consisting of allyl, benzyl, benzyloxy, and 2-chloro-benzyloxy;

X and X' are N-methyl-leucine residues; and

Z is

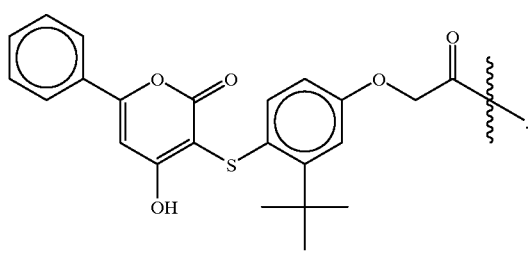

11. The cyclosporins of claim 8 wherein W is a (D)-N-methylserinyl or a (D)-N-methylserinyl-PG residue, wherein PG is selected from the group consisting of allyl, benzyl, benzyloxy, and 2-chloro-benzyloxy;

X and X' are N-methyl-leucine residues;

Z is

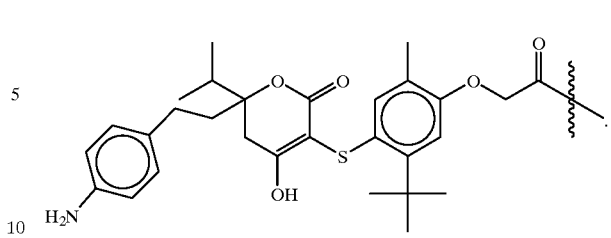

12. The cyclosporins of claim 8 wherein W is a (D)-N-methylserinyl or a (D)-N-methylserinyl-PG residue, wherein PG is selected from the group consisting of allyl, benzyl, benzyloxy, and 2-chloro-benzyloxy;

X and X' are N-methyl-leucine residues; and

Z is

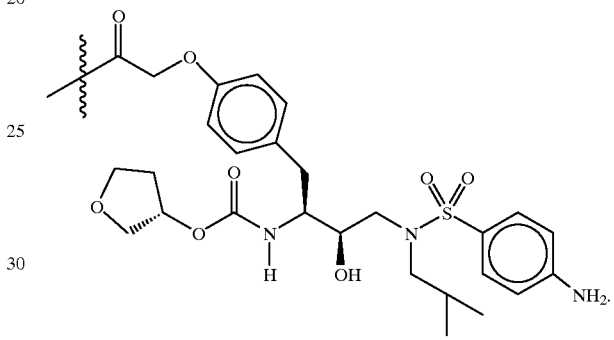

13. The cyclosporins of claim 8 wherein W is a (D)-N-methylserinyl or a (D)-N-methylserinyl-PG residue, wherein PG is selected from the group consisting of allyl, benzyl, benzyloxy, and 2-chloro-benzyloxy; and X and X' are N-methylalanyl residues.

14. A compound comprising a conjugate produced by:

(a) forming a cyclosporin analog of formula

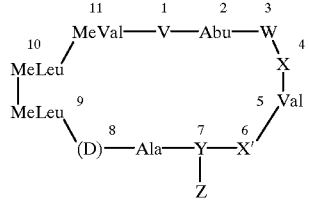

Formula (I)

wherein V is a MeLeu(3-OH), MeLeu, MeSer, MeSer-PG, MeThr, or MeThr-PG residue, wherein each PG is, independently, a side-chain protecting group; W is a (D)-N-methyl-amino acid residue or an N-methylglycyl residue; X and X' are independently an N-methyl-leucinyl or an N-methylalanyl residue; and Y is a lysyl, is formed; and comprising a lysyl residue having an ε-aminobutyl side-chain at position-7 of the cyclosporin analog; and (b) conjugating an HIV protease inhibitor, Z, to the ε-aminobutyl side-chain of the lysyl residue, Z being selected from the group consisting of

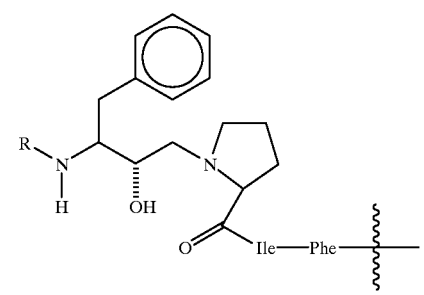

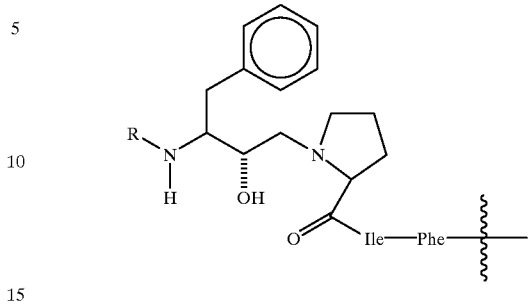

wherein R is Ac-Ser-Leu-Asn, is conjugated to Y.

16. The compound of claim 14, wherein in step (a) a cyclosporin analog wherein V is a MeLeu(3-OH) residue; W is a N-methylglycyl or (D)-N-methylserinyl residue; and X and X' are N-methyl-leucine residues is formed; and in step (b), Z, an HIV protease inhibitor moiety of formula

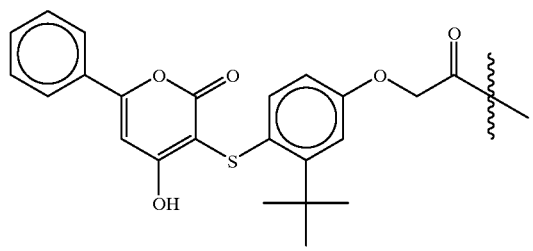

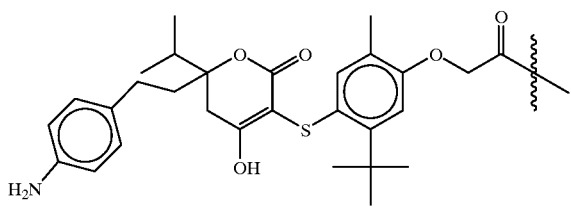

and

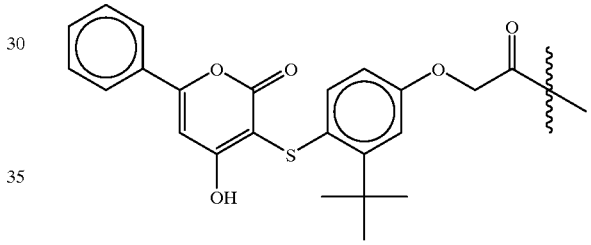

is conjugated to Y.

17. The compound of claim 14, wherein in step (a) a cyclosporin analog wherein V is a MeLeu(3-OH) residue; W is a N-methylglycyl or (D)-N-methylserinyl residue; and X and X' are N-methyl-leucine residues is formed; and in step (b), Z, an HIV protease inhibitor moiety of formula

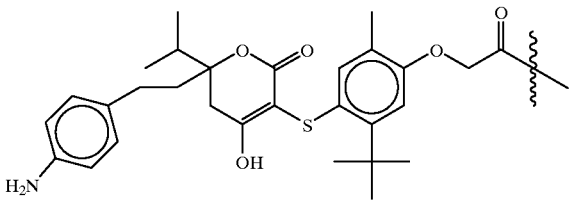

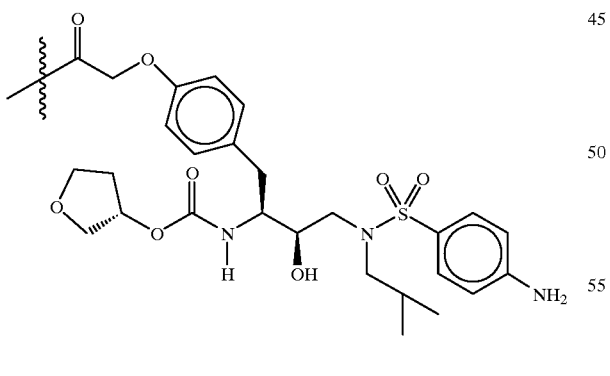

wherein R is Ac-Ser-Leu-Asn; and wherein the compound simultaneously binds to and inhibits the action of cyclophilin and HIV protease.

15. The compound of claim 14, wherein in step (a) a cyclosporin analog wherein V is a MeLeu(3-OH) residue; W is a N-methylglycyl or (D)-N-methylserinyl residue; and X and X' are N-methyl-leucine residues is formed; and is conjugated to Y.

18. The compound of claim 14, wherein in step (a) a cyclosporin analog wherein V is a MeLeu(3-OH) residue; W is a N-methylglycyl or (D)-N-methylserinyl residue; and X and X' are N-methyl-leucine residues is formed; and in step (b), Z, an HIV protease inhibitor moiety of formula

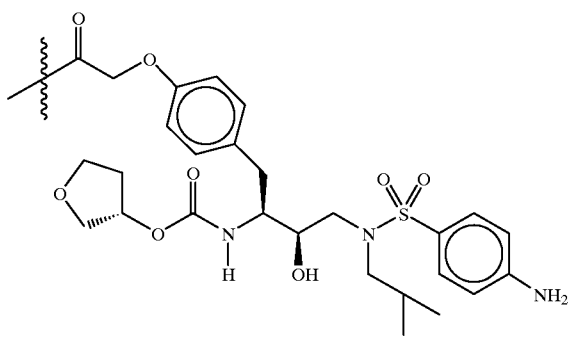

is conjugated to Y.

19. The compound of claim 14, wherein in step (a) a cyclosporin analog wherein X and X' are N-methylalanyl residues is formed.

20. A pharmaceutical composition for the treatment of HIV-mediated disorders in humans comprising an effective HIV protease-inhibiting amount of a compound of claim 1 or a pharmaceutically-acceptable salt thereof in combination with a pharmaceutically-acceptable liquid or solid carrier.

21. The pharmaceutical composition of claim 20 comprising a compound wherein Y is a lysyl residue; and Z is selected from the group consisting of

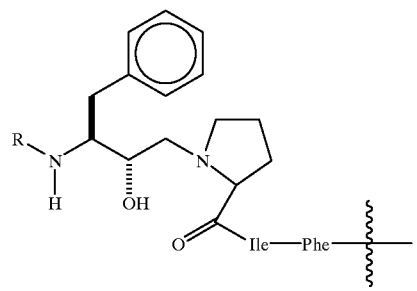

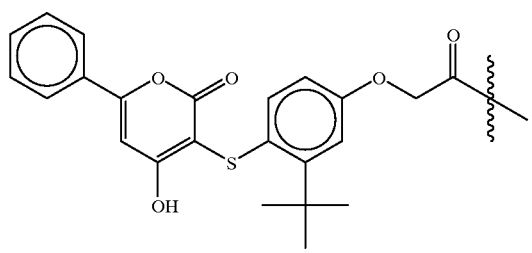

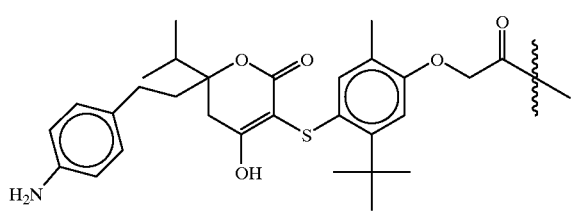

and

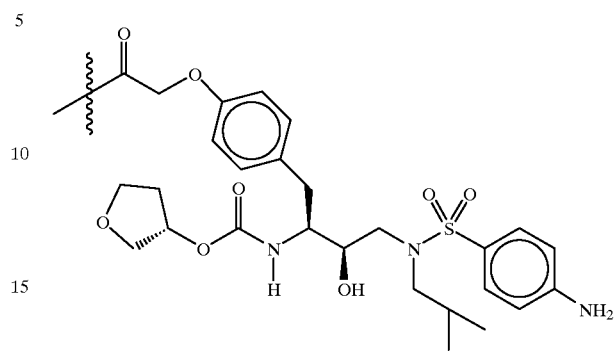

wherein R is Ac-Ser-Leu-Asn.

22. The composition of claim 21, wherein W is a (D)-N-methylserinyl or a (D)-N-methylserinyl-PG residue, wherein PG is selected from the group consisting of allyl, benzyl, benzyloxy, and 2-chloro-benzyloxy; and X and X' are N-methyl-leucinyl residues.

23. The composition of claim 21, wherein wherein W is a (D)-N-methylserinyl or a (D)-N-metbylserinyl-PG residue, wherein PG is selected from the group consisting of allyl, benzyl, benzyloxy, and 2-chloro-benzyloxy; and X and X' are N-methylalanyl residues.

24. A pharmaceutical composition for the prevention and treatment of HIV-mediated disorders in humans comprising an effective HIV protease-inhibiting amount of a compound of claim 14 or a pharmaceutically-acceptable salt thereof in combination with a pharmaceutically-acceptable liquid or solid carrier.

25. A method of treating HIV-mediated disorders in humans comprising administering to a human subject in need thereof an effective HIV protease-inhibiting amount of one or more compounds of claim 1, or pharmaceutically-acceptable salts thereof.

26. The method of claim 25, wherein one or more compounds selected from the group consisting of:

Formula (I)

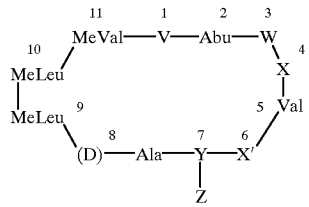

wherein V is a MeLeu(3-OH) residue;

wherein W is an N-methylglycyl, (D)-N-methylserinyl, or (D)-N-methylserinyl-PG residue, wherein each PG is, independently, a side-chain protecting group; X and X' are independently an N-methyl-leucinyl or an N-methylalanyl residue; Y is a lysyl residue; and Z is selected from the group consisting of

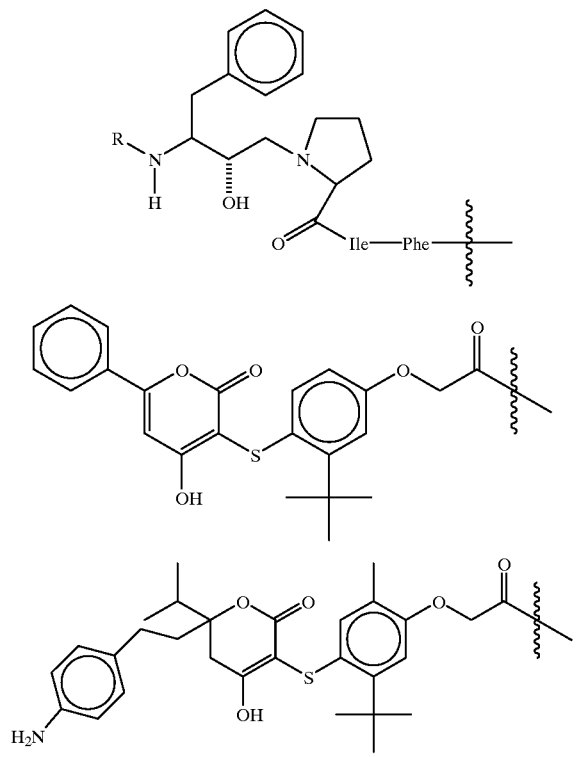

and

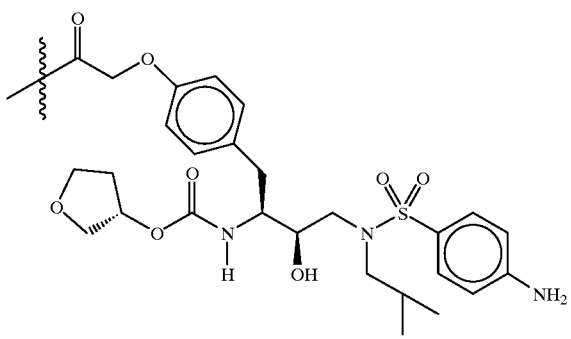

wherein R is Ac-Ser-Leu-Asn; and pharmaceutically-acceptable salts thereof, is administered.

27. The method of claim 26, wherein a compound where Z is

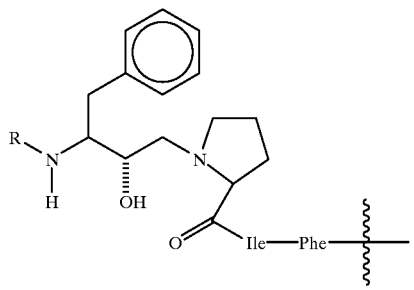

wherein R is Ac-Ser-Leu-Asn, is administered.

28. The method of claim 26, wherein a compound where Z is

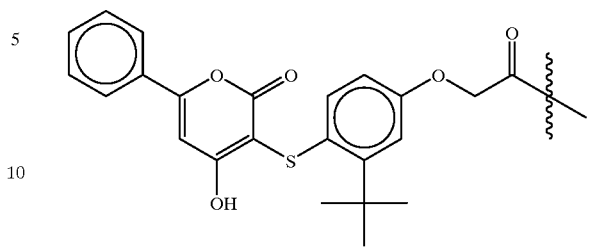

is administered.

29. The method of claim 24, wherein a compound where Z is

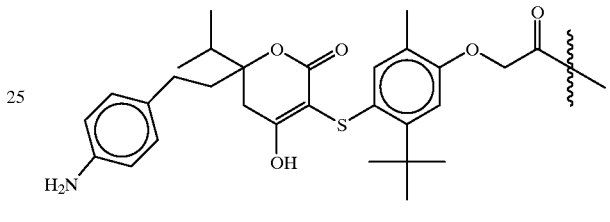

is administered.

30. The method of claim 24, wherein a compound where Z is

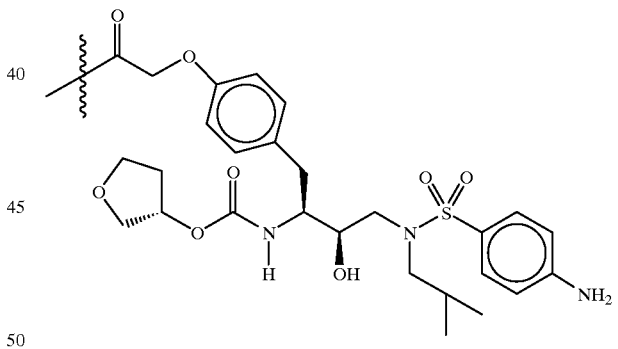

is administered.

31. A method of preventing and treating HIV-mediated disorders in humans comprising administering to a human subject in need thereof an effective HIV protease-inhibiting amount of one or more compounds of claim 13, or pharmaceutically-acceptable salts thereof.

* * * * *